US006365616B1

(12) United States Patent
Kohn et al.

(10) Patent No.: US 6,365,616 B1
(45) Date of Patent: Apr. 2, 2002

(54) METHIMAZOLE DERIVATIVES AND TAUTOMERIC CYCLIC THIONES TO TREAT AUTOIMMUNE DISEASES

(75) Inventors: Leonard D. Kohn, Bethesda, MD (US); Robert W. Curley, Columbus; John M. Rice, West Chester, both of OH (US)

(73) Assignees: Sentron Medical, Inc., Rockville, MD (US); The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/382,960

(22) Filed: Aug. 25, 1999

Related U.S. Application Data

(63) Continuation-in-part of application No. 09/141,311, filed on Aug. 31, 1998, now abandoned.

(51) Int. Cl.$^7$ .............................................. A61K 31/415

(52) U.S. Cl. ....................................... 514/396; 514/398

(58) Field of Search ................................. 514/396, 398

(56) References Cited

U.S. PATENT DOCUMENTS

| | | |
|---|---|---|
| RE24,505 E | 7/1958 | Rimington et al. .......... 260/309 |
| 3,341,549 A | 9/1967 | Henry ........................ 260/309 |
| 3,390,150 A | 6/1968 | Henry ........................ 260/244 |
| 3,505,350 A | 4/1970 | Doebel et al. ............... 260/309 |
| 3,641,049 A | 2/1972 | Sandstrom et al. ....... 260/309.6 |
| 3,644,392 A | 2/1972 | Henry ........................ 260/309 |
| 4,073,905 A | 2/1978 | Kummer et al. ........ 424/248.56 |
| 4,148,885 A | 4/1979 | Renoux et al. .............. 424/162 |
| 5,010,092 A | 4/1991 | Elfarra ........................ 514/359 |
| 5,051,441 A | 9/1991 | Matsumoto et al. ......... 514/244 |
| 5,202,312 A | 4/1993 | Matsumoto et al. .......... 514/18 |
| 5,310,742 A | 5/1994 | Elias .......................... 514/274 |
| 5,556,754 A | 9/1996 | Singer et al. .................. 435/6 |
| 5,578,645 A | 11/1996 | Askanazi et al. ........... 514/648 |
| 5,587,369 A | 12/1996 | Daynes et al. .............. 514/178 |

FOREIGN PATENT DOCUMENTS

| | | |
|---|---|---|
| GB | 592453 | 3/1945 |
| WO | 9204033 | 3/1992 |
| WO | 9428897 | 12/1994 |

OTHER PUBLICATIONS

Kjellin and Sandstrom, Acta Chemica Scandinavica, 23: (1969) 2879–2887.
Kjellin and Sandstrom, Acta Chemica Scandinavica, 23: (1969) 2888–2899 U.S.P. Dictionary.
(US Pharmacopeia, Rockville, Maryland, 1996) "Entry for Methimazole".

Suzuki, et al, ARVO Abstract, (1995) "Methimaxole (MMI) An Agent Capable Of Reducing MHC Class I Expression, Inhibits Experimental Melanin–Induced Uveitis (EMIU) And Experimental Autoimmune Uveoretinitis (EAU)".
Guiliani, et al., The Endocrine Society, (1994) "Down–Regulation Of Major Histocompatibility Complex (MHC) Class I Gene Expression In FRTL–5 Thyroid Cells By Hydrocortisone Is Transcriptional And Mediated By The p50 Subunit Of NF–B".
Napolitano, et al., The Endocrine Society, (1994) "Methimazole Regulation Of major Histocompatibility (MHC) Class I Gene Expression In Thyroid Cells Involves TSH–And Insulin–Activated Transcription Factors".
Neumann, et al., Science 269, 549–522 (1995) "Induction of MHC Class I In Genes in Neurons".
Sartoris, et al., International Journal of Clinical & Laboratory Research 25: 71–78 (1995) "Transcriptional Regulation of MHC Class II Genes".
Volpé, Thyroid 4(2), 217–223, Evidence That the Immunosuppressive Effects of Antithyroid Drugs Are Mediated through Actions on the Thyroid Cell, Modulating Thyrocyte–Immunocyte Signaling: A Review (1990).
Cooper, New England Journal of Medicine 311(21), 1353–1362 (1984) "Medical Progress, Antithyroid Drugs".
Mozes, et al., Science 261, 91–93 (1993) "Resistance of MHC Class I–Deficient mice to Experimental Systemic Lupus Erythematosus".
Cooper, "Treatment of Thyrotoxicosis" in Werner and Ingbar's The Thyroid, Seventh Edition, (1996) Lippincott–Raven, pp. 713–714.
Chan, et al., Journal of Immunology, 154, 4830–4835 (1995) "Periocular Inflammation in Mice with Experimental Systemic Lupus Erythematosus".
Krieg, Trends in Microbiology 4(2) 73–77 (1996) "Lymphocyte activation CpG dinucleotide motifs in prokaryotic DNA".
Shimojo, et al., Proc. Natl. Acad. Sci. 93, 11074–11079 (1996) "Induction of Graves–like disease in mice by immunization with fibroblasts transfected with the thyrotropin receptor and a class II molecule".

(List continued on next page.)

Primary Examiner—Theofore J. Criares
(74) Attorney, Agent, or Firm—Frost Brown Todd LLC

(57) ABSTRACT

The present invention provides methods for treating autoimmune diseases in mammals and for preventing or treating transplantation rejection in a transplant recipient. These methods utilize specifically-defined methimazole derivatives and tautomeric cyclic thione compounds, as well as pharmaceutical compositions containing those compounds. These compounds and compositions have been found to be at least as effective as methimazole in terms of pharmaceutical activity, while having less of an adverse affect on thyroid function. They are also more soluble in conventional pharmaceutical vehicles than methimazole. An assay for screening the activity of compounds useful against autoimmune diseases (ability to suppress expression of MHC Class I and II molecules) is also taught.

44 Claims, 17 Drawing Sheets

OTHER PUBLICATIONS

Figure 1:
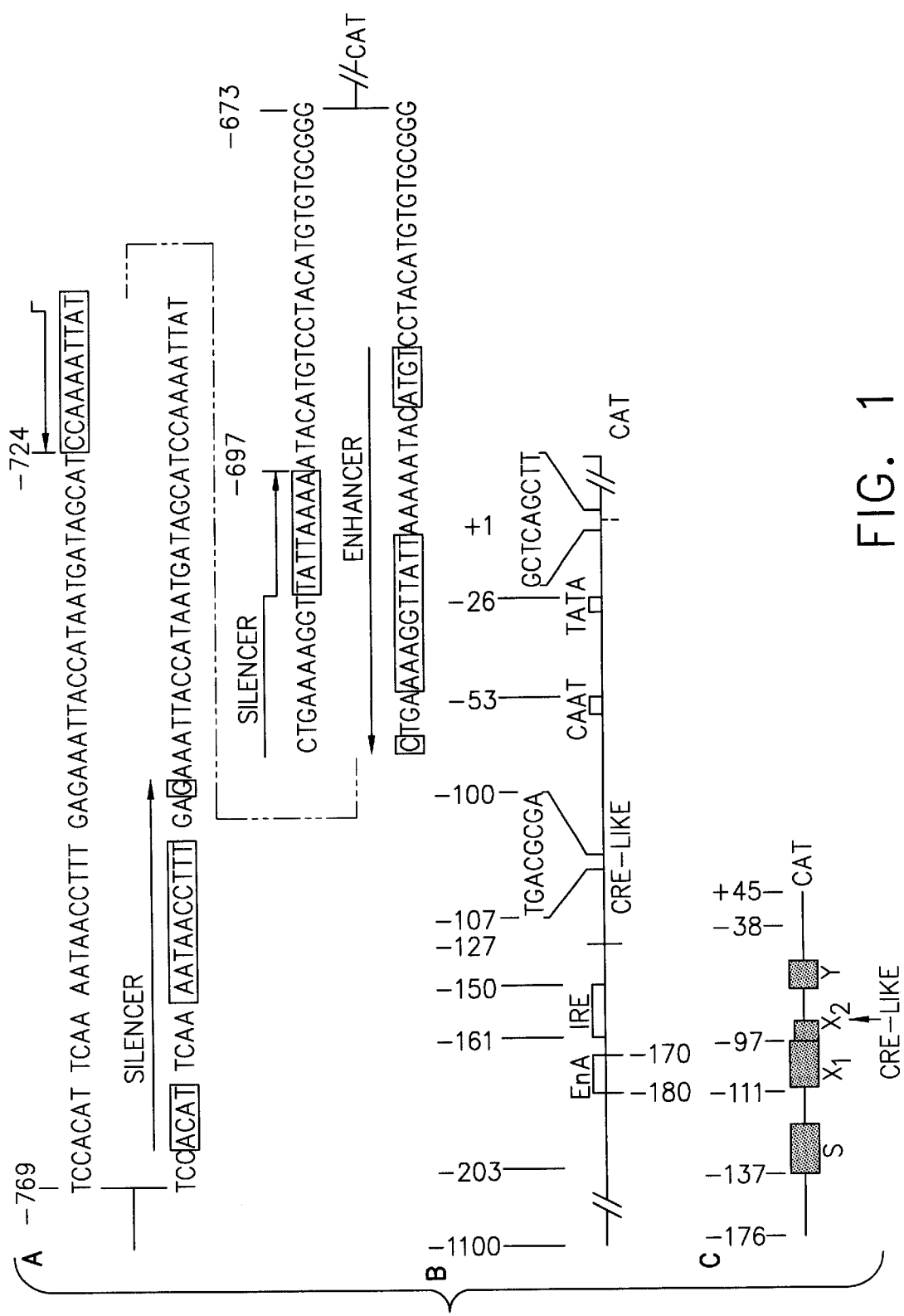

Wicker, et al., Diabetes, 35, 855–860 (1986) "Transfer of Autoimmune Diabetes Mellitus With Splenocytes From Nonobese Diabetic (NOD) Mice".

Oren, et al., Aliment Pharmacol Ther 11(2) 341–345 (1997) "Anti–Thyroid Drugs Decrease Mucosal Damage in a Rat Model of Experimental Colitis".

Montain, et al., Endocrinology, 139(1), 280–289 (1998) "Major Histocompatibility Class II HLA–Dra Gene Expression in Thyrocytes: Counter Regulation by the Class II Transactivator and the Thyroid Y Box Protein".

Montain, et al., Endocrinology, 139(1), 290–302 (1998) "Regulation of Major Histocompatibility Class II Gene Expression in FRTL–5 thyrocytes: Opposite Effects of Interferon and Methimazole*".

```
-250
 |
CTCCGCAGCCAGGCCTGGCCTCTCAGGGTCTCCAGGCTCCAGGGCGGAGTCTGGGCGGGAG
-190
 |
GCGCGGTGTGGGAGTCCCCGTGTCCCCCAGTTTCACTTCTCCGTCTCGCAACCTGTGTG
-130 -127              -107 CRE -100                    -89
 |    |                |        |                       |
GGACCGTCCTGCCCGGACACTCG[TGACGCGA]CCCCACTTCTCTCTCCTATTGCGTGTCCG
-70           -53                              -26
 |             |                                |
GTTTCTGGAGAAGC[CAAT]CGGGCGCCACTGCGGTTCCCGGT[TCTAA]ACTCTCCACCCACCC
-10     +1
 |     |
GGCTCTGCTCAGCTTCTCCCCAGACTCCGAGGCTGAGGATC[ATG]GGGCCTGAGCCCTCT
                                           MET GLY PRO GLY ALA LEU GLU V
```

FIG. 3

US 6,365,616 B1

METHIMAZOLE DERIVATIVES AND TAUTOMERIC CYCLIC THIONES TO TREAT AUTOIMMUNE DISEASES

This is continuation-in-part of U.S. patent application Ser. No. 09/141,311, Kohn, et al., filed Aug. 31, 1998, now abandoned.

TECHNICAL FIELD

This invention relates to the treatment of autoimmune diseases and transplantation rejection in mammals. More specifically, the present invention relates to the use of a narrowly-defined group of methimazole derivatives and tautomeric cyclic thiones for the purposes described herein.

BACKGROUND OF THE INVENTION

A primary function of immune response in mammals is to discriminate self from non-self antigens and to eliminate the latter. The immune response involves complex cell to cell interactions and depends primarily on three major types of immune cells: thymus derived (T) lymphocytes, bone marrow derived (B) lymphocytes, and macrophages. Immune response is mediated by molecules encoded by the major histocompatibility complex (MHC). The two principal classes of MHC molecules, Class I and Class II, each comprise a set of cell surface glycoproteins (see Stites, D. P. and Terr, A. I. (eds), "Basic and Clinical Immunology", Appelton and Lange, Norwalk, Conn./San Mateo, Calif., 1991). MHC Class I molecules are found on virtually all somatic cell types, although at different levels in different cell types. By contrast, MHC Class II molecules are normally expressed only on a few cell types, such as lymphocytes, macrophages and dendritic cells.

Antigens are presented to the immune system by antigen presenting cells in the context of Class I or Class II cell surface molecules, for example, CD4$^+$ helper T-lymphocytes recognize antigens in association with Class II MHC molecules, and CD8$^+$ cytotoxic lymphocytes (CTL) recognize antigens in association with Class I gene products. It is currently believed that MHC Class I molecules function primarily as the targets of the cellular immune response, while Class II molecules regulate both the humoral and cellular immune response (Klein, J. and Gutze, E., "Major Histocompatibility Complex", Springer Verlag, New York, 1977; Unanue, E. R., Ann. Rev. Immunology, 2:295–428, (1984)). MHC Class I and Class II molecules have been the focus of much study with respect to research in autoimmune diseases because of their roles as mediators or initiators of immune response. MHC Class II antigens have been the primary focus of research in the etiology of autoimmune diseases, whereas MHC Class I antigens have historically been the focus of research in transplantation rejection.

Numerous experimental animal models for human disease have linked aberrant expression and/or function of MHC Class I and MHC Class II antigens to the autoimmune disease process, for example, insulin-dependent diabetes mellitus (IDDM) (Tisch and McDevitt, Cell 85: 291–297 (1996)), systemic lupus erythematosus (SLE) (Kotzin, Cell 85: 303–306 (1996)), and uveoretinitis (Prendergast et al., Invest. Opthalmol. Vis. Sci. 39: 754–762 (1998)).

The pathological link between MHC Class I and/or Class II expression and disease has been examined in many of these model systems using a variety of biochemical and genetic approaches. However, the strongest evidence for aberrant MHC gene function as a mediator of autoimmune disease stems from transgenic animal models in which the MHC genes have been inactivated. Using MHC Class I deficient animals resistance to the autoimmune disease process—and hence the dependence of autoimmunity upon MHC gene expression—can be directly demonstrated in animal models for IDDM (Serreze et al., Diabetes 43: 505–509 (1994)), and SLE (Mozes et al., Science 261: 91–93 (1993)).

Moreover, the dependence of the progressive multifocal inflammatory autoimmune disease phenotype exhibited by TGF-betal deficient transgenic mice (Shull et al., Nature 359: 693–699 (1992); Kulkarni et al., Proc. Natl. Acad. Sci. 90: 770–774 (1993); Boivin et al., Am. J. Pathol. 146: 276–288 (1995)) on MHC Class II expression has recently been demonstrated using MHC Class II deficient animals. Specifically, TGF-betal deficient animals lacking MHC Class II expression are without evidence of inflammatory infiltrates, circulating antibodies, or glomerular immune complex deposits (Letterio et al., J. Clin. Invest. 98: 2109–2119 (1996)).

In addition to the information supportive of MHC Class I and Class II antigens as critical for the development of autoimmunity in animal models there is equally strong evidence linking autoimmune processes with expression of MHC Class I and MCH Class II antigens in humans.

Graves' disease is a relatively common autoimmune disorder of the thyroid. In Graves' disease, autoantibodies against thyroid antigens, particularly the thyrotropin receptor (TSHR), alter thyroid function and result in hyperthyroidism (Stites, D. P. and Terr, A. I. (eds), "Basic and Clinical Immunology", Appleton and Lang, Norwalk, Conn./San Mateo, Calif., 1991, pp. 469–470)). Thyrocytes from patients with Graves' disease have aberrant MHC Class II expression and elevated MHC Class I expression (Hanafusa et al., Lancet 2:1111–1115 (1983); Bottazzo et al., Lancet 2:1115–1119 (1983); Kohn, et al., in "International Reviews of Immunology," Vol. 912, pp. 135–165, (1992)). Aberrant expression of MHC Class II and TSHR on fibroblasts, but not either alone, has recently been shown to induce Graves' disease in mice, i.e., aberrant expression of Class II on target tissue can yield autoimmune disease in animals with normal immune systems. Thionamide therapy has historically been used to treat Graves' disease. The most commonly used thionamides are methimazole, carbimazole and propylthiouracil. These thionamides contain a thiourea group; the most potent are thioureylenes (W. L. Green, in Werner and Ingbar's "The Thyroid": A Fundamental Clinical Text, 6$^{th}$ Edition, L. Braverman and R. Utiger (eds), J. B. Lippincott Co., 1991, p. 324). The basis for thionamide therapy has, however, not focused on immune suppression. Rather, the basis has been suppression of thyroid hormone formation. Experiments suggesting an effect on immune cells, to inhibit antigen presentation or antibody formation, are largely discounted as nonphysiologic in vitro artifacts of high MMI concentration. MMI activity under those circumstances is suggested to be based on free-radical scavenger activity. See D. S. Cooper, in Werner E. Ingbar's "The Thyroid", op. cit., pp. 712–734.

Systemic lupus erythematosus (SLE) is a chronic autoimmune disease that, like Graves' disease, has a relatively high rate of occurrence. SLE affects predominantly women, the incidence being 1 in 700 among women between the ages of 20 and 60 (Abbus, A. K., Lichtman, A. H., Pober, J. S. (eds), "Cellular and Molecular Immunology", W.B. Saunders Company, Philadelphia, 1991, pp. 360–370). SLE is characterized by the formation of a variety of autoantibodies and by 20 multiple organ system involvement (Stites and Terr, ibid, pp. 438–443). Current therapies for treating SLE involve the use of corticosteroids and cytotoxic drugs, such as cyclophosphamide. Immunosuppressive drugs, such as cyclosporin, FK506 or rapamycin suppress the immune system by reducing T cell numbers and function (Morris, P. J., Curr. Opin. in Immun., 3:748–751 (1991)). While these immunosuppressive therapies alleviate the symptoms of SLE and other autoimmune diseases, they have numerous severe side effects. In fact, extended therapy with these agents may cause greater morbidity than the underlying disease. A link between MHC Class I expression and SLE in animal models has been established. Thus, Class I deficient mice do not develop SLE in the 16/6 ID model (Mozes, et al., Science 261: 91–93 (1993)).

Women suffering from SLE who have breast cancer face particular difficulties. These individuals are immunosuppressed as a result of corticosteroid and cytotoxic drug treatment for SLE; radiation therapy for the treatment of the cancer, a current treatment of choice, would additionally exacerbate the immunosuppressed state. Further, radiation therapy can exacerbate disease expression or induce severe radiation complications. For these individuals, alternative therapies that would allow for simultaneous treatment of SLE and cancer are greatly needed.

Diabetes Mellitus is a disease characterized by relative or absolute insulin deficiency and relative or absolute glucagon excess (Foster, D. W., Diabetes Mellitus. In Stanbury, J. B., et al., The Metabolic Basis of Inherited Disease. Ch. 4, pp 99–117, 1960). Type I diabetes appears to require a permissive genetic background and environmental factors. Islet cell antibodies are common in the first months of the disease. They probably arise in part to β cell injury with leakage cell antigens but also represent a primary autoimmune disease. The preeminent metabolic abnormality in Type I diabetes is hyperglycemia and glucosuria. Late complications of diabetes are numerous and include increased atherosclerosis with attendant stroke and heart complications, kidney disease and failure, and neuropathy which can be totally debilitating. The link to HLA antigens has been known since 1970. Certain HLA alleles are associated with increased frequency of disease, others with decreased frequency. Increased MHC class I and aberrant MHC class II expression in islet cells has been described (Bottazzo et al., NEJM 313: 353–360 (1985); Foulis and Farquharson, Diabetes 35: 1215–1224 (1986)). A definitive link to MHC class I has been made in a genetic animal model of the disease. Thus MHC class I deficiency results in resistance to the development of diabetes in the NOD mouse (Sereze et al., Diabetes 43: 505–509 (1994); Wicker et al., Diabetes 43: 500–504 (1994)).

A wealth of genetic, biochemical and animal model data support a contributory role of inflammatory cytokines (e.g., IL-12, IL-18; and particularly IFN-gamma) in the autoimmune process (Sarvetnick, J Clin Invest 99: 371–372 (1997)). Studies using non-obese diabetic (NOD) mice, which spontaneously develop auto-immune diabetes reminiscent of Type I human IDDM, are particularly illustrative in demonstrating how IFN-gamma stimulated processes play critical roles in the development of autoimmunity; and how the actions of other pro-inflammatory cytokines are channeled through IFN-gamma stimulated processes— among which are the enhanced expression of MHC Class I and MHC Class II antigens.

IL-12 and IL-18 (IFN-gamma inducing factor) are known to act synergistically in stimulating production of IFN-gamma in T cells (Micallef et al., Eur. J. Immunol. 26: 1647–1651 (1996)). In diabetic NOD mice the systemic expression of IL-18 (Rothe et al., J. Autoimmun. 10: 251–256 (1997)) and islet expression of IL-12 are increased (Rabinovitch et al., J. Autoimmun. 9: 645–651 (1996)). Moreover, additional IL-12 accelerates autoimmune diabetes in NOD mice (Trembleau et al., J. Exp. Med. 181: 817–821 (1995)). Genetic analysis has determined the IL-18 gene maps to a chromosomal region (Idd2) associated with a genetic susceptibility for autoimmune diabetes (Kothe et al., J. Clin. Invest. 99: 469–474 (1997)). These reports support help to define a critical role for IFN-gamma in the process of autoimmunity.

The role of IFN-gamma in the autoimmune process is further substantiated by studies where IFN-gamma's signaling capacity was abrogated in some manner. For example, transgenic NOD mice deficient in the cellular receptor for IFN-gamma (Wang et al., Proc. Natl. Acad. Sci. 94: 13844–13849 (1997)) do not develop autoimmune diabetes. NOD mice treated with a neutralizing antibody for IFN-gamma (Debray-Sachs et al., J. Autoimmun. 4:237–248 (1991)) also do not develop autoimmune diabetes. While it is somewhat surprising that the onset of diabetes is only delayed in transgenic NOD mice deficient in IFN-gamma (Hultgren et al., Diabetes 45: 812–817 (1996)), this observation only further stresses the importance of blocking the IFN-gamma signal—and more importantly IFN-gamma stimulated downstream events—for the effective prevention of autoimmunity in NOD mice.

Analogous observations have been made in animal models for SLE. Soluble IFN-gamma receptor blocks disease in the NZB/NZW F1 spontaneous autoimmune disease model for SLE (Ozmen et al., Eur. J. Immunol. 25: 6–12 (1995)); uveitis, where the targeted expression of IFN-gamma increases ocular inflammation (Geiger et al., Invest. Opthalmol. Vis. Sci. 35: 2667–2681 (1994)); and autoimmune gastritis, where neutralizing IFN-gamma antibody blocks disesase (Barret et al., Eur. J. Immunol. 26: 1652–1655 (1996)). Moreover, in humans treatment with IFN-gamma has been reported to be associated with the development of an SLE-like disease (Graninger et al., J. Rheumatol. 18: 1621–1622 (1991)).

It is well recognized that γ-IFN increases MHC class I and class II expression in many tissues and thus is linked to the action of a coregulatory molecule, the class II transactivator (Mach et al., Ann Rev Immunol 14: 301–331 (1996); Chang et al., Immunity 4: 167–178 (1996); Steimle et al., Science 265: 106–109 (1994); Chang et al., J Exp Med 180: 1367–1374 (1994); Chin et al. Immunity 1: 687–697 (1994); Montani, V. et al., Endocrinology 139: 280–289 (1998)). It is also known that MMI can inhibit IFN-increased class I and class II expression in thyroid (Saji et al., J. Clin. Endocrinology. Metab. 75: 871–878 (1992); Montani et al., Endocrinology. 139: 290–302 (1998)). Finally, it has been shown that MMI decreases expression of CIITA increased class II expression and this appears to be related to the action of MMI to enhance Y box protein gene expression; the Y box protein suppresses class II gene expression (Montani et al., Endocrinology 139: 280–289 (1998)).

As is true for autoimmune diseases, there is a great need for new and different ways of treating or preventing transplantation rejection. Transplantation rejection occurs as a result of histoincompatibility between the host and the donor; it is the major obstacle in successful transplantation of tissues. Current treatment for transplantation rejection, as for autoimmune disease, involves the use of a variety of immunosuppressant drugs and corticosteroid treatment.

Kjellin and Sandstrom, Acta Chemica Scandinavica, 23: 2879–2887 and 2888–2899 (1969), discloses a series of tautomeric cyclic thiones, i.e., oxazoline-, thiazoline-, and imidazoline-2-(3)-thiones, having methyl and phenyl groups in the 4 and 5 positions. The compounds were used for a study of thione-thiol equilibria. No pharmaceutical, or any other utility, is disclosed or suggested for these compounds.

U.S. Pat. No. 3,641,049, Sandstrom et al., issued Feb. 8, 1972, discloses N,N'-dialkyl4-phenylimidazoline-2-thiones, particularly 1,3-dimethyl4-phenylimidazoline-2-thione, for use as an antidepressant agent. The dimethyl compound is also said to exhibit antiviral properties against herpes simplex and vaccinia viruses.

U.S. Pat. No. Re. 24,505, Rimington et al., reissued Jul. 22, 1958, discloses a group of imidazole compounds useful as anti-thyroid compounds.

U.S. Pat. No. 3,505,350, Doebel et al., issued Apr. 7, 1970, discloses a group of substituted 2-mercaptoimidazole derivatives which are said to be effective as anti-inflammatory agents. Illustrative compounds include 1-(4-fluorophenyl)-5-methyl-2-mercaptoimidazole and 1-methyl-5-phenyl-2-mercaptoimidazole.

U.S. Pat. No. 3,390,150, Henry, issued Jun. 25, 1968, is representative of a group of patents which disclose nitroimidazole derivatives which possess antischistosomal and antitrichomonal activity.

U.S. Pat. No. 5,051,441, Matsumoto et al., issued Sep. 24, 1991, discloses diphenyl imidazoline derivatives which are said to act as immunomodulators, showing efficiency in the treatment of rheumatoid arthritis, multiple sclerosis, systemic lupus, and rheumatic fever.

U.S. Pat. No. 4,073,905, Kummer, et al., issued Feb. 14, 1978, discloses 2-amino4-phenyl-2-imidazolines, which are said to be useful for treating hypertension.

U.S. Pat. No. 5,202,312, Matsumoto et al., issued Apr. 13, 1993, discloses imidazoline-containing peptides which are said to have immunomodulatory activity.

PCT Application WO 92/04033, Faustman, et al., identifies a method for inhibiting rejection of transplanted tissue in a recipient animal by modifying, eliminating, or masking the antigens present on the surface of the transplanted tissue. Specifically, this application suggests modifying, masking or eliminating human leukocyte antigen (HLA) Class I antigens. The preferred masking or modifying drugs are F(ab)' fragments of antibodies directed against HLA-Class I antigens. However, the effectiveness of such a therapy will be limited by the hosts' immune response to the antibody serving as the masking or modifying agent. In addition, in organ transplantation, this treatment would not affect all of the cells because of the perfusion limitations of the masking antibodies. Faustman, et al. contends that fragments or whole viruses can be transfected into donor cells, prior to transplantation into the host, to suppress HLA Class I expression. However, use of whole or fragments of virus presents potential complications to the recipient of such transplanted tissue since some viruses, SV40 in particular, can increase Class I expression (Singer and Maguire, Crit. Rev. Immunol., 10:235–237 (1991), see particularly Table 2).

British Patent 592,453, Durant, et al., identifies isothiourea compositions that may be useful in the treatment of autoimmune diseases in host versus graft (HVG) disease and assays for assessing the immunosuppressive capabilities of these compounds. However, this patent does not describe methimazole or the suppression of MHC Class I molecules in the treatment of autoimmune diseases. No tautomeric cyclic thiones are disclosed or discussed.

Several autoimmune diseases have been treated with methimazole with potential success. In one study, MMI was deemed as good as cyclosporin in treating juvenile diabetes (W. Waldhausl, et al., Akt. Endokrin. Stoffw. 8:119 (1987), and psoriasis has also been treated with MMI.

U.S. Pat. No. 5,556,754, Singer, et al. (which is equivalent to PCT Application WO 94/28897), issued Sep. 17, 1996, describes a method for treating autoimmune diseases using methimazole, methimazole derivatives and methinazole analogs. The terms "methimazole derivative" and "methimazole analog" are not defined or exemplified anywhere in the patent.

U.S. Pat. No. 5,310,742, Elias, issued May 10, 1994, describes the use of thioureylene compounds to treat psoriasis and autoimmune diseases. Propylthiouracil, methimazole, and thiabendazole are the only specific compounds disclosed in the patent. Examples show the use of methimazole to treat psoriasis in humans and the use of thioureylene to treat rheumatoid arthritis, lupus and transplant rejection. No methimazole analogs or derivatives are disclosed or discussed. No tautomeric cyclic thiones are disclosed or discussed.

U.S. Pat. No. 4,148,885, Renoux, et al., issued Apr. 10, 1979, describes the use of specific low molecular weight sulfur-containing compounds as immunostimulants. Methimazole, thioguanine and thiouracil are among the compounds specified. No methimazole analogs or derivatives are disclosed or discussed. No tautomeric cyclic thiones are disclosed or discussed.

U.S. Pat. No. 5,010,092, Elfarra, issued Apr. 23, 1991, describes a method of reducing the nephrotoxicity of certain drugs via the coadministration of methimazole or carbimazole (which is taught to be the pro-drug of methimazole) together with the nephrotoxic drug. No methimazole analogs or derivatives are discussed in this patent. No tautomeric cyclic thiones are disclosed or discussed.

U.S. Pat. No. 5,578,645, Askanazi, et al., issued Nov. 26, 1996, describes a method for minimizing the side effects associated with traditional analgesics. This is accomplished via the administration of a mixture of specific branched amino acids together with the analgesic compound. Methimazole is disclosed, in the background section of this patent, as a non-steroidal anti-inflammatory drug which may provide some of the side effects which this invention is said to address. No tautomeric cyclic thiones are disclosed or discussed.

U.S. Pat. No. 5,587,369, Daynes, et al., issued Dec. 24, 1996, describes a method for preventing or reducing ischemia following injury. This is accomplished by introducing dehydroepiandrosterone (DHEA), DHEA derivatives or DHEA congeners to a patient as soon as possible after the injury. The background section of this patent teaches that methimazole is a thromboxane inhibitor which has been shown to prevent vascular changes in burn wounds.

The U.S.P. Dictionary (US Pharmacopeia, Rockville, Md., 1996) includes methimazole (CAS-60-56-0) and describes it as a thyroid inhibitor.

Methimazole, therefore, is known in the art for a variety of pharmaceutical utilities: for the treatment of psoriasis (Elias), as an immunostimulant (Renoux, et al.), for the reduction of nephrotoxicity of certain drugs (Elfarra), for the minimization of side effects found with certain analgesics (Oskinasi, et al), as a thyroid inhibitor (USP Dictionary), and as a thromboxane inhibitor (Daynes, et al.). It is also taught in the Singer, et al. patent as being useful in the treatment of autoimmune diseases, such as rheumatoid arthritis and systemic lupus. While the Singer, et al. patent contains general references to the use of methimazole analogs and derivatives for these therapeutic purposes, no definition of these compounds is given and no specific compounds are suggested. The pharmacological properties of tautomeric cyclic thiones are not discussed nor related to those of methimazole derivatives.

It has now been found that a specific class of methimazole derivatives and tautomeric cyclic thiones are effective in treating autoimmune diseases and suppressing the rejection of transplanted organs, and that these compounds show clear and unexpected benefits over the use of methimazole itself. In particular, these compounds: (a) are more effective in inhibiting basal and IFN-induced Class I RNA expression and in inhibiting IFN-induced Class II RNA expression than methimazole; (b) inhibit the action of IFN by acting on the CIITA/Y-box regulatory system; (c) may be significantly more soluble than methimazole, leading to significant formulation flexibility and advantages; (d) have less adverse effects on thyroid function than methimazole; (e) have an enhanced ability to bind to targets affected by MMI; and (f) exhibit therapeutic activities in vivo. These properties are unexpected based on the known properties of methimazole and particularly the tautomeric cyclic thiones.

Finally, the present invention relates to the method by which these agents inhibit interferon-gamma actions, specifically those related to increase MHC Class I and MHC Class II expression and mediation of pro-inflammatory processes, and more specifically those processes related to the induction of autoimmune disease and/or transplant rejection.

SUMMARY OF THE INVENTION

The present invention relates to pharmaceutical compositions comprising a safe and effective amount of an active compound selected from

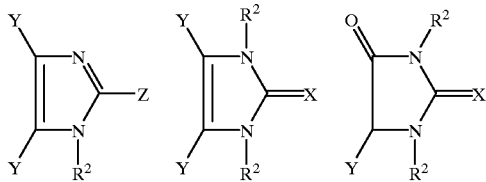

wherein Y is H, $C_1$-$C_4$ alkyl, $C_1$-$C_4$ substituted alkyl, —$NO_2$, or the phenyl moiety

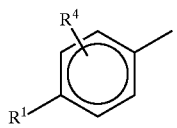

wherein no more than one Y group in said active compound may be the phenyl moiety; $R^1$ is selected from H, —OH, halogens (F, Cl, Br or I), $C_1$-$C_4$ alkyl, $C_1$-$C_4$ substituted alkyl, $C_1$-$C_4$ ester or $C_1$-$C_4$ substituted ester; $R^2$ is selected from H, $C_1$-$C_4$ alkyl or $C_1$-$C_4$ substituted alkyl; $R^3$ is selected from H, $C_1$-$C_4$ alkyl, $C_1$-$C_4$ substituted alkyl or —$CH_2$Ph (wherein Ph is phenyl); $R^4$ is selected from H, $C_1$-$C_4$ alkyl or $C_1$-$C_4$ substituted alkyl; X is selected from S or O; Z is selected from —$SR^3$, —$OR^3$, S(O)$R^3$ or $C_1$-$C_4$ alkyl; and wherein at least two of the $R^2$ and $R^3$ groups on said compound are $C_1$-$C_4$ alkyl when Y is not a phenyl moiety, and at least one Y is —$NO_2$ when Z is alkyl; together with a pharmaceutically-acceptable carrier.

Preferred compounds for use in these pharmaceutical compositions have the forumlae

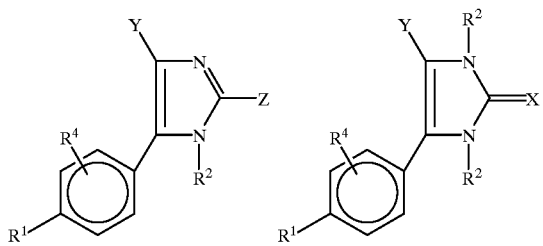

wherein Y is selected from H and $C_1$-$C_4$ alkyl or $C_1$-$C_4$ substituted alkyl; $R^1$ is selected from H, —OH, halogens (F, Cl, Br, or I), or $C_1$-$C_4$ alkyl, $C_1$-$C_4$ substituted alkyl, $C_1$-$C_4$ ester or $C_1$-$C_4$ substituted ester; $R^2$ is selected from H or $C_1$-$C_4$ alkyl or $C_1$-$C_4$ substituted alkyl; $R^3$ is selected from H, $C_1$-$C_4$ alkyl, $C_1$-$C_4$ substituted alkyl, or —$CH_2$Ph; $R^4$ is selected from H, $C_1$-$C_4$ alkyl or $C_1$-$C_4$ substituted alkyl; X is selected from S or O; and Z is selected from —$SR^3$ or —$OR^3$.

Particularly preferred compounds are those which have the formulae

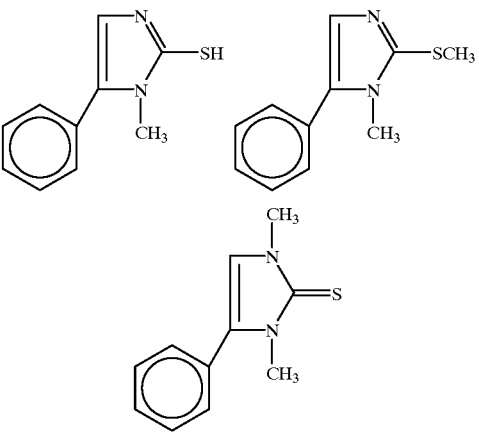

Preferred compounds also include those of the formulae:

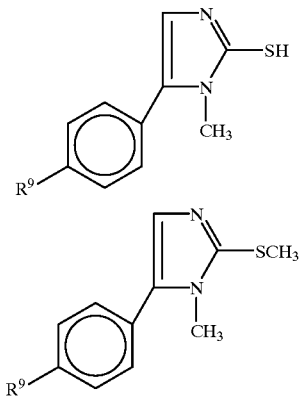

-continued

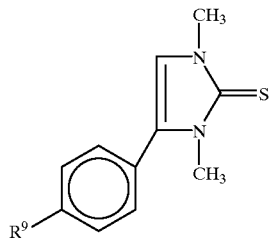

wherein $R^9$ is selected from —OH, —M and $MCH_2COO$—; and M is selected from F, Cl, Br and I.

The present invention also relates to the method of treating autoimmune diseases or transplantation rejection in a patient in need of such treatment by the administration of a safe and effective amount of the active compounds and pharmaceutical compositions described above.

The present invention also relates to in vivo assay methods which permit high efficiency screening of the effects of compounds on the expression of MHC Class I and Class II proteins.

Finally, the present invention relates to the method by which the compounds defined herein inhibit gamma interferon actions to increase MHC class I or class II expression. Gamma interferon has been linked to expression of immune disease.

As used herein, all ratios, fractions and percentages are "by weight", unless otherwise specified.

BRIEF DESCRIPTION OF THE DRAWINGS

FIG. 1. Diagrammatic representation of the upstream silencer/enhancer region of the MHC Class I PD1 gene (Panel A), the downstream silencer region of the Class I PD1 gene (Panel B), and the regulatory region of the HLA-DRα MHC Class II promoter (Panel C).

FIG. 2. Effect of methimazole and several of the active compounds used herein on formation of protein/DNA silencer complexes with Fragment 140 (−770 to −636 bp) of the MHC (Class I) 5'-flanking region, which contains within it the upstream silencer/enhancer which controls constitutive MHC class I expression in different tissues.

FIG. 3. Sequence of MHC Class I gene between −250 bp and the start of translation.

FIG. 4. Effect of treating FRTL-5 cells with MMI or a representative compound studied herein, compound 8 (see Table 1), on the formation of protein/DNA complexes with radiolabeled Fragment 127 (see FIG. 1) of the MHC 5'-flanking region, −127 to +1 bp, as a function of time.

FIG. 5. Nucleotide sequence of the 176 bp 5'-flanking region of the −176 bp HLA-DRα-CAT construct used in the experiments herein.

FIG. 6. Electrophoretic mobility shift analysis (EMSA) of the ability of a $^{32}P$-radiolabeled DRα-5'-flanking region probe to form protein/DNA complexes with extracts from FRTL-5 cells maintained with and without TSH and treated or not with γ-IFN.

FIG. 7. Effect of MMI on the ability of γ-IFN to increase the formation of protein/DNA complexes with the $^{32}P$-radiolabeled DRα-5'-flanking region probe.

FIG. 8. Effect of 1 mM MMI or 1 mM concentrations of representative compounds studied herein on the ability of γ-IFN to increase the formation of protein/DNA complexes with the $^{32}P$-radiolabeled DRα-5'-flanking region probe.

FIG. 9. Effect of MMI and/or TSH on exogenous class I promoter activity in FRTL-5 cells.

FIG. 10. Effect of MMI and TSH on the promoter activity of CAT chimeras of 5'-deletion mutants of the swine class I promoter in FRTL-5 cells.

FIG. 11. Effect of γ-interferon (IFN) on class II expression in FRTL-5 thyroid cells measured using the −176 bp HLA-DRα-CAT construct and 5'-deletions thereof (A) or the −176 bp DRα-CAT construct having mutations with the S, $X_1$, $X_2$, and Y boxes (B).

FIG. 12. Effect of γ-IFN and MMI on MHC class II antigen expression in FRTL-5 cells.

FIG. 13. Effect of γ-IFN on class II expression in FRTL-5 thyroid cells as a function of γ-IFN concentration (A) and in the presence of MMI (B).

FIG. 14. Effect of MMI on γ-IFN-increased class II expression in FRTL-5 thyroid cells as a function of MMI concentration.

FIG. 15. Effect of MMI, compound 10 (5-phenylmethimazole) and compound 3(2-mercaptoimidazole) on immune complexes in the kidneys of $(NZBxNZW)F_1$ mice.

FIG. 16. Ability of MMI or compounds 10 (5-phenylmethimazole), 7 (5-methylmethimazole), 8 (N-methylmethimazole) or 11 (1-methyl-2-thiomethyl-5(4) nitroimidazole) to reverse the ability of γ-IFN to reduce Y box RNA levels.

FIG. 17. Model of the development of autoimmune disease and the effect of the MMI, MMI derivatives or tautomeric cyclic thiones on the development process.

DETAILED DESCRIPTION OF THE INVENTION

The present invention relates to pharmaceutical compositions which may be used to treat autoimmune diseases and to suppress the rejection of transplanted tissue. The methods of treating autoimmune diseases and of suppressing rejection of transplanted tissue utilizing these pharmaceutical compositions are also covered, as are specific methimazole derivatives and tautomeric cyclic thione compounds which may be used to make these pharmaceutical compositions. As used herein, the following terms shall have the definitions given below.

The phrase "safe and effective amount" means a sufficient amount of pharmaceutically active compound to desirably affect the treatment of autoimmune diseases or to suppress the rejection of transplanted tissue, at a reasonable benefit/risk ratio attendant with any medical treatment. Within the scope of sound medical judgement, the required dosage of a pharmaceutically active agent or of the pharmaceutical composition containing that active agent will vary with the severity of the condition being treated, the duration of the treatment, the nature of adjunct treatment, the age and physical condition of the patient, the specific active compound employed, and like considerations discussed more fully hereinafter. In this regard it should be noted that the use of MMI at high doses can induce side effects, such as aplastic anemia, agranulocytosis, hepatic dysfunction and dermatitis, in certain patients. In arriving at the "safe and effective amount" for a particular compound, these risks must be taken into consideration, as well as the fact that the compounds described herein provide pharmaceutical activity at lower dosage levels than conventional methimazole compounds.

"Pharmaceutically-acceptable" shall mean that the pharmaceutically active compound and other ingredients used in the pharmaceutical compositions and methods defined herein are suitable for use in contact with the tissues of humans and lower animals without undue toxicity, irritation, allergic response, and the like, commensurate with a reasonable benefit/risk ratio.

The term "administration" of the pharmaceutically active compounds and the pharmaceutical compositions defined herein includes systemic use, as by injection (especially parenterally), intravenous infusion, suppositories and oral administration thereof, as well as topical application of the compounds and compositions. Oral administration is particularly preferred in the present invention.

The term "comprising", as used herein, means that various other compatible drugs and medicaments, as well as inert ingredients, can be conjointly employed in the pharmaceutical compositions and methods of this invention, as long as the defined pharmaceutically active compounds and carriers are used in the manner disclosed. The term "comprising" thus encompasses and includes the more restrictive terms "consisting of" and "consisting essentially of".

The term "patient", as used herein, is intended to encompass any mammal, animal or human, which may benefit from treatment with the compounds, compositions and methods of the present invention.

By "compatible" herein is meant that the components of the compositions which comprise the present invention are capable of being comingled without interacting in a manner which would substantially decrease the efficacy of the pharmaceutically active compound under ordinary use conditions.

The pharmaceutical compositions of the present invention comprise specifically-defined methimazole derivatives and tautomeric cyclic thiones, used in a safe and effective amount, together with a pharmaceutically-acceptable carrier.

The methimazole derivatives used in the compositions of the present invention are those having the following structural formulae:

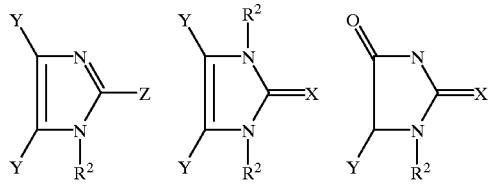

In these formulae, Y is selected from H, $C_1$–$C_4$ alkyl $C_1$–$C_4$ substituted alkyl, —$NO_2$, and the phenyl moiety

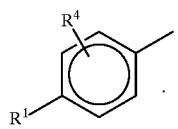

Y is preferably H, the phenyl moiety or —$NO_2$, and is most preferably H or the phenyl moiety

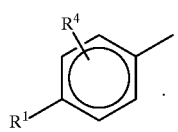

In the defined compounds, no more than one Y group may be the phenyl moiety. $R^1$ is selected from H, —OH, halogens (F, Cl, Br and I), $C_1$–$C_4$ alkyl, $C_1$–$C_4$ substituted alkyl, $C_1$–$C_4$ester and $C_1$–$C_4$ substituted ester; preferably $R^1$ is H, —OH, halogen, —OOC $CH_2$M (where M is H or a halogen); and is most preferably H. $R^2$ is selected from H, $C_1$–$C_4$ alkyl and $C_1$–$C_4$ substituted alkyl; preferably one or both of the $R^2$ groups is methyl. As used herein, "substituted alkyl" or "substituted ester" is intended to include alkyl, aryl or ester groups which are substituted in one or more places with hydroxyl or alkoxyl groups, carboxyl groups, halogens, nitro groups, amino or acylamino groups, and mixtures of those moieties. Preferred "substituted alkyl" groups are $C_1$–$C_4$ hydroxyl or alkoxyl groups, as well as groups substituted with halogens. The $R^3$ groups in the above formulae are selected from H, $C_1$–$C_4$ alkyl, $C_1$–$C_4$ substituted alkyl and —$CH_2$Ph (wherein Ph is phenyl); in preferred compounds, $R^3$ is H or $C_1$–$C_4$ alkyl; most preferably $R^3$ is $C_1$–$C_4$ alkyl, particularly methyl. $R^4$ is selected from H, $C_1$–$C_4$ alkyl and $C_1$–$C_4$ substituted alkyl, and preferably is H. X may be S or O, and is preferably S. Finally, Z is selected from $C_1$–$C_4$ alkyl, —$SR^3$, —$S(O)R^3$ and —$OR^3$, is preferably —$SR^3$, —$OR^3$, and —$S(O)R^3$; most preferably —$SR^3$ and —$OR^3$; and particularly —$SR^3$. In the above formulae, at least two of the $R^2$ and $R^3$ groups on the compound must be $C_1$–$C_4$ alkyl when Y is not a phenyl moiety. Further, at least one of the Y groups should be —$NO_2$, when Z is $C_1$–$C_4$ alkyl.

Compounds useful in the present invention include the tautomeric cyclic thiones, disclosed in Kjellin and Sandstrom, Acta Chemica Scandanavica 23: 2879–2887 (1969), incorporated herein by reference, having the formulae

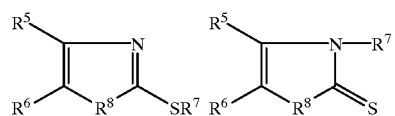

wherein $R^5$, $R^6$=$CH_3$, $CH_3$; Ph, H; H, Ph $R^7$=H, $CH_3$ $R^8$=O, S, NH, $NCH_3$ Preferred compounds for use in the compositions of the present invention include those having the formulae:

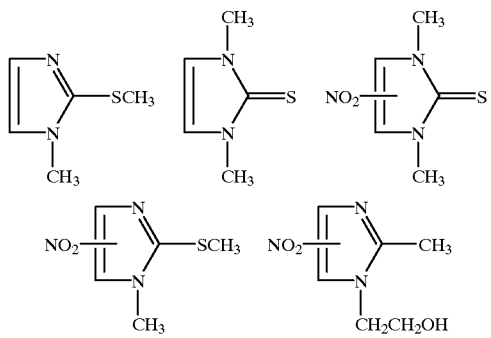

Another group of preferred compositions include those having the formulae:

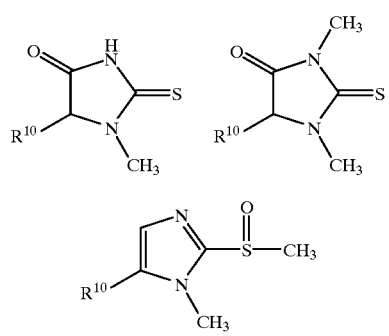

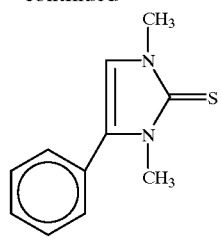

Other preferred compounds include:

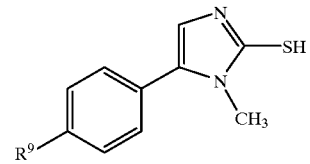

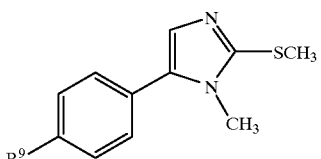

wherein $R^{10}$ is selected from H, $NO_2$, Ph, 4-HOPh and 4-m-Ph (wherein m is F, Cl, Br, or I).

A particularly preferred subset of the pharmaceutical compounds defined herein are those wherein one of the Y groups is the phenyl moiety defined above. These compounds have the following formulae:

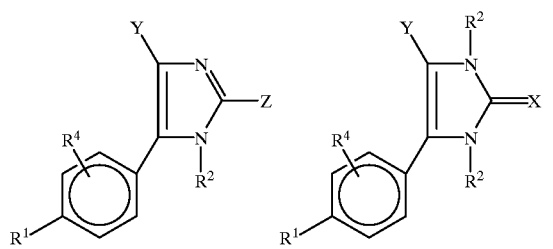

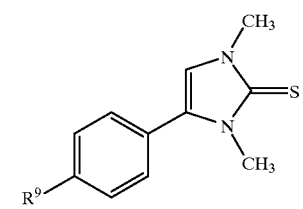

wherein $R^9$ is selected from —OH, —M and —$OOCCH_2M$; and M is selected from F, Cl, Br and I.

Most preferred is the compound having the structure given below. This compound has demonstrated an unexpectedly high activity in terms of suppressing the expression of MHC Class I and Class II proteins. Further, this compound has shown a different effect on thyroid gene expression, i.e., thyroglobin, when compared to MMI. This suggests that it may be used to treat autoimmune diseases and even Graves' Disease, without requiring thyroid hormone supplementation.

In these compounds, Y is selected from H, $C_1$–$C_4$ alkyl and $C_1$–$C_4$ substituted alkyl, and is preferably H. $R^1$ is selected from H, —OH, halogens (F, Cl, Br and I), $C_1$–$C_4$ alkyl, $C_1$–$C_4$ substituted alkyl, $C_1$–$C_4$ ester, and $C_1$–$C_4$ substituted ester, and is preferably H, —OH, halogen, —$OOCCH_2M$ (where) M is H or a halogen), and is not preferably H. $R^2$ is selected from H, $C_1$–$C_4$ alkyl and $C_1$–$C_4$ substituted alkyl, and it is preferred that at least one of the $R^2$ groups be methyl. $R^3$ is selected from H, $C_1$–$C_4$ alkyl, $C_1$–$C_4$ substituted alkyl, and —$CH_2Ph$; preferred $R^3$ moieties are H and methyl. $R^4$ is selected from H, $C_1$–$C_4$ alkyl and $C_1$–$C_4$ substituted alkyl, and is preferably H. X is selected from S and O, and is preferably S. Finally, the Z moiety is selected from —$SR^3$ and —$OR^3$, and is preferably —$SR^3$. Particularly preferred compounds are those having the structural formulae

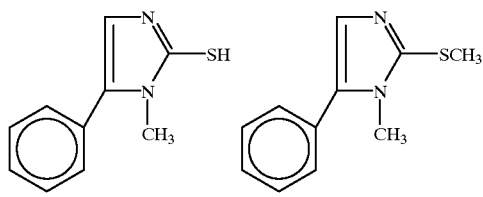

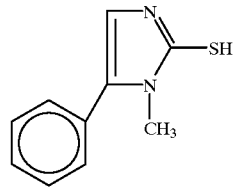

5-phenylmethimazole

Mixtures of the pharmaceutically active compounds defined herein may also be used.

The methimazole derivatives and tautomeric cyclic thiones described above can be synthesized using techniques well known to those skilled in the art. For example, the synthesis of several tautomeric cyclic thiones is described in Kjellin and Sandstrom, Acta Chemica Scandanavica 23: 2879≈2887 (1969), incorporated herein by reference.

A representative methimazole derivative may be synthesized using the following procedure. Appropriately substituted analogs of acetaldehyde are brominated in the 2-position by treatment with bromine and UV light, followed by formation of the corresponding diethylacetal using absolute ethanol. The bromine is then displaced from this compound by treatment with anhydrous methylamine, or other suitable amine, in a sealed tube at about 120° for up to about 16 hours. Reaction of the resulting aminoacetal with potassium thiocyanate in the presence of hydrochloric acid, at steam bath temperatures overnight, provides the methimazole analogs.

The pharmaceutical compositions of the present invention comprise a safe and effective amount of one or more of the methimazole derivatives or tautomeric cyclic thione compounds (i.e., the active compounds). Preferred compositions contain from about 0.01 % to about 25 % of the active compounds, with most preferred compositions containing from about 0.1% to about 10% of the active compounds. The pharmaceutical compositions of the present invention may be administered in any way conventionally known, for example, intraperitoneally, intravenously, intramuscularly, or topically, although oral administration is preferred. Preferred compositions are in unit dosage form, i.e., pharmaceutical compositions which are available in a pre-measured form suitable for single dosage administration without requiring that the individual dosage be measured out by the user, for example, pills, tablets or ampules.

The pharmaceutical compositions of the present invention additionally include a pharmaceutically-acceptable carrier compatible with the methimazole derivatives or tautomeric cyclic thiones described above. In addition to the pharmaceutically-acceptable carrier, the pharmaceutical compositions may contain, at their art accepted levels, additional compatible ingredients, such as additional pharmaceutical actives, excipients, formulational aids (e.g., tabletting aids), colorants, flavorants, preservatives, and other materials well known to those skilled in the art.

As used herein, the term "pharmaceutical carrier" denotes a solid or liquid filler, diluent or encapsulating substance. These materials are well known to those skilled in the pharmaceutical arts. Some examples of the substances which can serve as pharmaceutical carriers are sugars, such as lactose, glucose, and sucrose; starches, such as corn starch and potato starch; cellulose and its derivatives, such as sodium carboxymethyl cellulose, ethyl cellulose, and cellulose acetate; powdered tragacanth; malt; gelatin; talc; stearic acid; magnesium stearate; calcium sulfate; vegetable oils, such as peanut oil, cottonseed oil, sesame oil, olive oil, corn oil and oil of theobroma; polyols, such as propylene glycol, glycerine, sorbitol, mannitol, and polyethylene glycol; agar; alginic acid; pyrogen-free water; isotonic saline; and phosphate buffer solutions, as well as other non-toxic compatible substances used in pharmaceutical formulations. Wetting agents and lubricants, such as sodium lauryl sulfate, as well as coloring agents, flavoring agents, tableting agents, and preservatives, can also be present. Formulation of the components into pharmaceutical compositions is done using conventional techniques.

The pharmaceutical carrier employed in conjunction with the pharmaceutical compositions of the present invention is used at a concentration sufficient to provide a practical size-to-dosage relationship. Preferably, the pharmaceutical carrier comprises from about 75% to about 99.99%, preferably from about 90% to about 99.9%, by weight of the total pharmaceutical composition. The methimazole derivatives or tautomeric cyclic thiones defined in the present application may surprisingly be more soluble than methimazole in conventional carrier materials. This provides significant benefits in allowing greater flexibility in the formulation of pharmaceutical compositions containing those methimazole derivatives, and may allow the use of significantly lower doses of the active compound.

The present invention also provides a method for treating autoimmune diseases and for preventing or treating rejection of tissue in a transplant recipient. More specifically, this invention relates to methods for administering to a mammal in need of such treatment a drug or drugs, as defined herein, capable of suppressing expression of MHC Class I or Class II molecules.

Examples of autoimmune diseases that can be treated using this method include, but are not limited to, rheumatoid arthritis, psoriasis, juvenile or type I diabetes, primary idiopathic myxedema, systemic lupus erythematosus, DeQuervains thyroiditis, thyroiditis, autoimmune asthma, myasthenia gravis, scleroderma, chronic hepatitis, Addison's disease, hypogonadism, pernicious anemia, vitiligo, alopecia areata, Coeliac disease, autoimmune enteropathy syndrome, idiopathic thrombocytic purpura, acquired splenic atrophy, idiopathic diabetes insipidus, infertility due to antispermatazoan antibodies, sudden hearing loss, sensoneural hearing loss, Sjogren's syndrome, polymyositis, autoimmune demyelinating diseases such as multiple sclerosis, transverse myelitis, ataxic sclerosis, pemphigus, progressive systemic sclerosis, dermatomyositis, polyarteritis nodosa, hemolytic anemia, glomerular nephritis and idiopathic facial paralysis. In its broadest aspects, methimazole derivatives of the present invention are administered in a dosage range of from about 0.001 to about 100 milligrams, preferably from about 0.05 to about 50 milligrams, per day. The pharmaceutical compositions of the present invention are administered such that appropriate levels of pharmaceutical active are achieved in the bloodstream. The precise dosage level required in a given case will depend upon, for example, the particular methimazole derivative used, the nature of the disease being treated, and the size, weight, age and physical condition of the patient.

In a preferred embodiment, an active compound of the present invention, for example 5-phenylmethimazole, is administered to a mammal, preferably a human, afflicted with an autoimmune disease. Suitable therapeutic amounts of the methimazole derivatives are in the range of from about 0.05 to about 20 milligrams per day. A preferred dosage is from about 0.05 to about 10 milligrams per day. The dosage can be administered daily, in approximately equally divided amounts at 8 hour intervals or with breakfast, lunch and dinner. Therapy can be continuous, for example, for periods up to one year or longer. Alternatively, therapy can be tapered, for example, starting at a higher dosage level and tapering to a lower daily dosage level within four to ten weeks. Thyroid hormone (thyroxin $T_4$ or triiodothyronine $T_3$) or thyroid stimulating hormone (TSH) levels in the individual receiving such treatment may, for some compounds, be an index of therapeutic effectiveness. It is understood by one skilled in the art that the dosage administered to a mammal afflicted with an autoimmune disease may vary depending on the mammal's age, severity of the disease and response to the course of treatment. One skilled in the art will know the clinical parameters to evaluate to determine proper dosage for an afflicted mammal.

In another preferred embodiment, an active compound described herein is administered to a mammal, preferably a human, afflicted with systemic lupus erythematosus (SLE). A preferred therapeutic amount is in the range of from about 0.05 to about 20 milligrams per day, administered over two to twelve months, but can be administered in discontinuous treatment periods of similar length over a five-year period or for as long as necessary. Alternatively, the compositions of the present invention may be administered in conjunction with the current therapies for SLE, hydrocortisone and cytotoxic drugs, to suppress the disease. SLE patients with breast cancer cannot be readily treated with radiation therapy since they are already immunosuppressed by the current conventional treatment for SLE. Also SLE may be associated with unusual sensitivity to radiation complications and therefore radiation therapy exacerbates the disease. It is anticipated, therefore, that the use of the methimazole derivatives and tautomeric cyclic thiones of the present invention to treat SLE individuals with breast cancer will allow radiation therapy to be administered to such individuals without radiation complications or exacerbation of their condition.

In another embodiment, the methimazole derivatives, cyclic tautomeric thiones, and pharmaceutical compositions of the present invention are administered to a mammal, preferably a human, afflicted with type I or juvenile diabetes.

In another embodiment, the methimazole derivatives, tautomeric cyclic thiones, and pharmaceutical compositions of the present invention are administered to a mammal, preferably a human, afflicted with an autoimmune disease associated with the development of thyroid autoantibodies in the sera of these animals.

In yet another embodiment, the methimazole derivatives, tautomeric cyclic thiones, and pharmaceutical compositions of the present invention are administered to a mammal, preferably a human, afflicted with an autoimmune disease characterized by the development of receptor autoantibodies. For example, autoimmune asthma is associated with P-adrenergic receptor autoantibodies. Treatment with the compositions of the present invention will alleviate the disease. Another example of such an autoimmune disease is myasthenia gravis. Myasthenia gravis is associated with acetylcholine receptor autoantibodies. Individuals afflicted with myasthenia gravis have a higher frequency of thyroid autoimmunity. Because of the structural and functional relationship between the TSH and acetylcholine receptors, treatment of an animal, preferably a human, afflicted with myasthenia gravis with a drug able to suppress both MHC Class I and Class II, such as the methimazole derivatives or tautomeric cyclic thiones of the present invention, will help suppress the disease.

The method of this invention is also suitable for preventing or treating rejection of a transplanted tissue in a recipient mammal, preferably a human.

Examples of tissues which may be transplanted include, but are not limited to, heart, lung, kidney, bone marrow, skin, pancreatic islet cells, thyroid, liver and all endocrine tissues, neural tissue, muscle, fibroblast, and adipocytes.

As an example of the prevention of rejection of transplanted tissue, pancreatic islet cells are isolated from a donor and treated with a methimazole derivative or tautomeric cyclic thione of the present invention prior to transplantation into a recipient suffering from diabetes. Diabetes is caused by loss of islet cells as a result of autoimmune disease. Transplantation of islet cells will correct such a deficiency. Islet cells may be treated with from about 0.05 to about 20 milligrams of active compound per day, for example, in the form of an aqueous solution for from about 24 to about 72 hours or longer as necessary to suppress expression of MHC Class I molecules on the islet cells. After transplantation, the recipient may be further treated with a methimazole derivative or tautomeric cyclic thione together with hydrocortisone and/or other immunosuppressive agents.

The present invention also relates to an in vitro assay for assessing the ability of a drug to suppress expression of MHC Class I and MHC Class II proteins by measuring the activity of a reporter gene operably linked downstream of a MHC Class I and MHC Class II promoter and its regulatory sequences. The reporter gene operably linked to an MHC Class I and MHC Class II promoter and its regulator sequence is introduced into mammalian cells, said mammalian cells are treated with the candidate drug and the activity of the reporter gene in lysates from treated and untreated mammalian cells is measured. A decrease of activity of the reporter gene in cell lysates from treated versus nontreated cells is predictive of the usefulness of the candidate drug in suppressing MHC Class I and MHC Class II expression and, in turn, suppressing an autoimmune disease or preventing transplant rejection.

Preferred regulatory sequences that may be operably linked to the reporter gene are sequences corresponding to the regulatory region of the class I gene, −1 Kb to +1 bp; upstream silencer/enhancer region of the MHC Class I, PD1 gene, −769 to −673 bp (FIG. 1A); the downstream regulatory region of the PD1 gene, −203 or −127 to −1 bp; the downstream silencer region of the PD1 gene, −127 to −80 bp (FIG. 1B); and the regulatory region of the MHC Class II gene containing the S,Y,$X_1$ and $X_2$ boxes, −137 to −50 bp (FIG. 1C). These sequences are shown in FIG. 1, with their cognate promoters. It will be understood by one skilled in the art that sequentially and functionally homologous regions found in the regulatory and promoter domains of other Class I and Class II genes may also be used. Examples of reporter genes include, but are not limited to, the chloramphenicol acetyltransferase (CAT) gene, the β-galactosidase gene, the luciferase gene and human growth hormone (hGH) (Sambrook, J. et al., Molecular Cloning: A Laboratory Manual, Vol. 2, $2^{nd}$ ed.; Cold Spring Harbor Press, NY (1989); Ausubel, F. et al. in "Current Protocols in Molecular Biology: Supplement 14, section 9.6 (1987); John Wiley and Sons, New York (1990)). Examples of mammalian cells that can be used in this in vitro assay include, but are not limited to, mammalian cell thyrocytes, hepatocytes, neural tissue, muscle, fibroblasts, adipocytes and HELA cells. The means by which the regulatory sequence operably linked to the reporter gene may be introduced into cells are the same as those described above. In a preferred embodiment the luciferase gene is operably linked to one of the above mentioned PD1 sequences and introduced into FRTL-5 cells.

It is understood by one skilled in the art that the ability of a candidate drug to suppress expression of MHC Class I and MHC Class II molecules can also be assessed by comparing levels of cellular mRNA in mammalian cells treated with the candidate drug versus cells not treated with the candidate drug. Examples of methods for determing cellular MRNA levels include, but are not limited to, Northern blotting (Alwine, J. C. et al. Proc. Natl. Acad. Sci., 74:5350–5354 (1977)), dot and slot hybridization (Kafatos, F. C. et al. Nucleic Acids Res., 7:1541–1522 (1979)), filter hybridization (Hollander, M. C. et al. Biotechniques; 9:174–179 (1990)), RNase protection (Sambrook, J. et al. in "Molecular Cloning, A Laboratory Manual", Cold Spring Harbor Press, Plainview, N.Y. (1989)), polymerase chain reaction (Watson, J. D. et al.) in "Recombinant DNA" Second Edition, W.H. Freeman and Company, New York (1992)) and nuclear run-off assays (Ausubel, F. et al. in "Current Protocols in Molecular Biology" Supplement 9 (1990); John Wiley and Sons, New York (1990)).

The following examples are intended to illustrate the pharmaceutically active compounds, pharmaceutical compositions and methods of treatment of the present invention, but are not intended to be limiting thereof.

EXAMPLE 1

Preparation of 5-phenylmethimazole

The preferred compound 5-phenylmethimazole is synthesized as follows:

Step 1—Synthesis of 2-Bromophenylacetaldehyde diethylacetal

The bromination of phenylacetaldehyde may be performed according to the method of P. Duhamel, L. Duhamel and J-Y Valnot, Bull. Soc. Chim. Fr. 1973, 1465.

120 g (1 mol, 117 mL) of phenylacetaldehyde is cooled in a three-neck flask to 20° C. using dry ice/$CCl_4$. 160 g (1 mol) of bromine is added dropwise with vigorous stirring and cooling. Following addition, the reaction solution is transferred to a 2L round bottom flask and approximately 1.5 liters of absolute ethanol added. This solution is stirred overnight at room temperature. The solution is evaporated in vacuo, and extracted with a saturated solution of $Na_2CO_3$. The crude product is dried over $K_2CO_3$ and filtered to yield 145.34 g. The final product is distilled at 94° C. under 50 pressure to yield 86.93 g (46%) of pure material.

$^1$H-NMR ($CDCl_3$): δ 1.05 (3H t), 1.30 (3H t), 3.3–3.9 (5H m), 4.91 (2H dd), 7.32–7.48 (5H m).

Step 2—Synthesis of 2-Methylaminophenylacetaldehyde diethylacetal

This material may be synthesized using the method of Jones, et al., J. Am. Chem. Soc., 1949, 71:4000.

A 200 mL heavy walled glass reaction vessel is cooled in dry ice/acetone and charged with approximately 25 mL anhydrous methylamine. To this is added approximately 25 mL (32 ) of 2-bromophenylacetaldehyde diethylacetal. The mixture is solidified in liquid nitrogen and the reaction vessel evacuated on a vacuum pump. The reaction vessel is closed and heated in an oil bath at 110° C. overnight. The reaction vessel is cooled in dry ice/acetone followed by liquid nitrogen and the methylamine vented to an aqueous solution. Crude reaction product is taken up in methanol and extracted with 1N aqueous KOH solution and dried over solid KOH. The solution is evaporated in vacuo and the crude material is purified by distillation. The product is distilled at 100° C. under 255µ of pressure. Yield of material is 89.7%.

$^1$H-NMR ($CDCl_3$): δ 0.95 (3H t), 1.24 (3H t), 2.23 (3H s), 3.23 (m), 3.49–3.54 (m), 3.60 (d), 3.7–3.9 (m), 4.41 (d), 7.26–7.40 (5H m).

Step 3—Synthesis of 5-Phenylmethimazole

This material may be synthesized using the method of R. G. Jones, J. Am. Chem. Soc., 1949, 71: 383–386.

50 g (224 mmol) of 2-methylaminophenylacetaldehyde diethylacetal is dissolved in 100 mL of 50% ethanol/water solution. To this is added, with stirring, 26.123 g (268.8 mmol) of potassium thiocyanate and 22.39 mL (268.8 mmol) of concentrated hydrochloric acid. The mixture is heated on a steam bath for four days in an open beaker. The crude reaction mixture is taken up in ethyl acetate (200 mL) and extracted with water (3×50 mL), saturated solution of $Na_2CO_3$ (3×50 ml) and a saturated solution of NaCl (3×50 mL). The solution is dried over $Na_2SO_4$, and evaporated in vacuo to yield 47.65 g of an orange-red oil. The material is taken up in benzene and chromatographed on 450 g of silica gel. The column is initially eluted with benzene followed by 10% ethyl acetate:benzene upon the appearance of product. Fractions containing product are combined into three groups. Fractions A and C are combined to yield 13.93 g and recrystallized from ethanol to yield 2.3 g. Group B is recrystallized to yield 3.9 g. Recrystallized yield 14.5%. Melting point 168–173 ° C.

$^1$H-NMR ($CDCl_3$): δ 3.59 (3H s), 6.76 (1H s), 7.42 (5H m).

Preparation of 1-methyl-5-phenyl imidazoline-2(3)-thione

See Kjellin and Sandstrom, Acta Chemica Scandinavica 23: 2879–2887 (1969).

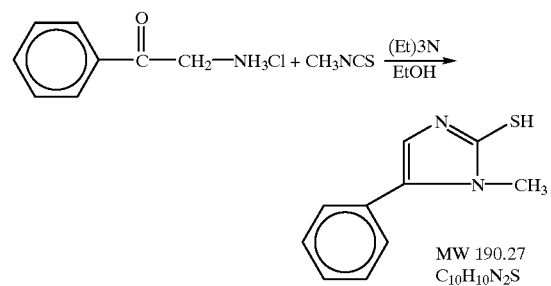

MW 190.27
$C_{10}H_{10}N_2S$

To a 1 liter r.b. flask equipped with a mechanical stirrer, addition funnel, condenser, and $N_2$ inlet is added 50 g of α-aminoacetophenone hydrochloride, 22.5 mL of methyl isothiocyanate, and 600 mL of absolute ethanol. To this mixture is added 42 mL of triethylamine. The reaction solution is heated at reflux for 1 hr.

The reaction mixture is stripped to near-dryness. To the residue is added 150 mL of water. The resulting suspension is suction filtered and 80 g of yellow solids is collected. This filter cake is slurried in 500 mL of 1N NaOH solution. The insolubles are filtered off. To the filtrate is added approximately 100 mL of 37% HCl. The resulting suspension is suction filtered and the solids recrystallized from 50 mL of a 25 % aqueous ethanol solution.

25.7 g of pale pink solids are collected, m.p. 178–179°. HPLC indicates 99.8% purity.

Elemental analysis is as follows: Found: C, 62.82; H, 5.21; N, 14.74; S, 16.63 Theory: C, 63.13; H, 5.30; N, 14.73; S, 16.86

IR, carbon NMR, and proton NMR all support the desired structure.

Preparation of 1-methyl-2-methylthio-5-phenyl-imidazole

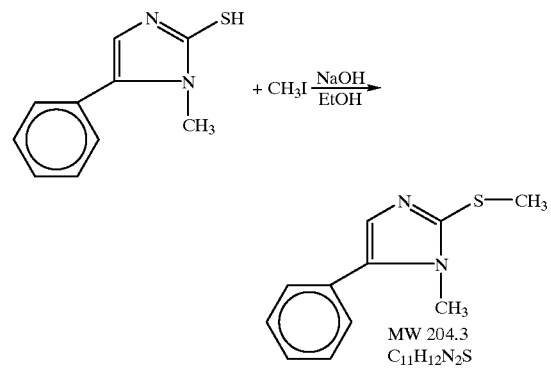

MW 204.3
$C_{11}H_{12}N_2S$

To a 1 liter r.b. flask equipped with a mechanical stirrer, condenser, thermometer, and addition funnel are added 19.1 g of 1-methyl-5-phenyl-imidazoline-2(3)-thione (Compound 10) and 335 mL of 95% ethanol. To this is added 4 g of NaOH and the mixture is stirred until a solution is realized.

To this is added 15.6 g of methyl iodide in 145 mL of 95% ethanol over 35 minutes at ambient temperature (28–30° C). The resulting mixture is stirred at ambient for 3 hrs. The resulting mixture is stripped on the rotary evaporator. Approximately 41 g of orange colored solids are collected. This is dissolved in approximately 600 mL of methylene chloride and to this is added approximately 600 mL of water. The organic layer is separated. The aqueous layer is extracted twice with methylene chloride, and the organic layers combined, dried over sodium sulfate filtered and stripped on the rotary evaporator, to afford 26.7 g of oily solids. This is suction filtered and air dried to yield 16.5 g of pale orange solids, m.p. 85–87° C. This is recrystallized (along with 0.8 g and 2.5 g of product from 2 small scale preps) from a total of 2.5 L of heptane. 10.7 g of off-white solids is collected; m.p. 87° C. HPLC indicates 99.8% purity.

Elemental analysis: Found: C, 64.70; H, 5.85; N, 13.70; S, 15.55 Theory: C, 64.66; H, 5.93; N, 13.70; S, 15.72

IR, carbon NMR, and proton NMR all give evidence for the desired product.

Preparation of 1,3-dimethyl-4(5)-phenyl-imidazoline-2(3)-thione

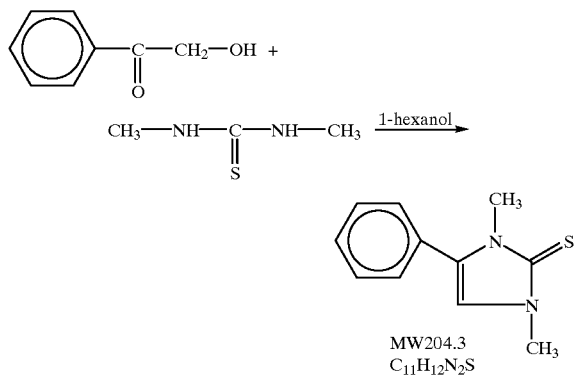

To a 100 mL r.b. flask equipped with a Dean-Stark trap, condenser, $N_2$ inlet and magnetic stirring are added 13 g of α-hydroxyacetophenone, 10 g of N,N-dimethylthiourea, and 50 mL of 1-hexanol. This is heated at reflux for approximately 3.5 hrs. Approximately 3 mL of water is collected.

Precipitation occurrs after placing the reaction mixture in the freezer for 1 hr. The resulting mixture is suction filtered. 13.2 g of solids are collected, m.p. 105° C. This (along with 10.4 g of product from another prep.) is recrystallized from approximately 150 mL of absolute ethanol. 12.5 g of white solids are collected, m.p. 126–127° C.

HPLC indicates 99.8% purity.

Elemental analysis indicates: Found: C, 64.44; H, 5.81; N, 13.70; S, 15.55 Theory: C, 64.66; H, 5.93; N, 13.71; S, 15.71

IR, carbon NMR, and proton NMR all support the desired structure.

Preparation of 4-nitro-1,3-dimethylimidazole-2-thione

While there is no report of the preparation of this compound 6 in the literature, using known nitration reactions conditions provides the desired product in reasonable yield. The starting material for this nitration, Compound 5, can be readily prepared in two steps from commercially available materials using known reaction pathways and conditions.

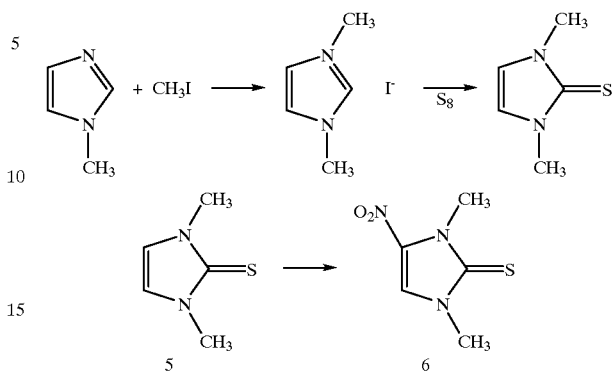

EXAMPLE 2

Assessment of the Effect of MMI-derivatives on MHC Class I and MHC Class II Expression by Gel Shift Assay Materials Purified bovine TSH was from the NIH program (NIDDK-bTSH-I-1, 30 U/mg) or was prepared as described previously (Kohn, L. D. and Winand, R. J. *J. Biol. Chem.*, 250:6503–6508 (1975)). Insulin, hydrocortisone, human transferrin, somatostatin, and glycyl-L-histidyl-L-lysine acetate were from Sigma Chemical Co. St. Louis, Mo.

Cell Culture

FRTL-5 rat thyroid cells (Kohn, L. D., et al., U.S. Pat. No. 4,609,622 (1986); Ambesi-Impiombato E S., U.S. Pat. No. 4,608,341 (1986)) are grown as described below. These cells do not proliferate in the absence of TSH, yet remain viable for prolonged periods in its absence. Their doubling time was approximately 36±6 hours; and, after 6 days in medium with no TSH (5H) and 5.0% serum, $1\times10^{-1}$ mol/L TSH elevated iodide uptake 8–10 fold and thymidine incorporation>10 fold. Cells were diploid, between their $5^{th}$ and $25^{th}$ passage in most experiments, and were routinely grown in Coon's modified F12 medium supplemented with 5 % calf serum, 1 mmol/L nonessential amino acids (GIBCO) and a mixture of 6 hormones (6H medium): TSH ($1\times10^{-10}$ M), insulin (10 µg/ml), hydrocortisone 0.4 ng/ml, human transferrin (5 µg/ml), somatostatin (10 µg/ml) and glycyl-L-histidyl-L-lysine acetate (10 ng/ml) (Kohn, L. D. et al., U.S. Pat. No. 4,609,622 (1986); Ambesi-Impiombato, E. S., U.S. Pat. No. 4,608,341 (1986)). They were passaged every 7–10 days and provided fresh media every 2 or 3 days. In individual experiments, cells were grown to near confluency in 6H medium then, in some experiments, were shifted to medium with no TSH (5H), to medium with neither TSH and or insulin (4H), or to medium with no TSH, no insulin and no hydrocortisone (3H) plus either 5% or 0.2% serum for 4–7 days before use.

Cell Extracts

Cells were grown in 6H medium with 5 % calf serum for 6–7 days to 70–80% confluence, then shifted to 5H medium with 5 % calf serum for 5 days. TSH ($1\times10^{-10}$ M), gamma-interferon (100 U/ml), MMI (5 mM), and different concentrations of MMI derivatives or tautomeric cyclic thiones (0.0001 to 10 mM) were added as appropriate for 2448 hours. Cells were then harvested and extracts were made by a modification of a method of Dignam, J., et al. *Methods in Enzymology*, 101:582–598 (1983). In brief, cells were harvested by scraping after being washed twice with cold phosphate-buffer saline (PBS). Subsequently they were pelleted, washed in cold PBS and then pelleted again. The pellet was resuspended in Dignam buffer C (20 mM Hepes buffer at pH 7.9, 1.5 mM $MgCl_2$, 0.42 M NaCl, 25% glycerol, 0.5 mM dithiotreitol (DTT), 0.5 mM phenylmethylsulfonylfluoride (PMSF), 1 μg/L leupeptin, 1 μg/L pepstatin). The final NaCl concentration was adjusted on the basis of cell pellet volume to 0.42 M and cells were lysed by repeated cycles of freezing and thawing. Extracts were then centrifuged at 10,000×g at 4° C. for 20 min. The supernatant was recovered, aliquoted and stored at −70° C.

Gel Mobility Shift Assay

Binding reactions were performed in a volume of 20 μl for 30 min at room temperature. The typical reaction mixture contained 1.5 fmol of $^{32}P$ DNA, 3 μg of cell extracts, 1 to 3 μg of poly (dI-dC) in 10 mM Tris-Cl (pH 7.9), 1 mM $MgCl_2$, 1 mM DTT, 1 mM ethylenediamine tetra acetic acid (EDTA), and 5 % glycerol. After incubation, reaction mixtures were subjected to electrophoresis in 4% polyacrylamide gels for 90–120 min at 160 V in 0.5× TBE (Sambrook, J., et al., Molecular Cloning: A Laboratory Manual, $2^{nd}$ ed. Cold Spring Harbor Press, NY, 2: 11.23–11.44 (1989)), then dried and autoradiographed. Probes were labeled with [α32P] deoxy CTP by Klenow enzyme (In Vitro labeling kit, Amersham) following the manufacturer's instructions, or by [γ$^{32}$P] ATP using T4 polynucleotide kinase. Labeled probes were then purified either through G-50 columns (5 prime→3 Prime) or on an 8% polyacrylamide gel.

Cell extracts to perform class II gel shift studies were prepared exactly as for class I studies (Dignam et al., ibid, 582–598 (1983); Giuliani C, et al., J. Biol. Chem. 270: 11453–11462 (1995); Saji M, et al., J. Biol. Chem. 272: 20096–20107 (1997); Montani, V., et al., Endocrinology 139: 280–289 (1998a); Montani, V., et al., Endocrinology 139: 290–302 (1998b)), with the exception that the extracts were from γ-interferon treated cells, usually 100 U/ml interferon for 24 to 48 hours. Similarly, electrophoretic mobility shift assays (EMSA) were performed in the same way. Oligonucleotides used for EMSA were synthesized (Operon Technologies, Inc.) or were purified from 2 % agarose gels using either QIAEX (Qiagen, Chatsworth, Calif.) or Jet Sorb (Genomed) following restriction enzyme treatment of chimeric HLA-DRα-CAT constructs (Montani et al., 1998a, b). The oligonucleotides were dephosphorylated with calf intestinal alkaline phosphatase, labeled with [γ-$^{32}$P]dCTP or with [γ-$^{32}$P]ATP using T4 polynucleotide kinase, then purified on an 8% native polyacrylamide gel (Giuliani C, et al., ibid, 11453–11462 (1995); Saji M, et al., ibid, 20096–20107 (1997); Sambrook J, et al., ibid, 2:11.23–11.44 (1989); Montani, V., et al., ibid, 280–289 (1998a), 290–302 (1998b)).

Binding reactions for class II EMSA used similar conditions as well. They were carried out in a volume of 20 μl for 30 min at room temperature. The reaction mixtures contained 1.5 fmol of [$^{32}$P]DNA, 3 μg cell extract and 1.5 to 3 μg poly(di-dC) in 10 mM Tris-Cl at pH 7.9, 1 mM $MgCl_2$, 1 mM DTT, 1 mM EDTA, and 5% glycerol. Where indicated, unlabeled double- or single-stranded oligonucleotides were added to the binding reaction as competitors and incubated with the extract for 20 min at room temperature prior to the addition of labeled DNA. Similarly, in experiments using antiserum, extracts were also incubated in the same buffer containing antiserum or normal rabbit serum for 20 min at room temperature before being processed as above. Following incubations, reaction mixtures were subjected to electrophoresis on 3.5 or 5 % native polyacrylamide gels at 160 V in 0.5xTBE, at room temperature, for 1.5 to 2 h. Gels were dried and autoradiographed at -80° C overnight unless otherwise noted.

Other Methods

Protein concentration was determined by Bradford's method (Bio-Rad); recrystallized bovine serum albumin was the standard. DNA was prepared and purified by CsCl gradient centrifugation (Davis L G, et al., Basic Methods in Molecular Biology, Elsevier, N.Y., pp 93–98 (1986)). The sequences of all constructs were confirmed by a standard method (Sanger F, et al., Proc. Natl. Acad. Sci. USA 74:5463–5467 (1977)). Values are the mean ±SE of these experiments where noted. Significance between experimental values was determined by two-way analysis of variance and are significant if P values were <0.05 when data from all experiments were considered.

MMI-Sensitive Elements in MHC Class I and Class H Genes

MHC Class I

Regulatory elements responsive to MMI have been identified in the promoter of the swine MHC class I gene, PDI. Two regulatory domains have been identified in the 5' flanking region of the PD1 gene. A downstream regulatory domain is between approximately −203 and −1 bp from the transcriptional start site (FIG. 1B). This region contains an interferon response element and a major enhancer (Enhancer A), as well as a site homologous to a cyclic AMP response element (CRE) element. Studies using gel mobility shift assays have demonstrated that MMI-induced or modified proteins interact with this region and can regulate transcription initiation (Saji, et al. ibid., 20096–20107 (1997); Singer et al., U.S. Pat. No. 5,556,754, issued Sep. 17, 1996) particularly Y box proteins. Another complex regulatory region, showing overlapping silencer and enhancer activity, has been mapped between −769 and −673 base pairs upstream of the promoter (Weissman, J. D. and Singer, D. S. Mol. Cell. Biol. 11:4217–4227 (1991)). The enhancer and silencer elements in this upstream regulatory domain are linked to tissue specific expression and tissue specific levels of the Class I gene (Weissman, J. D. and Singer, D. S., ibid, 4217–4227 (1991)) and involve Sox-4 (Singer, D S et al., U.S. Pat. No. 5,556,754 (1996)).

Saji, et al. (J. Clin. Endocrinol. Metab. 75: 871–878 (1992b)) showed reduced expression of MHC Class I gene in rat FRTL-5 cells treated with MMI. This study also showed that the effect of MMI in MHC Class I expression was at the level of transcription. MMI increases the appearance of a normal complex with the downstream regulatory domain and decreases the appearance of the silencer complex of the upstream regulatory domain. These changes result in decreased constitutive control (upstream regulatory domain) and dominant hormonal control (downstream regulatory domain). The MMI action is additive to TSH which acts on the downstream regulatory domain (Saji, et al., ibid, 20096–20107 (1997) and Singer, et al., U.S. Pat. No. 5,556, 754 (1996)).

The FRTL-5 thyroid cell system is therefore a good system to identify the regulatory DNA sequence elements and trans-acting factors involved in the MMI effect. PD1 Gel shift mobility assays were performed using the 5' flanking region of the PD1 gene and cell extracts from FRTL-5 cells treated or not with γ-interferon and treated with MMI and MMI derivatives and tautomeric cyclic thiones (see Table 1).

FIG. 1A shows the silencer and enhancer regions of the 140 region oliogonucleotide used to map the region for the MMI derivative or tautomeric cyclic thione activity of the gel shifts. The silencer and enhancer regions of relevance are noted by the arrows. The 140 fragment is derived from the PD1 promoter of the PD1 Class I MHC gene (Singer, D. S., et al. *Proc. Natl. Acad. Sci. USA*, 79:1403–1407 (1982)).

Figure 2:
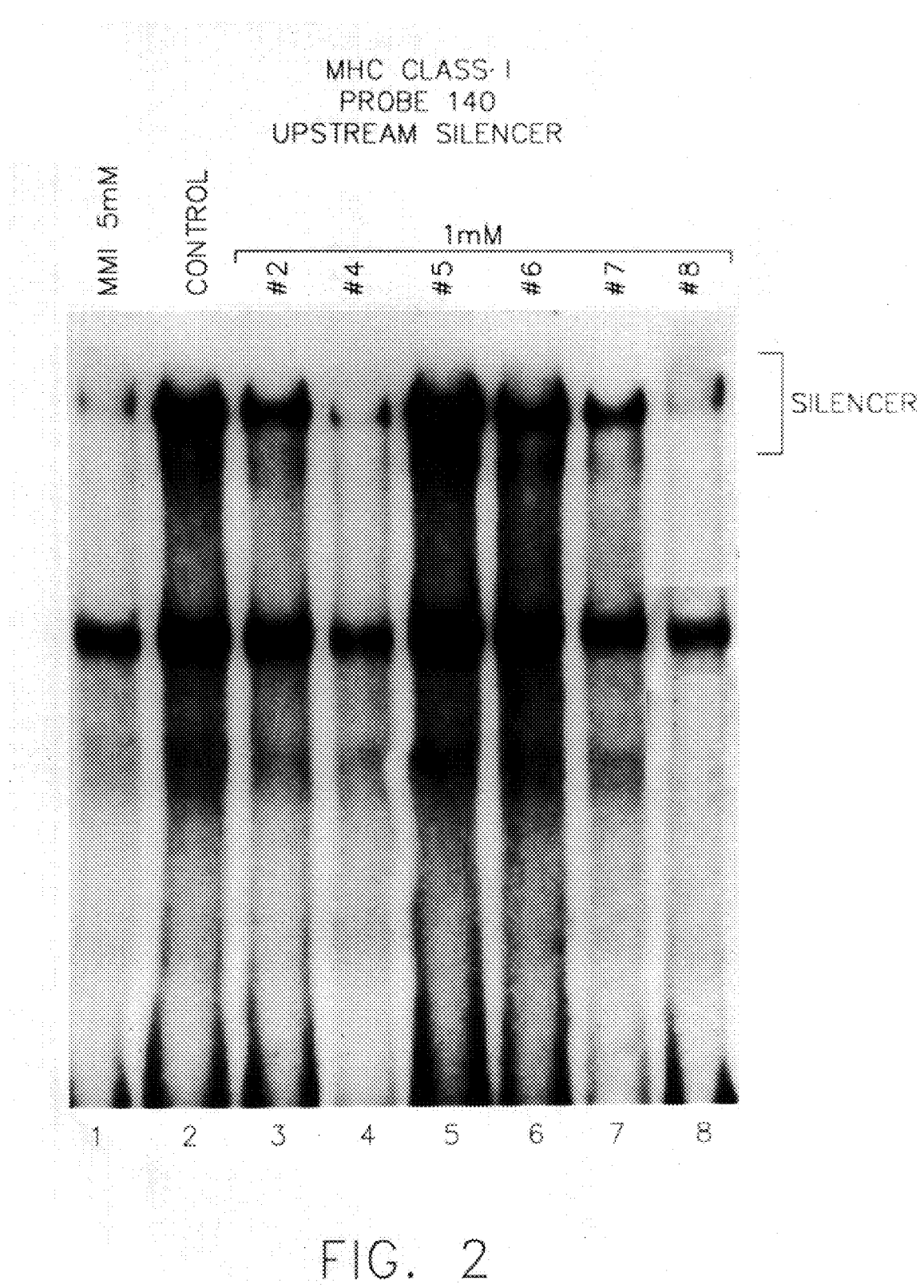

FIG. 2 shows a gel shift using the radio labeled 140 fragment noted in FIG. 1 and shows the silencer complex regulated by MMI.

TABLE 1

| Compounds | Imidazole | 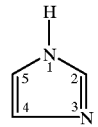 |
|---|---|---|
| #1 | 1-Methylimidazole-2-thiol (Methimzaole) $C_4H_6N_2S$; 1-Methyl-2-mercaptoimidazole (MMI) | 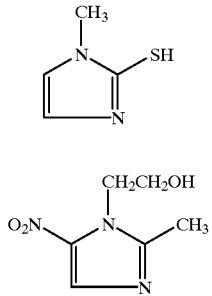 |
| #2 | 2-Methyl-5-nitro-1-imidazole ethanol (Metronidazole) $C_6H_9N_3O_3$;  MW: 171.16 | 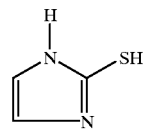 |
| #3 | 2-Mercaptoimidazole MW: 100.14 | 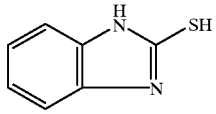 |
| #4 | 2-Mercaptobenzimidazole MW: 150.20 | 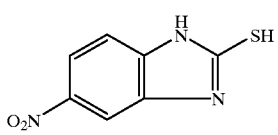 |
| #5 | 2-Mercapto-5-nitrobenzimidazole MW: 195.20 | 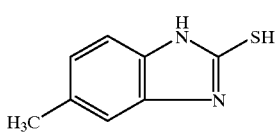 |
| #6 | 2-Mercapto-5-methylbenzimidazole MW: 164.3 | 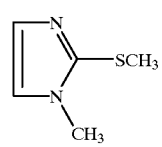 |
| #7 | S-Methylmethimazole $C_5H_8N_2S$; MW: 128.20 B.P. 48° @100 u (liq.) | |
| #8 | N-Methylmethimazole $C_5H_8N_2S$; MW: 128.20 B.P. 188°–194° | 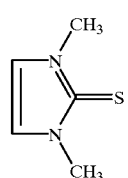 |

TABLE 1-continued

| Compounds | Imidazole | |
|---|---|---|
| #9 | 5-Methylmethimazole<br>$C_5H_8N_2S$;<br>MW: 128.20<br>B.P. 254°–255° | 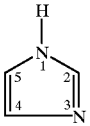 |
| #10 | 5-Phenylmethimazole<br>$C_{10}H_{10}N_2S$;<br>MW: 190.27<br>B.P. 168°–173° | 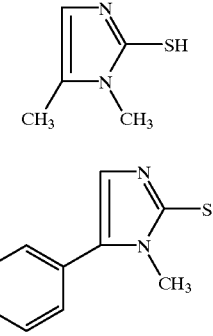 |
| #11 | 1-Methyl-2-Thiomethyl-<br>5(4)nitroimidazole | 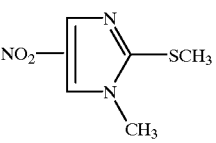 |

Lane 2 shows the complex formed between the silencer region and cell extracts from FRTL-5 rat thyroid cells maintained in the presence of 5H medium (no TSH) plus 5 % serum. The effect of the addition of 5 mM MMI to cells for 48 hours prior to extract preparation from cells maintained in SH medium is shown in lane 1 of FIG. 2. The effect of the addition of 1 mM concentration of representative MMI derivatives to cells maintained in 5H medium for 48 hours prior to extract preparation is shown in lanes 3 to 8 in FIG. 2. The structures and names of the representative numbered compounds are in Table 1. The MMI or its derivatives decrease the silencer complex. The decrease can be quantitated by densitometry of autoradiograms or phosphoimaging on a Bas 1500 imager (for example). Quantitation is based on the decrease relative to the control and normalized by the unchanged faster migrating complexes.

The following (Table 2) summarizes results from experiments with the compounds described in Table 1 but modified to include different concentrations of active compounds in the EMSA. Compound 10 is the most effective.

TABLE 2

EFFECT OF 11 COMPOUNDS ON GEL SHIFTS WITH UP-STREAM 140 CLASS I PROBE USING EXTRACTS FROM 5H CELLS TREATED WITH THE NOTED ACTIVE COMPOUNDS. % INHIBITION OF CONTROL SILENCER COMPLEX FORMATION

| | Compound | 10 µM | 100 µM | 1 mM | 5 mM |
|---|---|---|---|---|---|
| | Control | 0 | 0 | 0 | 0 |
| 1 | Methimazole | 0 | 0 | 20 ± 15 | 75 ± 12 |
| 2 | Metronidazole | 0 | 0 | 45 ± 19 | 86 ± 15 |
| 3 | 2-mercaptoimidazole | 0 | 0 | 0 | 0 |
| 4 | 2-mercaptobenzimidazole | 0 | 5 | 75 ± 10 | Insol |
| 5 | 2-mercapto-5-nitrobenzimidazole | 0 | 0 | 0 | Insol |
| 6 | 2-mercapto-5-methylbenzimidazole | 0 | 0 | 20 ± 18 | Insol |
| 7 | S-methylmethimazole | 0 | 10 ± 13 | 50 ± 9 | ND |
| 8 | N-methylmethimazole | 0 | 18 ± 18 | 70 ± 14 | ND |
| 9 | 5-methylmethimazole | 0 | 0 | 15 ± 15 | 30 ± 20 |
| 10 | 5-Phenylmethimazole | 25 | 60 ± 10 | 85 ± 15 | ND |
| 11 | 1-methyl-2-thiomethyl-5(4)nitroimidazole | 0 | 20 ± 12 | 76 ± 18 | ND |

Values from three separate experiments ± SD.
ND = Not done

Figure 4:
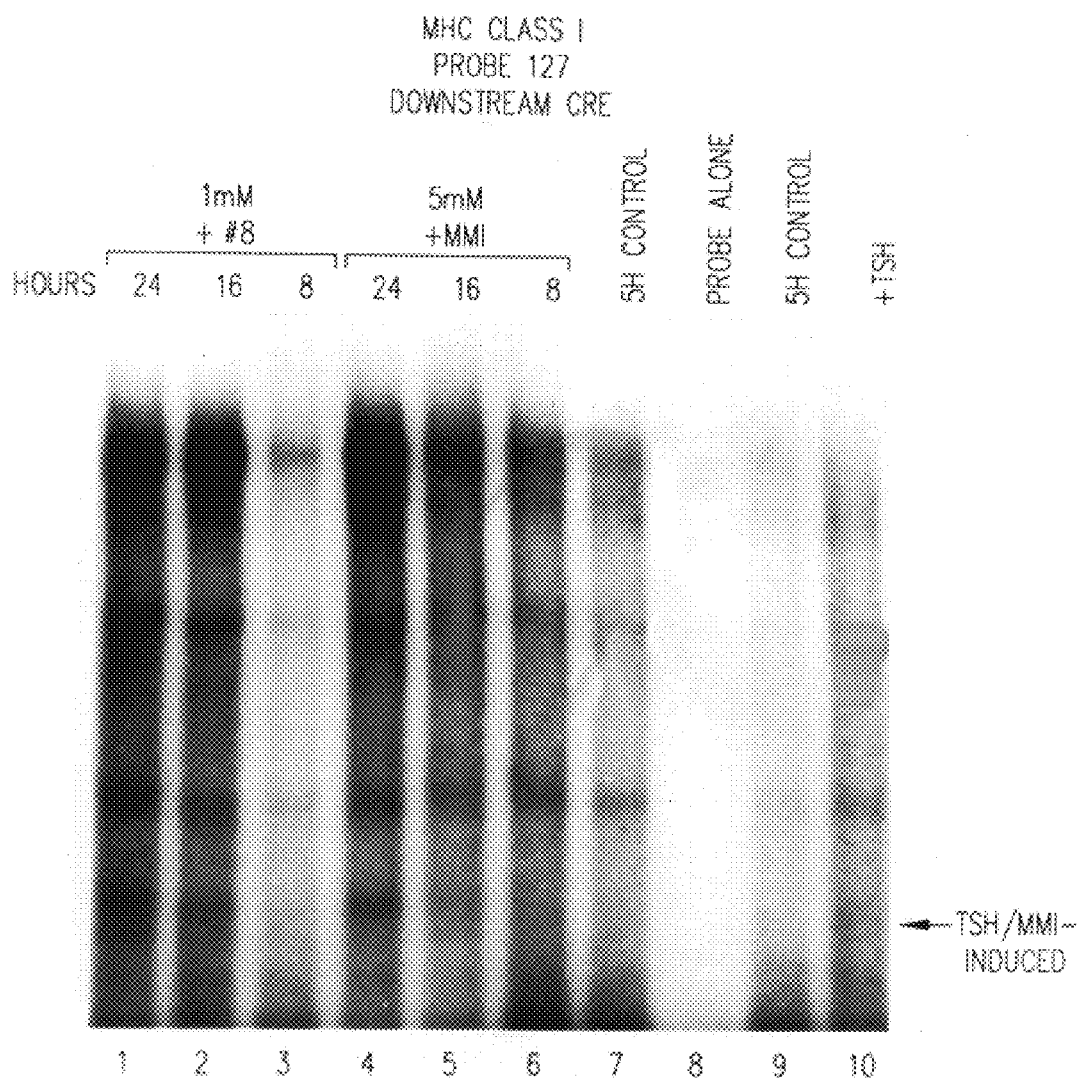

FIG. 3 denotes the sequence of the downstream region of the PD1 promoter. The location of enhancer A (−180 to −170 bp), the interferon response element (IRE; −161 to −150 bp), and the cAMP response element (CRE; −107 to −100 bp) are noted. The downstream silencer is between −127 and −80 bp (Saji, et al., ibid, 20096–20107 (1997)). Using a 127 bp probe, −125 to +1 bp, MMI (lane 4) or TSH (lane 10) induce the formation of a rapidly migrating protein/DNA complex (FIG. 4) which is clearly evident 24 to 48 h after SH cells are treated. MMI derivatives can also increase this complex, as illustrated for compound 8 in FIG. 4 (lanes 1 to 3). The time most suitable for measurement is 24 to 48 h (FIG. 4) the complex can be quantitated by comparison to control (lane 7 or 9) using densitometry or the phosphoimager as noted earlier. In this case, the increase over control (set at 1) is measured in arbitrary units relative to the maximal increase induced by 5 mM MMI which is arbitrarily set at 10. The results using all 11 compounds in Table 1, each added to cells at different concentrations 48 hours before extracts were prepared, are summarized in Table 3. Compound 10 clearly is again most effective when several experimental sets using extracts from different batches of cells were evaluated.

TABLE 3

EFFECT OF 11 COMPOUNDS ON GEL SHIFTS WITH DOWN-STREAM 127 CLASS I PROBE USING EXTRACTS FROM 5H CELLS TREATED WITH THE NOTED ACTIVE COMPOUNDS % INCREASE OVER CONTROL RELATIVE TO THE MAXIMAL (5 mM) MMI-INCREASED SILENCER COMPLEX WHICH IS SET AT 10

|    | Compound                              | 10 μM   | 100 μM  | 1 mM        | 5 mM     |
|----|---------------------------------------|---------|---------|-------------|----------|
|    | Control                               | 0       | 0       | 0           | 0        |
| 1  | Methimazole                           | 0       | 0       | 2 ± 1       | 10       |
| 2  | Metronidazole                         | 0       | 0       | 5 ± 1       | 10 ± 2   |
| 3  | 2-mercaptoimidazole                   | 0       | 0       | 0           | 0        |
| 4  | 2-mercaptobenz-imidazole              | 0       | 3 ± 0.5 | 9 ± 1.5     | Insol    |
| 5  | 2-mercapto-5-nitrobenzimidazole       | 0       | 0       | 0           | Insol    |
| 6  | 2-mercapto-5-methylbenzimidazole      | 0       | 0       | 3 ± 2       | Insol    |
| 7  | S-methylmethimazole                   | 0       | 2 ± 1   | 6 ± 0.5     | ND       |
| 8  | N-methylmethimazole                   | 0       | 3 ± 2   | 9 ± 1       | ND       |
| 9  | 5-methylmethimazole                   | 0       | 0       | 1.5 ± 1.5   | 2.5 ± 1  |
| 10 | 5-Phenylmethimazole                   | 3 ± 1.5 | 7 ± 1   | 10 ± 1      | ND       |
| 11 | 1-methyl-2-thio-methyl-5(4)nitroimidazole | 0   | 2 ± 1   | 10 ± 1      | ND       |

Values from three separate experiments ± SD.
ND = Not done

MHC Class II

Major histocompatibility complex (MHC) class II molecules are heterodimeric transmembrane glycoproteins which are encoded by the HLA-D region on chromosome 6 and play a central role in immune function (German RM, et al., Ann. Rev. Immunol. 4:281–315 (1986); Schwartz R S, and Datta S K, Autoimmunity and Autoimmune Diseases, in Paul, W. E. (ed), *Fundamental Immunology*, Raven Press, NY, pp 819–866 (1989); Benoist C, et al., Ann. Rev. Immunol. 8:681–715 (1990); Glimcher L H, et al., Ann. Rev. Immunol. 10:13–49 (1992); Ting J P-Y, et al., Curr. Opin. Immunol. 5:8–16 (1993)). Class II antigens are usually expressed on antigen presenting cells such as B cells, macrophages or dendritic cells; the class II molecules present antigenic peptides to CD4 positive T lymphocytes, causing T cell activation (German RM, et al., ibid, (1986); Schwartz R S, et al., ibid, (1989); Benoist C, et al., ibid, (1990); Glimcher L H, et al., ibid, (1992); Ting J P-Y, et al., ibid, (1993)). Class II expression is normally not evident on epithelial cells, such as thyrocytes, synovial cells, or islet cells; abnormal or aberrant expression of class II molecules on thyrocytes, synovial cells, or islet cells is associated with autoimmune thyroid diseases, rheumatoid arthritis, and diabetes, respectively (Bottazzo G F, et al., Lancet 2:1115–1119 (1983); Bottazzo G F, et al., N. Engl. J. Med. 313:353–360 (1985); Todd I, et al., Ann. NY Acad. Sci. 475:241–249 (1986); German R M, et al., ibid (1986); Burmester G R, et al., J. Clin. Invest. 80:594–605 (1987); Piccinini L A, et al., Clin. Endocrinol. (Oxf) 26:253–272 (1987); Schwartz R S, et al., ibid (1989); Benoist C, et al., ibid (1990); Glimcher L H, et al., ibid (1992); Ting J P-Y, et al., ibid (1993)). The assumption emerged that aberrant class II expression allowed cells to become antigen presenting cells, interact with T-cells, and initiate an immune response (Schwartz R S, et al., ibid (1989); Weetman A P, et al., Endocr. Rev. 15:788–830 (1994)). It was, nevertheless, not clear whether this was a secondary response to cytokines, such as γ-IFN produced by lymphocytes infiltrating the tissue, or was the result of a more primary insult on the tissue itself. More importantly, there was little direct evidence that class II was critical in the initiation of autoimmune thyroid disease (Weetman A P, et al., ibid (1994)). However, a recent study makes this hypothesis more attractive (Shimojo N, et al., Proc. Natl. Acad. Sci. USA 93:11074–11079 (1996)).

One form of autoimmune thyroid disease (ATD) is Graves' disease, wherein autoantibodies develop to the TSHR and induce hyperthyroidism by mimicking the action of TSH. Whereas numerous attempts to develop a Graves' disease model by immunizing animals with the extracellular domain of the TSHR have largely failed (see, for example, Seetharamaiah, G. S. et al., Autoimmunity 14: 315–320 (1993); Costagliola et al., J. Mol. Endocrinol. 13: 11–21 (1994); Costagliola et al., Biochem. Biophys. Res. Commun. 199: 1027–1034 (1994); Costagliola et al., Endocrinology 135: 2150–2159 (1994); Marion, A., et al., Cell. Immunol. 158: 329–341 (1994); Wagle, N M, et al., Autoimmunity 18: 103–108 (1994)), immunizing mice with fibroblasts transfected with the human TSHR and a MHC class II molecule, but not either alone, has induced ATD with the major humoral and histological features of Graves' (Shimojo N, et al., ibid, 11074–11079 (1996)): stimulating TSHR antibodies (TSHRAbs), thyrotropin binding inhibiting immunoglobulins (TBII) which are different from stimulating TSHRAbs, increased thyroid hormone levels, thyroid enlargement, and thyrocyte hypercellularity. These results suggest that aberrant expression of MHC class II molecules on thyrocytes can result in the induction of functional TSHRAbs which stimulate the thyroid. They suggest that acquisition of antigen-presenting ability on a thyroid cell, as a result of aberrant class II expression, can activate T and B cells normally present in an animal, thereby allowing normal immune tolerance to be broken. By analogy, this is relevant to the development of rheumatoid disease, diabetes, and numerous other autoimmune diseases associated with autoimmunity and aberrant MHC class II expression. Understanding the basis for aberrant class II expression in thyrocytes is, therefore, a potentially important aspect of understanding the pathogenesis not only of autoimmune thyroid disease but many other autoimmune diseases. Developing agents which suppress MHC class II aberrant expression is important, therefore, in suppressing the autoimmune state. These agents may additionally suppress MHC class I.

The ability of γ-interferon (γ-IFN) to induce class II antigen expression in FRTL-5 thyroid cells and mimic changes in human thyrocytes seen in ATD is well described (Todd I, et al., ibid (1985); Platzer M, et al., Endocrinology 121:2087–2092 (1987); Misaki T, et al., Endocrinology 123:2849–2855 (1988); Zakarija M, et al., Mol. Cell. Endocrinol. 58:329–336 (1988)). HLA-DR gene expression in rat FRTL-5 thyroid cells has been studied in the FRTL-5 thyroid cell model in order to define elements and factors important for γ-IFN-induced aberrant expression (Montani V., et al., ibid (1998a, b)) and is, therefore, a reasonable model to define elements and factors that might be important in ATD and other immune diseases. Using an HLA-DR 5'-flanking region construct from −176 to +45 bp coupled to the chloramphenicol acetyl transferase (CAT) reporter gene, it was shown that, unlike lymphocytes, there is no basal class II gene expression in thyrocytes, but, like some immune cells, γ-IFN can induce expression (Montani V., et al, ibid, (1998a, b)). The ability of γ-IFN to induce aberrant HLA-DR gene expression in FRTL-5 thyroid cells requires, like antigen presenting cells of the immune system which normally express MHC class II, the highly conserved S, $X_1$, $X_2$, and Y boxes on its 5'-flanking region, −137 to −65 bp (Benoist C, et al., ibid (1990); Glimcher L H, et al., ibid (1992); Ting J P-Y, et al., ibid (1993); Reith W, et al., Immunobiology 193:248–253 (1995); Montani V., et al, ibid (1998a, b)). Using gel shift assays and the HLA-DR 5'-flanking region from −176 or −137 to +45 bp as radiolabeled probes, the formation of a major protein/DNA complex and a minor, faster migrating complex with extracts from FRTL-5 cells untreated with γ-IFN was observed (Montani V., et al, ibid (1998a, b)). γ-IFN-induced aberrant expression is associated with increased formation of a specific and novel protein/DNA complex containing CBP, a coactivator of cAMP response element binding proteins (Montani V., et al., ibid (1998a, b)).

Two factors known to regulate class II gene expression in immune cells are the class II transactivator (CIITA) and a Y box binding protein (Ting J P-Y, et al., ibid (1993); Reith W, et al., ibid (1995)). CIITA is a non DNA-binding protein transactivator that functions as a molecular switch to control constitutive and inducible MHC class II gene expression in immune cells; CIITA expression is induced by γ-IFN and is believed to be involved in its activity (Steimle V, et al., Science 265:106–109 (1994); Reith W, et al., ibid (1995); Chang CH, et al., J. Exp. Med. 180:1367–1374 (1996); Mach B, et al., Ann. Rev. Immunol. 14:301–331 (1996)). The human Y box protein, YB-1, was cloned based on its ability to bind to the Y box, an inverted CCAAT box, of the MHC class II gene (Didier D K, et al., Proc. Natl. Acad. Sci. USA 85:7322–7326 (1988)) and has been shown to suppress HLA-DR gene expression in human glioblastoma cells (Ting J P-Y, et al., J. Exp. Med. 179:1605–1611 (1994); MacDonald G H, et al., J. Biol.Chem. 270:3527–3533 (1995)). CIITA can induce the formation of the complex induced by γ-IFN and associated with aberrant class II gene expression in FRTL-5 cells (Montani V., et al., ibid (1998b)); overexpression of the Y box protein in FRTL-5 cells suppresses the formation of this complex (Montani V., et al., ibid (1978b)). It is reasonable to presume, therefore, that this complex is involved in aberrant class II expression associated with ATD and is related to aberrant class II expression in other autoimmune diseases. Moreover, the data support the conclusion that the negative regulation of class II, as well as the class I genes, involves common transcription factors, the Y box protein, consistent with the hypothesis (Kohn L D, et al., ibid (1997); Saji M., et al., ibid (1998)) that coordinate negative control of class II, as well as class I genes, by common transcription factors maintains self tolerance during hormone-induced increases in thyroid cell growth and function.

Methimazole (MMI) is an agent effective in treating Graves' disease and preventing experimental thyroiditis in rats or mice (Cooper D S, N. Engl. J. Med. 311:1353–1362 (1984); Davies T F, et al., J. Clin. Invest. 73:397–404 (1984); Reinhardt W, et al., Endocrinol. Invest. 12:559–563 (1989)). The action of methimazole on MHC class II gene expression in thyrocytes has, however, been controversial. Thus, there have been differing reports on the ability of antithyroid drugs to suppress MHC class II antigen expression in patients with Graves' disease (Carel J C, et al., in The Thyroid and Autoimmunity, Drexhage and Weirsinga (eds), Excerpta Medica, Amsterdam, pp. 145–147 (1986); Aguayo J, et al., J. Clin Endocrinol. Metab. 66: 903–908 (1988); Davies T F, et al., Clin. Endocrinol. (Oxf) 31:125–135 (1989)) and concerns were expressed that there was an absence of dose dependencies on immunologic parameters in refractory Graves' patients treated with MMI before surgery (Paschke R, et al., J. Clin. Endocrinol. Metab. 80:2470–2474 (1995)). Nevertheless, formation of γ-IFN or CITA-induced complex, as well as increased HLA-DR gene expression, was suppressed by methimazole in FRTL-5 thyroid cells (Montani V., et al., ibid (1998a)) as a function of time and concentration. Thus, MMI suppression of this complex in FRTL-5 cells can be considered a marker of its ability to suppress aberrant MHC class II expression and autoimmune disease. The clinical relevance of aberrant class II and abnormal class I expression in autoimmune disease has recently been demonstrated by the observation that iodide suppresses both class II and class I expression, which are elevated in Graves' thyroids (Schuppert F, et al., J. Clin. Endocrinol. Metab. 81:3622–3628 (1996)); iodide is an agent which like MMI can be used to treat Graves' patients and has been used extensively to prepare Graves' patients for thyroidectomies (Nagataki S, et al., Autoregulation: effects of iodide. In: Braverman LE, Utiger R D (Eds) Werner and Ingbar's The Thyroid: a fundamental and clinical text. Lippencott-Raven, Philadelphia, 241–247 (1996)).

Figure 5:
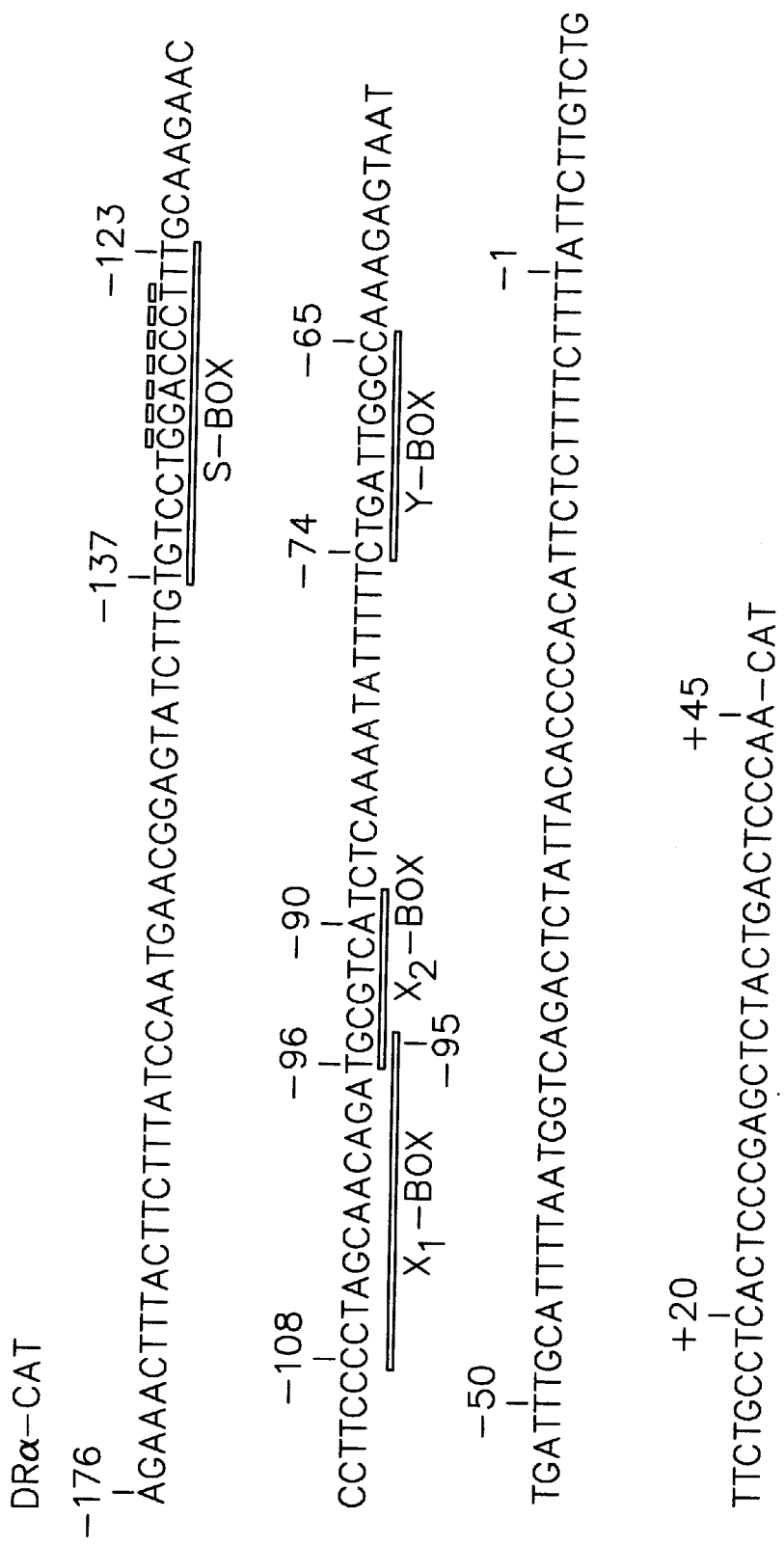

FIG. 5 depicts the nucleotide sequence of the 5'-flanking region of the HLA-DR gene from −176 bp. The S, $X_1$, $X_2$, and Y boxes or elements, which are conserved in all class II MHC promoters characterized to date, HLA-DR, -DQ, and -DP, are underlined (bold) and their 5' and 3' termini in DR numbered. The more restricted S box site noted in some reports (Ting, J P-Y, et al., ibid (1993); Benoist C, et al., ibid (1990)) is noted by a dashed line over the more extensive S box used herein or in other reports (Reimold A M, et al., J. Immunol. 151:4173–4182 (1993)).

Figure 6:
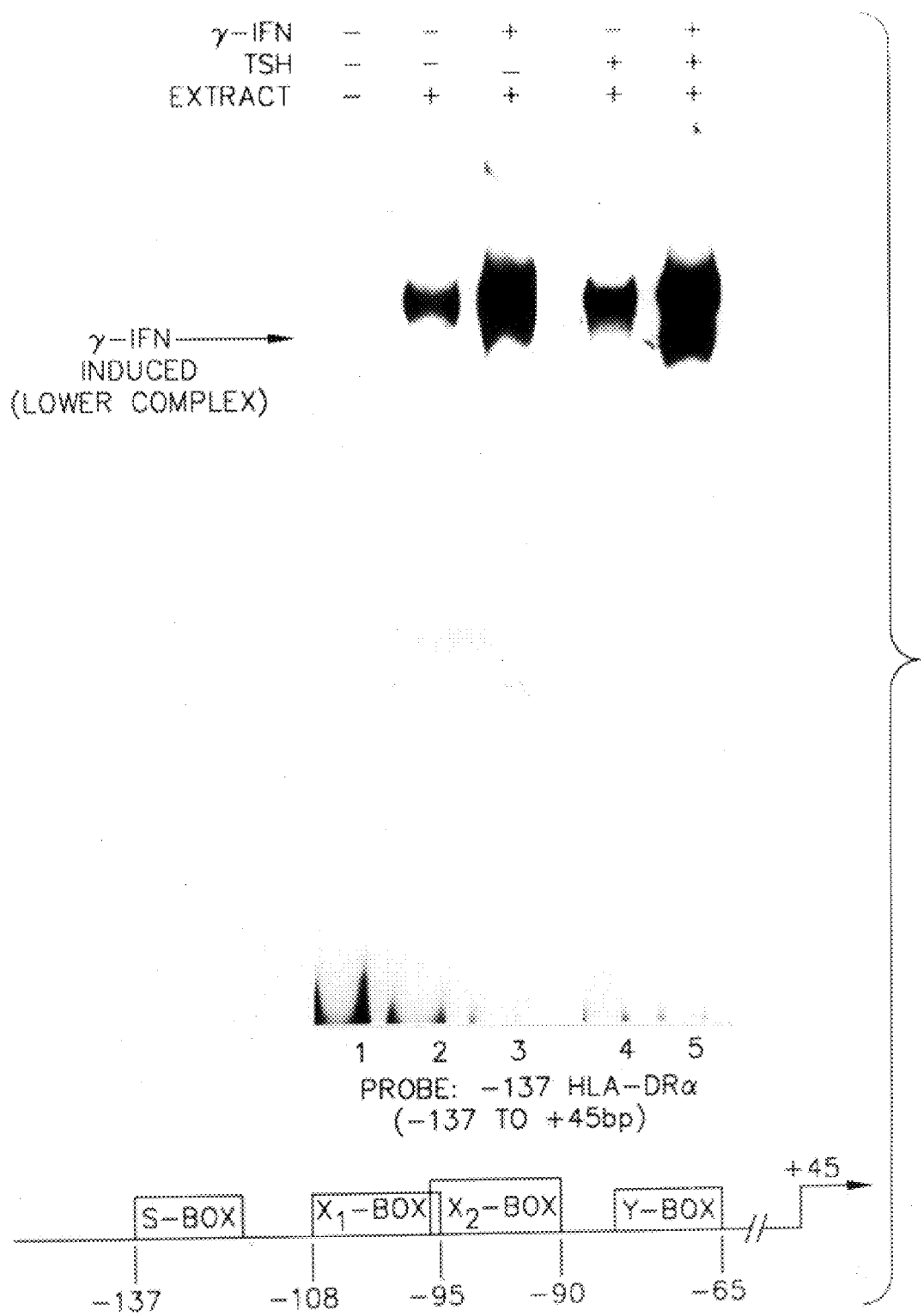

FIG. 6 depicts the electrophoretic mobility shift analysis of the ability of a $^{32}$P-radiolabeled DR α-5'-flanking region probe to form protein/DNA complexes with extracts from FRTL-5 cells maintained with and without TSH and treated or not with γ-IFN. The probe was excised by restriction enzyme treatment of a −137 to +45 bp DR -CAT chimera (Reimold AM, et al., ibid (1993); Montani V., et al., ibid (1998a, b)) and is diagrammatically represented at the bottom of the Figure. Extracts were from FRTL-5 rat thyroid cells grown to near confluency in TSH or maintained 6 days in 5H medium; duplicate cultures of each were treated with 100 U/ml γ-IFN for the last 48 h before the experiment was terminated. Cell extracts made from each set of cells were incubated with the $^{32}$P-radiolabeled probe containing −137 bp of the DR α5'-flanking region and EMSA performed as described above. In this experiment, the autoradiogram was exposed overnight at −70° C.

Figure 7:
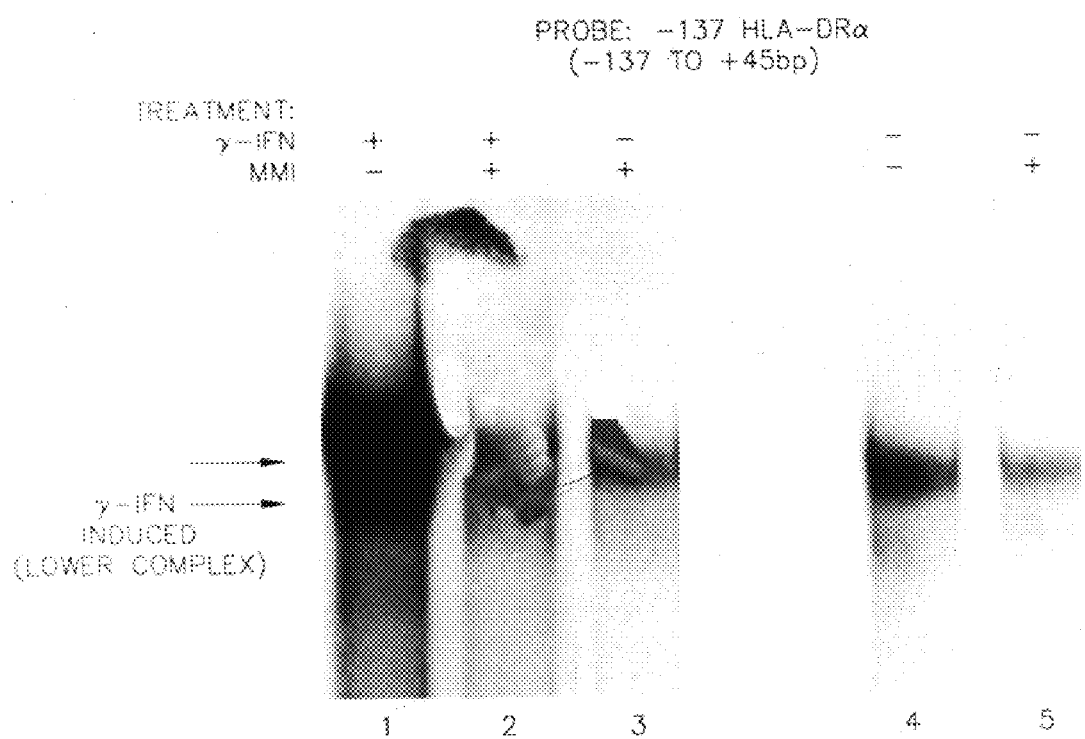

FIG. 7 depicts the effect of MMI on the ability of γ-IFN to increase the formation of protein/DNA complexes with the $^3$P-radiolabeled DR α5'-flanking region probe. The radiolabeled probe is the same as that used and diagrammatically presented in FIG. 6; it contains −137 bp to +45 bp of the 5'-flanking region of DRα-CAT chimera. Extracts were from FRTL-5 rat thyroid cells grown to near confluency in TSH, maintained 6 days in SH medium, then treated with 100 U/ml γ-IFN, 5 mM MMI, or both for the last 48 h before the experiment was terminated. Cell extracts were incubated and EMSA performed as in FIG. 6 and as described above. The arrows denote the upper and lower complexes seen in FIG. 6. In this experiment, the autoradiograms were exposed 72 h at −70° C. Lane 5 contains extract from control cells; extracts from cells treated with IFN or MMI are noted at the top of the panels. The same results were obtained if cell extracts were from FRTL-5 rat thyroid cells grown to near confluency in TSH and treated with 100 U/ml γ-IFN for the last 48 h before the experiment was terminated.

Figure 8:
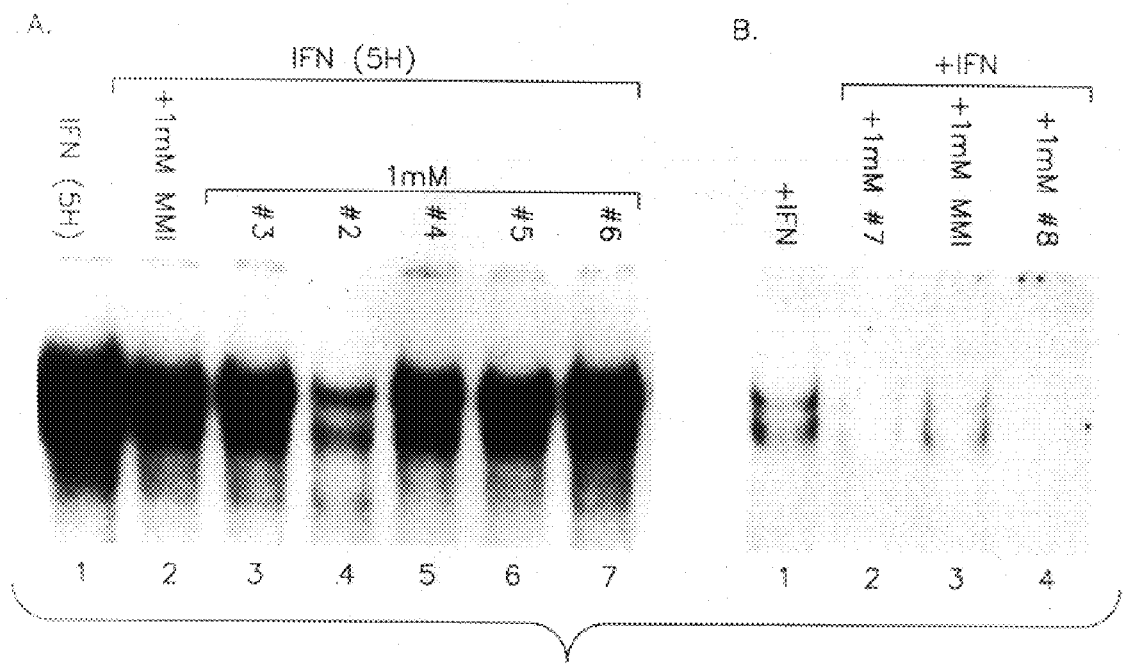

Using the same protocol as for MMI (FIG. 7), but different exposure times of autoradiograms, various active compounds (MMI derivatives or tautomeric cyclic thiones) were shown to decrease class II complexes linked to interferon-induced (aberrant) or constitutive expression of class II on the cell as exemplified in FIG. 8. Compounds 2, 7, 8 are significantly more effective suppressors than MMI (lanes 4 in FIG. 8A and 2 and 4 in FIG. 8B vs. lanes 2 in FIG. 8A and 3 in FIG. 8B, respectively). Quantitation of the mean decrease in the IFN-induced complex for each of the compounds is evident in Table 4.

In sum, the effect of different derivatives on aberrant class II expression, measured by the decrease in S-IFN increased complex formation differs from compound to compound and can be quantitated. Compound 10 is most effective as is the case for Class I shifts described above.

TABLE 4

EFFECT OF 11 COMPOUNDS ON GEL SHIFTS WITH 137 CLASS II PROBE USING EXTRACTS FROM γ-IFN-TREATED 5H CELLS WHICH ARE ALSO TREATED WITH THE NOTED ACTIVE COMPOUNDS.
% INHIBITION OF IFN-INCREASED COMPLEX FORMATION

| | Compound | 10 µM | 100 µM | 1 mM | 5 mM |
|---|---|---|---|---|---|
| | Control | 0 | 0 | 0 | 0 |
| 1 | Methimazole | 0 | 0 | 10 ± 5 | 85 ± 12 |
| 2 | Metronidazole | 0 | 0 | 55 ± 14 | 95 ± 10 |
| 3 | 2-mercaptoimidazole | 0 | 0 | 0 | 0 |
| 4 | 2-mercaptobenzimidazole | 0 | 5 | 65 ± 15 | Insol |
| 5 | 2-mercapto-5-nitrobenzimidazole | 0 | 0 | 45 ± 21 | Insol |
| 6 | 2-mercapto-5-methylbenzimidazole | 0 | 0 | 35 ± 18 | Insol |
| 7 | S-methylmethimazole | 0 | 16 ± 11 | 74 ± 13 | ND |
| 8 | N-methylmethimazole | 0 | 21 ± 18 | 86 ± 14 | ND |
| 9 | 5-methylmethimazole | 0 | 0 | 25 ± 15 | 40 ± 20 |
| 10 | 5-Phenylmethimazole | 35 ± 15 | 78 ± 10 | 95 ± 16 | ND |
| 11 | 1-methyl-2-thiomethyl-5(4)nitroimidazole | 0 | 45 ± 9 | 86 ± 19 | ND |

Values from three separate experiments ± SD.
ND = Not done

EXAMPLE 3

Assessment of the effect of MMI derivatives or tautomeric cyclic thiones on the Promoter activity of MHC Class I and Class II using transient transfection analysis and CAT assays Plasmid Construction The full length PD1 promoter, PD1 CAT construct pH (−38), inserted into the multicloning site of pSV3CAT, has been previously described (Erhlich, R. et al. *Immunogenetics* 30:18–26 (1989)). Sequential deletion mutants of the full-length PD1 promoter, inserted into the multicloning site of pSV3CAT, have also been previously described (Singer D S, et al., ibid (1991); Saji, et al., Proc. Natl. Acad. Sci. USA 89:1944–1948 (1992a); Saji, et al., J. Clin. Endocrinol. Metab. 75:871–878 (1992b)). Briefly, a nested series of 5' deletions of the upstream regulator region of the PD1 gene were generated by Bal3 digestion; the series 5' termini ranged from −1012 base pairs to −68 base pairs, but all had a common 3' boundary at +15 base pairs. The deletion series was also cloned into the pSV3CAT reporter construct to assess promoter activities (Weisman J D, et al. ibid (1991); Maguire, J. et al., *Mol. Cell. Biol.*, 12:3078–3086 (1992)). For screening the action of MMI, MMI derivatives or tautomeric cyclic thiones on Class I promoter activity, three clones are commonly used: p(−1100) CAT, p(−203) CAT, and p(−127) CAT, preferably p(−203) CAT. The number denotes the most 5'-residue in the 5'-flanking region of the PD1 promoter.

Construction of the HLA-DR promoter constructs has also been described as have been their characteristics (Reimold A M, et al., ibid (1993)). Additional CAT constructs were constructed by PCR, using the HLA-DRα-CAT chimera containing −176 to +45 of 5'-flanking region as template and various primers (Montani V. et al., ibid (1998a, b)). For example, a plasmid containing −38 to +45 bp of the 5'-flanking region of HLA-DRα was constructed with the following primers: a 5' primer with a 5' Sph I restriction site, 5'-ACATGCATGCGGTCAGACTCTATTACACCCCAC-3' and a 3' primer, 5'-CTAGTCTAGTTTGGGAGTCAGTAGAGCTCG-3', with an Xba I restriction site (Montani V., et al., ibid (1998a,b)). The PCR products were purified by phenol-chloroform extraction, digested with Xba I and Sph I, purified from a 2% agarose gel with Jet Sorb (Genomed, Frederick, Md.), dephosphorylated with calf intestinal alkaline phosphatase (New England Biolabs, Beverly, Mass.), and religated (DNA ligation kit, Takara Biochemical, Inc., Berkeley, Calif.) into the pCAT-Basic Vector (Promega, Madison, Wis.) at the Sph I and Xba I sites as described (Reimold AM, et al., ibid (1993); Montani V., et al., ibid (1998a,b)).

The thyroglobulin (TG)-CAT construct, pTG-688-CAT, was derived by substituting the TG promoter insert from a previously described pTG-CAT chimera (Shiinura H, et al., Mol. Endocrinol. 8:1049–1069 (1994)) into the HLA-DRα-CAT chimera from which the class II promoter insert was excised. The vector containing the CAT reporter gene but no insert was the control.

Cell Culture

FRTL-5 rat thyroid cells (Interthyr Research Foundation, Baltimore, Md.; ATCC CRL8305) were the same subclone (F1) used in the gel shift experiments described earlier. They were grown in the following medium: Coon's modified F-12 medium containing 5% heat-treated, mycoplasma-free calf serum, 1 mM nonessential amino acids, and a mixture of six hormones (6H) containing bovine TSH ($1 \times 10^{-10}$M), insulin (10 µg/ml), cortisol (0.4 ng/ml), transferrin (5 µg/ml), glycyl-L-histidyl-L-lysine acetate (10 ng/ml), and somatostatin (10 ng/ml). Cells were diploid and between their $5^{th}$ and $25^{th}$ passage. Fresh medium was added every 2 or 3 days and cells were passaged every 7–10 days. In some experiments, cells were grown to near confluency in 6H medium then maintained for 5–8 days, before experiments were initiated, in 5H medium with no TSH.

TRANSFECTION AND CAT ASSAYS

To measure the promoter activity of MHC class I promoter constructs, as reported by CAT activity, two procedures were used. In one, rat FRTL-5 thyroid cells were transfected by the electroporation method described previously (Saji, M., et al., ibid (1992b); Giuliani, C., et al., ibid (1995); Saji, M., et al., ibid (1997)). In brief, FRTL-5 cells were grown to 80% confluence, put in fresh 6H medium containing 5% calf serum for 12 hours, harvested, washed and suspended at $1.5 \times 10^7$ cells/mil in 0.8 ml electroporation buffer (272 mM sucrose, 7 mM sodium phosphate at pH 7.4, and 1 mM $MgCl_2$). Twenty µg of the full-length CAT construct were added with 5 µg pSVGH. Cells were then pulsed (330 volts, capacitance 25 µfarad), plated (approximately $6 \times 10^6$ cell/dish), and cultured for 12 hours in 6H medium containing 5% calf serum. At that time, cells were placed in 5H medium plus 5% calf serum (control), 5H medium plus 5% calf serum plus 5 mM MMI or different concentrations of active compound (MMI derivative or tautomeric cyclic thione), 6H medium plus 5% calf serum, or 6H medium plus 5% calf serum plus 5 mM MMI or active compound at different concentrations. After 48 hours they were harvested. Cell viability was approximately 80%. Medium was taken for hGH radioimmunoassay to monitor transfection efficiency (Nichols Institute, San Juan Capistrano, Calif.) and cells were harvested for CAT assays which used 20–50 µg cell lysate in a final volume of 130 µl. Incubation was at 37° C. for 2 or 4 hours; acetylated chloramphenicol was separated by thin layer chromatograpy (TLC) and positive spots on TLC plates were cut out and quantitated in a scintillation spectrometer. CAT activity was normalized to GH activity and/or cell protein before data were compared.

Alternatively transient transfections used the same class I-CAT chimeras and a DEAE-dextran procedure (Lopata M A, et al., Nucleic Acids Res. 12:5707–5717 (1984); Giuliani C, et al., ibid (1995)). Cells were grown to near (80%) confluency in 6H medium, shifted to 5H medium for 1 day, washed twice with Dulbecco's modified phosphate buffered saline (DPBS), pH 7.4, and incubated 1 hour with 5 ml serum-free 5H medium containing the plasmid DNA plus 250 µg DEAE-dextran (5 Prime-3 Prime, Inc.). Cells were then exposed to 10% dimethylsulfoxide in DPBS for 3 min., washed twice in DPBS, cultured in 5H medium for 24 hours, then maintained therein another 48 hours with or without MMI, MMI derivatives or tautomeric cyclic thiones, as noted. Efficiency of transfection was determined by cotransfection as above or with 5 µg pRSVLuc (De Wet J R, et al., Mol. Cell. Biol. 7:725–737 (1987)).

To measure the promoter activity of MHC class II promoter constructs, transient transfections in FRTL-5 cells were performed, using one of the following procedures (Montani V., et al., ibid (1998a, b)). In one, FRTL-5 cells were cultivated in 6H medium to approximately 80% confluency, harvested, washed, and resuspended ($1.5 \times 10^7$ cells/ml) in 0.85 ml electroporation buffer (272 mM sucrose, 7 mM sodium phosphate buffer pH 7.4, and 1 mM $MgCl_2$). Plasmid DNA was added, 20 µg of the CAT chimera together with 2 µg pRSV-luciferase which is used to measure the efficiency of transfection. Cells were pulsed (330 V; capacitance 25 µfarad), plated ($6 \times 10^6$ cells/10 cm dish), and cultured in 6H medium plus 5% calf serum supplemented or not with γ-IFN. At the times noted, cells were harvested for CAT and luciferase assays. The second procedure differed as follows. FRTL-5 cells were grown to 80% confluency in 6H medium, then maintained 6 days in 5H medium plus 5% calf serum. Cells were returned to 6H medium for 12 hours, transfected as described above, and maintained in 6H medium plus 5% calf serum for twelve hours. The medium was then changed to fresh 5H medium with 5% calf serum supplemented or not with γ-IFN. Cell viability was approximately 80% in all experiments. CAT activity was measured as described above and values were normalized to luciferase activity measured using the Promega (Madison, Wis.) assay system.

To test the effect of MMI, MMI derivatives or tautomeric cyclic thiones on γ-IFN-increased class II expression in FRTL-5 thyroid cells, the following procedure was used. Transient transfections with the −137 bp or −176 bp DRα-CAT chimeras were performed as described and treated with 100 U/ml γ-IFN for the noted times starting 12 hours after transfection. In duplicate sets of cells, 5 mM MMI or the noted concentrations of MMI derivatives or tautomeric cyclic thiones were added simultaneously with the γ-IFN and CAT activity was measured 48 hours later. Cell viability was approximately 85±5% in all samples. Results were expressed relative to the vector control in the absence of γ-IFN or MMI, after CAT activities were corrected both for luciferase activity and cell protein. These corrections in all cases resulted in less than 5% changes in activity. The same results were obtained using the alternative transfection protocol involving cells maintained in medium with no TSH.

Figure 9:
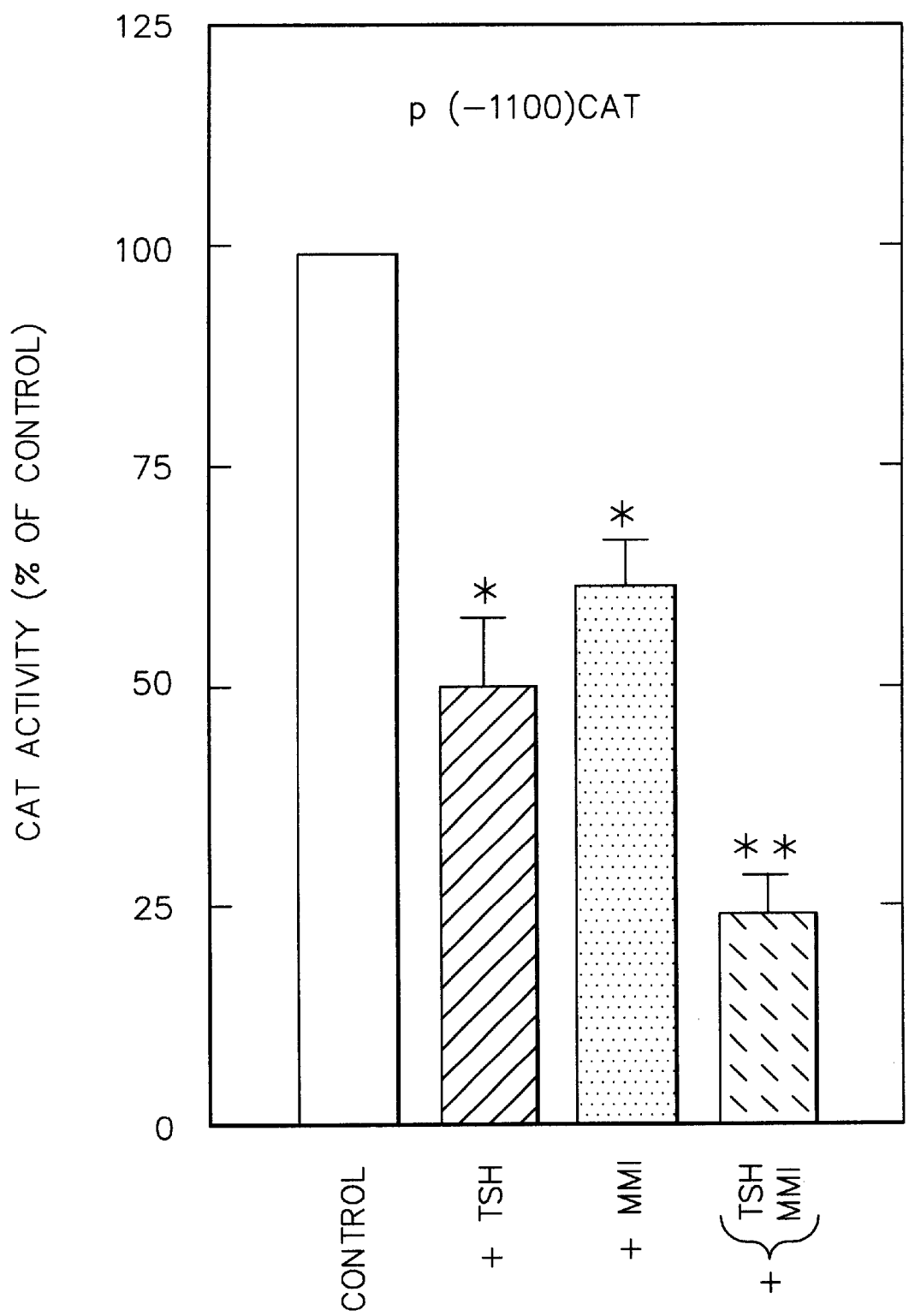

Representative examples of the effect of MMI on basal class I promoter activity and its additive action with TSH are presented below. In FIG. 9, FRTL-5 cells maintained in 5H medium plus 5% calf serum were transfected with a CAT chimera containing 1100 bp of 5'-flanking region of the swine class I promoter by electroporation as described. After 12 h the medium was changed to fresh 5H medium in the presence or absence of $1 \times 10^{-10}$M TSH, 5 mM MMI, or both. Cells were assayed 36 hours later. The value from the transfectant with no TSH or MMI in the medium was the control and was set at 100%. Values are the mean of 3 experiments; significant increases or decreases at P<0.05 (*) or P<0.01 (**) are noted. It is evident that MMI, can decrease class I basal promoter activity and that its action is measurable in cells with or without TSH.

Figure 10:
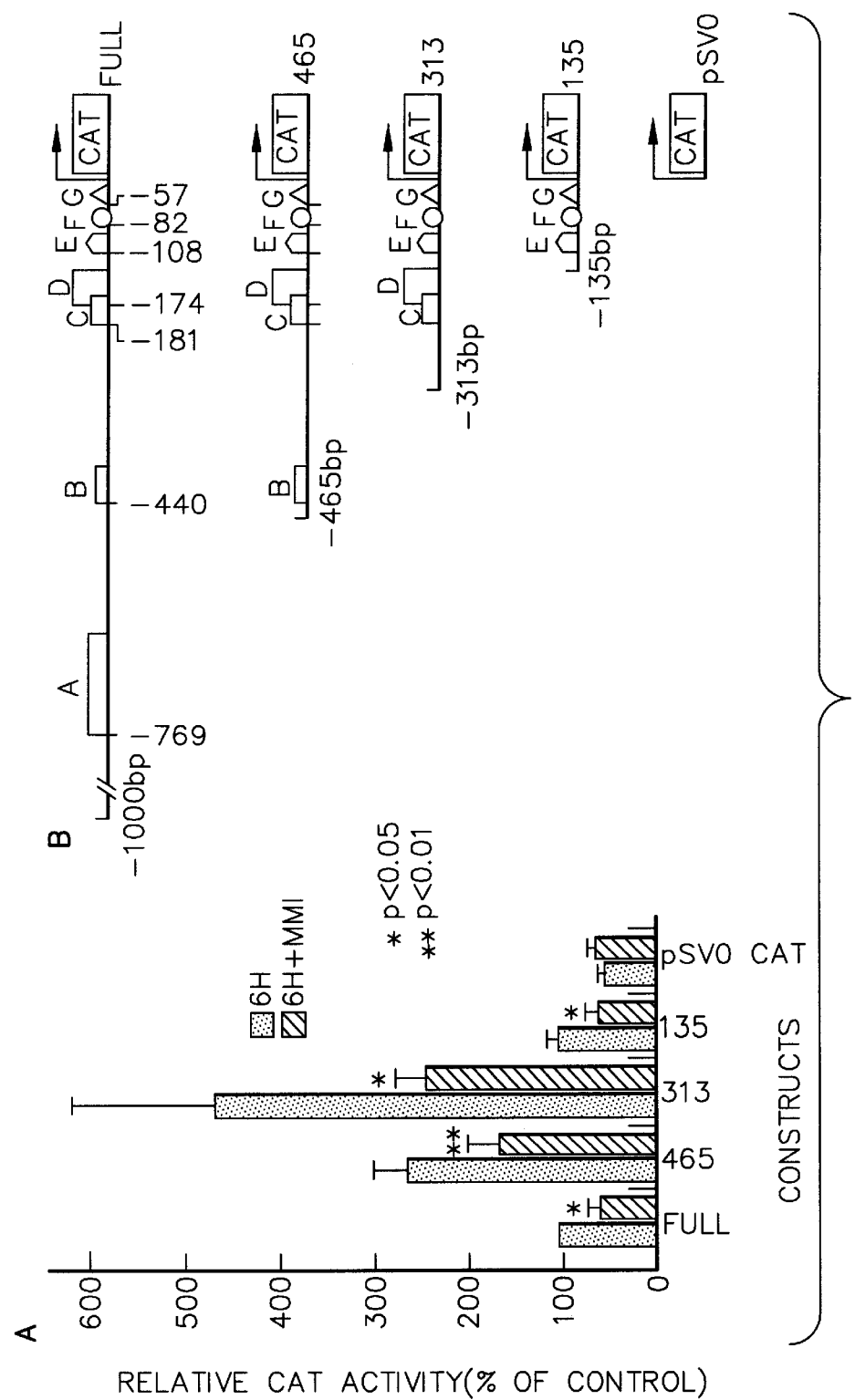

In a second experiment (FIG. 10, Panel A), we tested the effect of MMI and TSH on the promoter activity of CAT chimeras of 5 '-deletion mutants of the swine class I promoter in FRTL-5 cells. FRTL-5 cells grown in 6H medium (+TSH) were transfected by electroporation with the different constructs of the PD1 5'-flanking region. After 12 hours, the medium was changed to fresh 6H medium (+TSH), fresh 6H medium plus 5 mM MMI (+TSH/+MMI), or fresh 5H medium with no TSH or MMI; CAT activity was measured 36 hours later. Conversion rates were normalized to luciferase levels and protein; the activity of the −1100 bp construct in cells maintained in 6 H medium (first black bar) was assigned a control value of 100%. Values are the mean ±SE of three different experiments, each performed in duplicate. Differences in the basal level of expression for the different constructs reflect activity of different regulatory elements, some of which are noted in Panel B. Regulatory elements noted include the following: (a) the upstream silencer/enhancer region important in regulating constitutive class I levels in different tissues; (b) serum response element; (c) Enhancer A; (d) the interferon response element; (e) the 38 bp constitutive silencer containing the CRE-like sequence within the constitutive silencer element (Giuliani C., et al., ibid (1995); Saji M., et al., ibid (1997)). Also noted are (f) the CCAAT and (g) TATA box important in initiation of transcription. These results suggest that any of the constructs could be used to screen MMI derivatives but that p(−203)CAT might be best because its CAT activity is more easily measured and because the MMI inhibitory effect is best.

The action of MMI is also readily measured in cells treated with γ-interferon (γ-IFN). As noted elsewhere, the ability of γ-IFN to increase class I and induce class II antigen expression in FRTL-5 thyroid cells and mimic changes in human thyrocytes seen in ATD is well described (Todd I, et al., ibid (1985); Platzer M, et al., ibid (1987); Misaki T, et al., ibid (1988); Zakarija M, et al., ibid (1988)). Studies of the effect of MMI or MMI derivatives on γ-IFN-increased class I or γ-IFN induced aberrant class II expression are, therefore, a reasonable model to show activity that is important in ATD and other immune diseases. Using p(−1100) CAT, p(−203)CAT, and p(−127)CAT class I chimeras as examples, the ability of γ-IFN to increase class I promoter expression is readily measured and the ability of MMI to decrease this action is also readily measured (Table 5).

In this experiment, FRTL-5 cells were grown to near confluency in 6H medium (plus TSH) and then were maintained in 5H medium (no TSH) for 7 days before being treated with γ-IFN or γ-IFN plus MMI for 40 hours. Control cells were those maintained in 5H medium for the same 40 hours. CAT activity was measured as described above. The γ-IFN treatment increased CAT activity significantly ($P<0.05$ or $0.01$) in cells transfected with all the CAT plasmids except the pSV0 control. Importantly, the MMI significantly decreased the ability of γ-IFN treatment to increase CAT activity ($P<0.01$) in cells transfected with all the CAT plasmids except the pSV0 control.

TABLE 5

EFFECT OF 5 MM MMI OR 100 U/M γ-INTERFERON ON THE EXOGENOUS PROMOTER ACTIVITY IN FRTL-5 CELLS TRANSFECTED WITH CHIMERIC CAT CONSTRUCTS OF THE 5'-DELETION MUTANTS OF THE SWINE CLASS I PROMOTER.

| CHIMERA | NO TREATMENT CONTROL (CAT ACTIVITY RELATIVE TO p(−1100)CAT) | +γIFN (100 U/ml) % of Control | +γIFN (100 U/ml) + MMI (5 mM) % of Control |
|---|---|---|---|
| p(−1100) | 100 | 460 ± 40 | 163 ± 48 |
| p(−203) | 520 | 750 ± 25 | 95 ± 26 |
| p(−127) | 100 | 500 ± 27 | 55 ± 4 |
| pSV0 | 45 | 48 ± 7 | 38 ± 9 |

Table 6, presents results of the effect of MMI, multiple MMI derivatives or tautomeric cyclic thiones on basal class I activity; Table 7 presents results of the effect of MMI, multiple MMI derivatives or tautomeric cyclic thiones on IFN-increased class I promoter activity. The action of compound 10 is clearly best in both cases, followed by compounds 11, 7, and 8.

Figure 11:
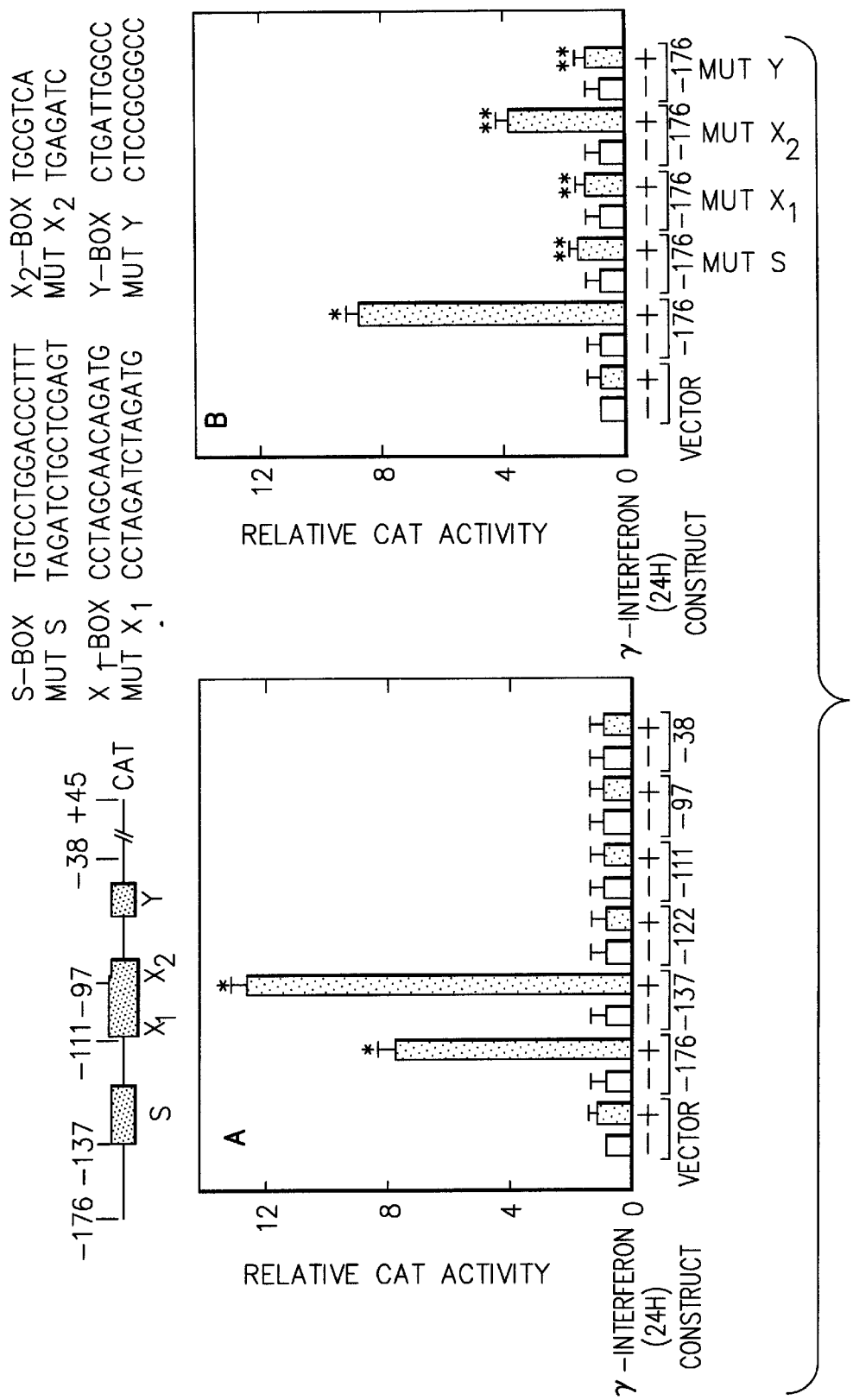
Figure 12:
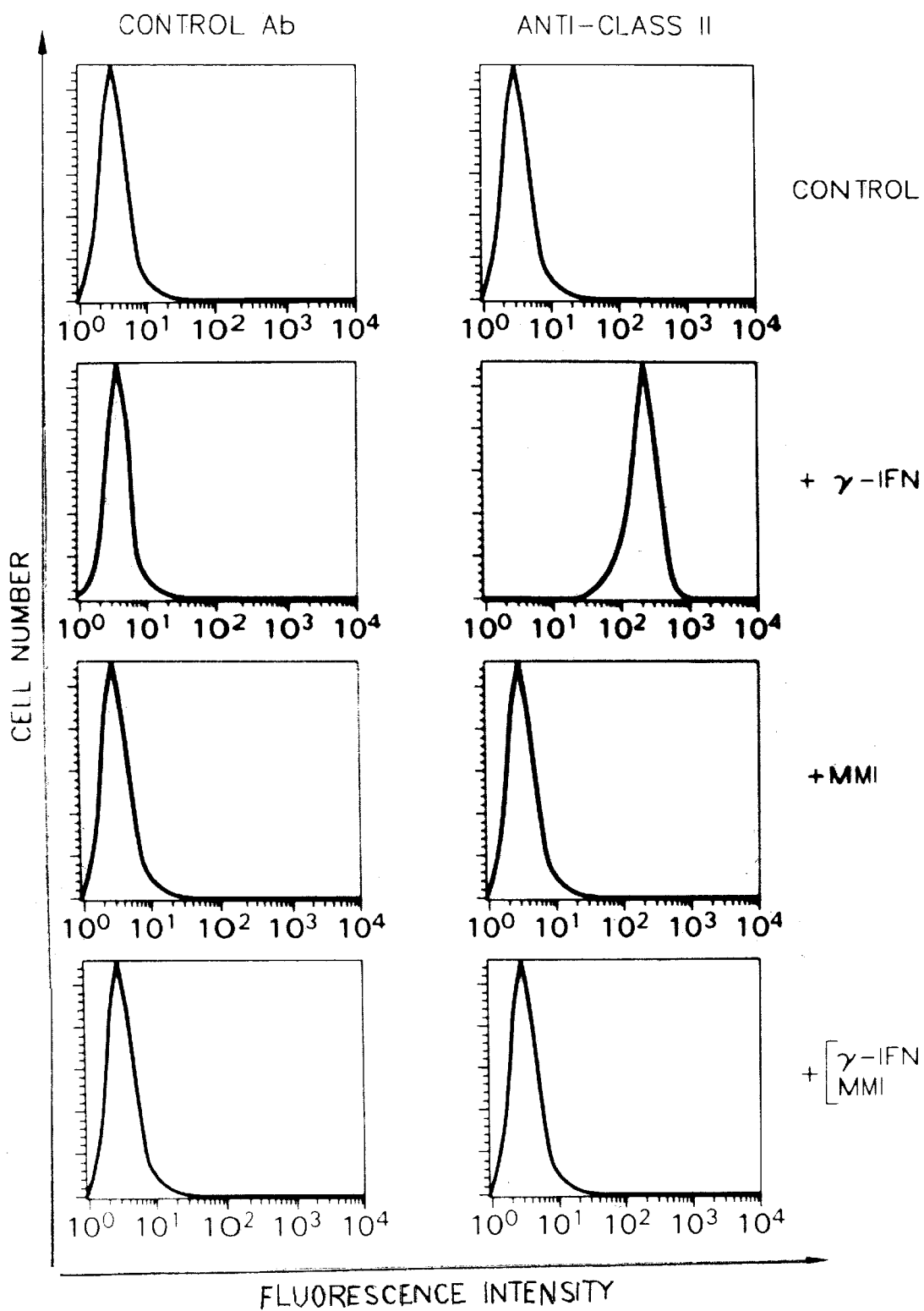

The HLA-DRα-176 bp or −137 bp minimal promoter class II chimeras coupled to CAT were used to evaluate the expression of the HLA-class II gene in FRTL-5 thyrocytes. HLA-DRα is not expressed in transiently transfected FRTL-5 thyrocytes, by comparison to the vector control, unless the cells are treated with rat recombinant γ-IFN (FIG. 11, first and second set of open and closed bars in each Panel). The action of rat -IFN is not duplicated by human γ-IFN and is associated with an increase in endogenous class II expression measured by flow cytometry using fluorescent all partner analysis (FIG. 12). Thus, the γ-IFN action is specific and appears to reflect effects on the endogenous class II antigen. Evaluation of progressive 5' deletions of the −176 bp DRα-CAT chimera to −137, −122, −111, −97, and −38 bp showed that, like immune cells, γ-IFN- induction is lost once the S box, −137 to −123 bp is removed (FIG. 11 Panel A). Also like immune cells, γ-IFN-induction requires not only the S box, but also the $X_1$, $X_2$, and Y boxes for activity. Thus, mutation of each element individually also resulted in the loss (FIG. 11 Panel B, MUT S, MUT $X_1$, and MUT Y) or a significant decrease (FIG. 11B, MUT $X_2$) in the γ-IFN response.

TABLE 6

EFFECT OF DIFFERENT CONCENTRATIONS OF ACTIVE COMPOUNDS ON THE EXOGENOUS PROMOTER ACTIVITY OF FRTL-5 CELLS TRANSFECTED WITH THE CLASS I CAT CHIMERA, P(−203)CAT.
% INHIBITION OF BASAL p(−203)CAT CLASS I PROMOTER ACTIVITY

| | Compound | 25 μM | 100 μM | 1.0 mM | 5 mM |
|---|---|---|---|---|---|
| 1 | Methimazole | 0 | 0 | 32 ± 7 | 74 ± 10 |
| 2 | Metronidazole | 0 | 10 ± 8 | 37 ± 11 | 74 ± 9 |
| 3 | 2-mercaptoimidazole | None | None | None | None |
| 4 | 2-mercaptobenzimidazole | 0 | 0 | 50 ± 12 | 90 ± 14 |
| 5 | 2-mercapto-5-nitrobenzimidazole | ND | ND | ND | 45 ± 8 |
| 6 | 2-mercapto-5-methylbenzimidazole | ND | ND | ND | 57 ± 13 |
| 7 | S-methylmethimazole | 0 | 10 ± 9 | 51 ± 6 | 68 ± 8 |
| 8 | N-methylmethimazole | 5 ± 5 | 48 ± 10 | 72 ± 6 | 87 ± 11 |
| 9 | 5-methylmethimazole | 0 | 0 | 14 ± 10 | 25 ± 7 |
| 10 | 5-Phenylmethimazole | 45 ± 9 | 71 ± 6 | 92 ± 12 | ND |
| 11 | 1-methyl-2-thiomethyl-5(4)nitroimidazole | 11 ± 6 | 51 ± 8 | 89 ± 11 | ND |

Values from three experiments in duplicate, mean ± SD. ND is not done.
Bold values represent significant inhibition ($P < 0.05$ or better).
Experiment in each case was in 6H medium. Treatment was for 36 hours.

TABLE 7

EFFECT OF DIFFERENT CONCENTRATIONS OF ACTIVE COMPOUNDS ON THE EXOGENOUS PROMOTER ACTIVITY OF FRTL-5 CELLS TRANSFECTED WITH THE CLASS I CAT CHIMERA, P(−203)CAT, AND TREATED WITH 100 U/ML γ-INTERFERON.
% INHIBITION OF IFN-INCREASED p(−203)CAT CLASS I PROMOTER ACTIVITY

| | Compound | 10 μM | 100 μM | 1.0 mM | 5 mM |
|---|---|---|---|---|---|
| 1 | Methimazole | 0 | 0 | 35 ± 8 | 72 ± 12 |
| 2 | Metronidazole | 0 | 0 | 45 ± 5 | 84 ± 13 |
| 3 | 2-mercaptoimidazole | None | None | None | None |
| 4 | 2-mercaptobenzimidazole | 0 | 0 | 40 ± 8 | 76 ± 10 |
| 5 | 2-mercapto-5-nitrobenzimidazole | ND | ND | ND | 43 ± 9 |
| 6 | 2-mercapto-5-methylbenzimidazole | ND | ND | ND | 49 ± 7 |
| 7 | S-methylmethimazole | 0 | 14 ± 11 | 50 ± 13 | 58 ± 12 |
| 8 | N-methylmethimazole | 0 | 38 ± 9 | 69 ± 7 | 77 ± 14 |
| 9 | 5-methylmethimazole | 0 | 0 | 10 ± 10 | 29 ± 11 |
| 10 | 5-Phenylmethimazole | 35 ± 10 | 81 ± 14 | 90 ± 13 | ND |
| 11 | 1-methyl-2-thiomethyl-5(4)nitroimidazole | 12 ± 11 | 43 ± 7 | 89 ± 11 | ND |

Values from three experiments in duplicate, mean ± SD. ND is not done.
Bold values represent significant inhibition ($P < 0.05$ or better).
Experiment in each case was in 6H medium. Treatments with interferon and MMI, methimazole derivative, or tautomeric cyclic thione were for 40 hours.

In this experiment transient transfections were performed in FRTL-5 cells grown to near confluency in medium with TSH (6H medium) and treated with 100 U/ml γ-IFN for 24 h after transfection. Results are expressed relative to the vector control in the absence of γ-IFN (first open bar in each panel), after CAT activities were corrected both for luciferase activity and cell protein. These corrections in all cases resulted in less than 5% changes in activity. Results are the mean ±SD of 3 separate experiments performed on 3 different batches of cells. A single asterisk (*) denotes a statistically significant increase ($P<0.01$) in DRα promoter activity induced by γ-IFN; two asterisks (**) denote a statistically significant decrease ($P<0.01$) in γ-IFN-induced DRα promoter activity when the −176 bp DRα minimal promoter contained mutations in the S, $X_1$, $X_2$, and Y boxes. The same results were obtained using an alternative protocol involving cells maintained in medium with no TSH. In FIG. 11 (top left) is a diagrammatic presentation of the −176 bp DRα-CAT chimera with the locations of the S, $X_1$, $X_2$, and Y boxes noted by black boxes and the locations of the 5'-termini of the deletions noted; on the top right of the Figure, the mutations made in S, $X_1$, $X_2$, and Y boxes are presented.

In sum, as is the case in other antigen presenting cells or cells exhibiting aberrant class II expression associated with immune disease, γ-IFN can increase HLA-DRα promoter expression in FRTL-5 cells and the action of interferon requires the same highly conserved 5'-flanking region elements, S, $X_1$, $X_2$, and Y, present in all class II genes for this effect (Bottazzo G F, et al., ibid (1983); Todd I, et al., ibid (1985); Bottazzo G F, et al., ibid (1985); Todd I, et al., ibid (1986); Burmester G R, et al., ibid (1987); Schwartz R S, et al., ibid (1989); Benoist C, et al., ibid (1990); Glimcher L H, et al., ibid (1992); Ting J P-Y, et al., ibid (1993)).

Figure 13:
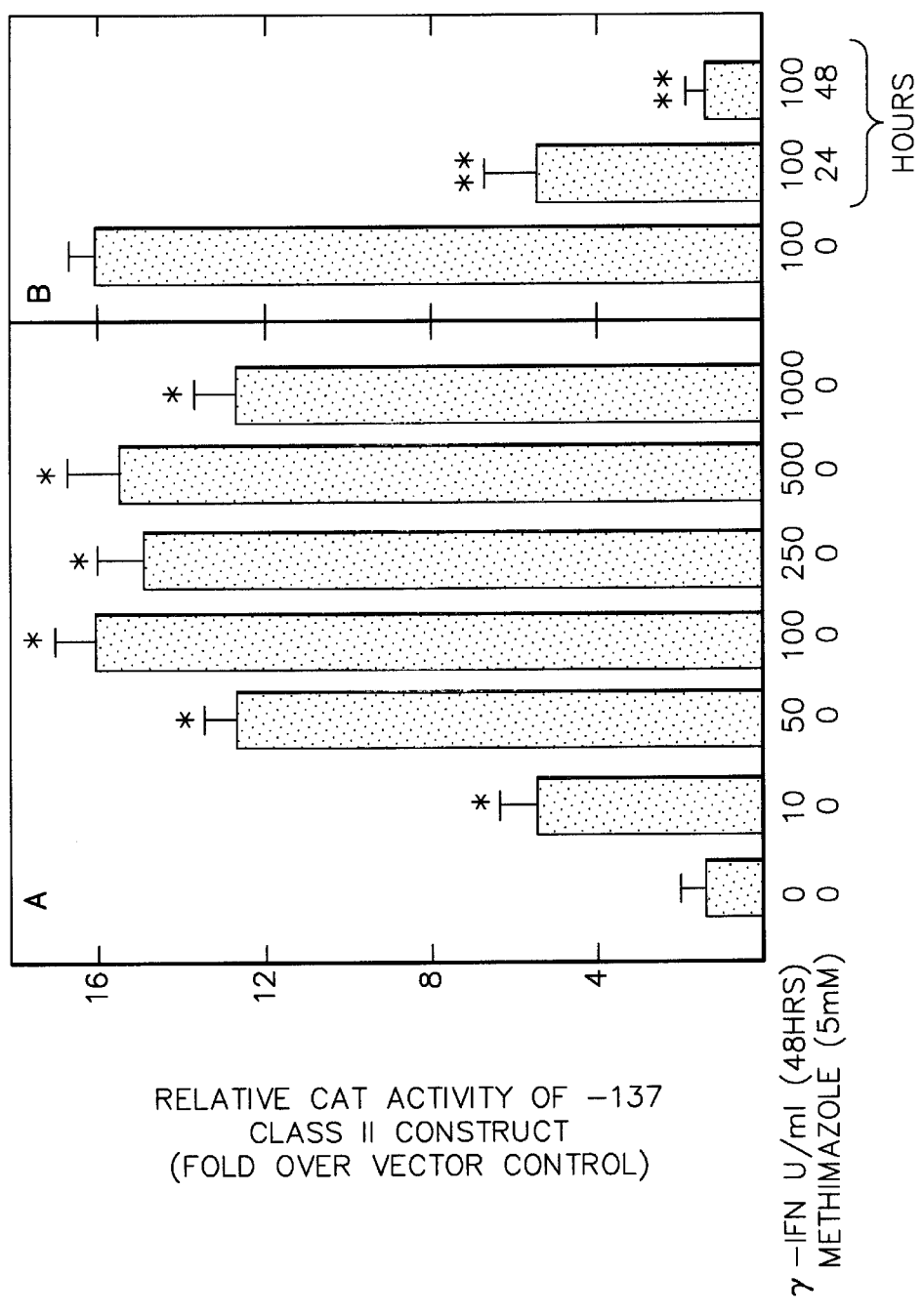
Figure 14:
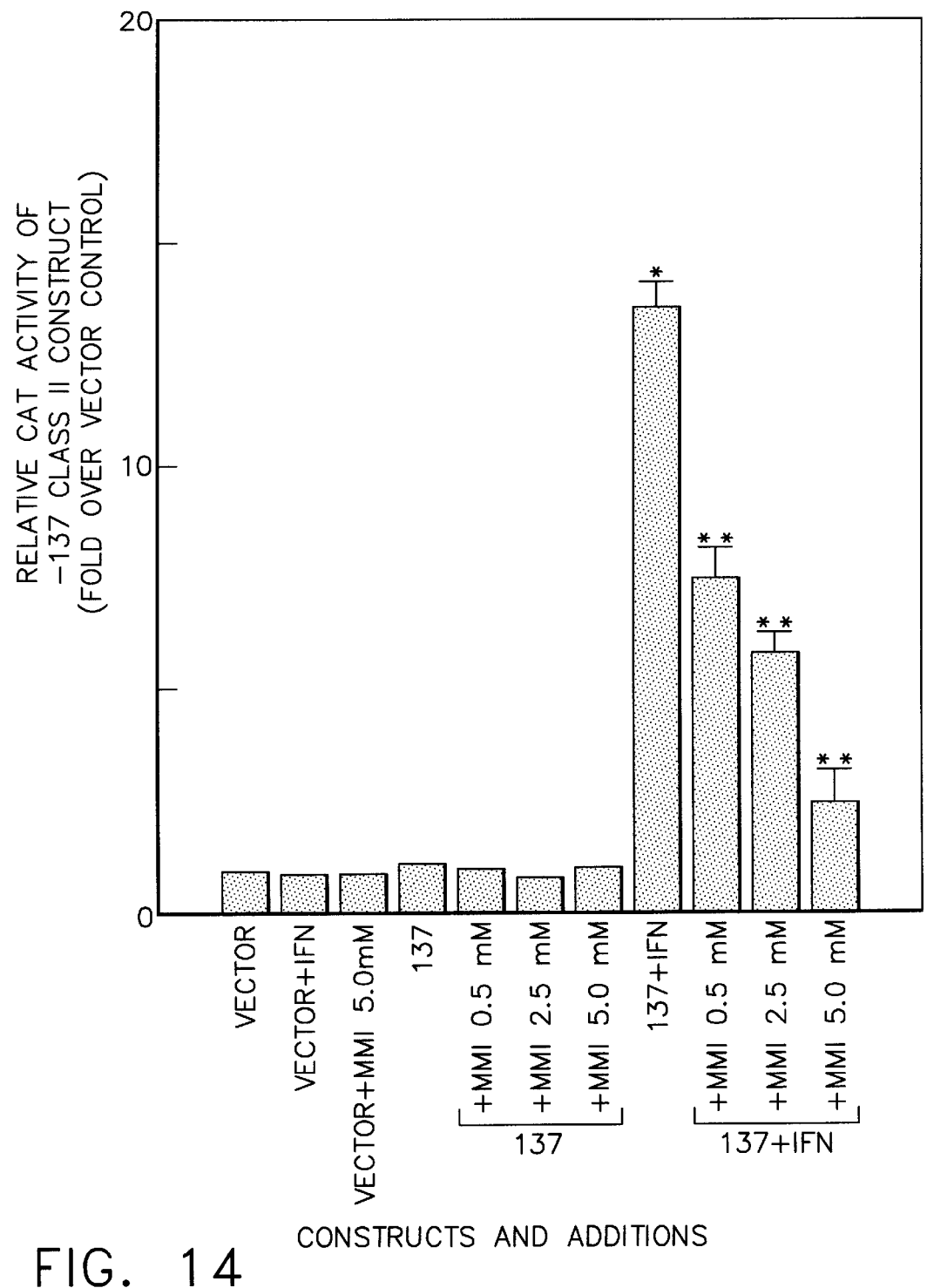

The ability of γ-IFN to increase class II gene expression is dependent on its concentration, whether the −176 bp (data not shown) or −137 bp (FIG. 13) DRα-CAT chimera is used in transient transfection assays. The maximal effect was in each case evident at 100 U/ml γ-IFN (FIG. 13, Panel A). MMI prevents the ability of a maximally effective concentration of γ-IFN to increase the activity of the −137 bp DRα-CAT chimera as a function of time. Thus, CAT activity induced by 100 U/ml γ-IFN was progressively decreased 24 and 48 h after MMI addition (FIG. 13, Panel B). The concentration of MMI in FIG. 13, Panel B is 5 mM; however, the effect was evident at lower MMI concentrations and was dependent on the concentration of MMI (FIG. 14). In these experiments, transient transfections were performed with the −137 bp DRα-CAT chimera. FRTL-5 cells were grown to near confluency in 6H medium and treated with 100 U/ml γ-IFN for the noted times starting 12 h after transfection. MMI was added to duplicate sets of cells, simultaneously with the γ-IFN addition or 24 hours after addition of the γ-IFN. CAT activity was measured 48 h after the addition of γ-IFN and results are expressed relative to the vector control in the absence of γ-IFN after CAT activities were corrected both for luciferase activity and cell protein. These corrections in all cases resulted in less than 5 % changes in activity. Results are the mean ±SD of 3 separate experiments performed on 3 different batches of cells. In FIG. 13, Panel A, a single asterisk (*) denotes a statistically significant increase (P<0.01) in DR promoter activity induced by γ-IFN. In FIG. 13, Panel B, two asterisks () denote a statistically significant decrease in γ-IFN-induced DRα promoter activity with 24 or 48 hours of methimazole exposure. In FIG. 14, two asterisks () denote a statistically significant decrease in γ-IFN-induced DRα promoter activity caused by MMI. The same results were obtained using the alternative transfection protocol involving cells maintained in medium with no TSH.

TABLE 8

EFFECT OF γ-IFN AND MMI ON THE CAT ACTIVITY OF HLA-DRα AND RAT THYROGLOBULIN-CAT CHIMERAS. CAT ACTIVITY (% OF CONTROL WITH NO TREATMENT)

| CHIMERA | CONTROL | +γ-IFN | +γ-IFN + MMI | +MMI |
|---|---|---|---|---|
| −167 HLA-DRα-CAT | 100 | 790 ± 30* | 210 ± 24** | 99 ± 5 |
| TG-688-CAT | 100 | 49 ± 11+ | 160 ± 30++ | 260 ± 12+++ |
| Vector-CAT Control | 100 | 102 ± 7 | 97 ± 5 | 100 ± 4 |

*Significant increase over control (P < 0.01);
**significant decrease in IFN-induced activity (P < 0.01).
+Significant decrease relative to control (P < 0.05);
++significant reversal of the IFN-induced decrease (P < 0.01);
+++significant increase in activity relative to control (P < 0.01).

The action of both γ-IFN and MMI were specific; thus, neither effected the control vector and each had opposite effects on a TG-CAT chimera (Table 8): γ-IFN decreased TG-CAT activity and MMI reversed the γ-IFN-induced decrease in TG-CAT activity. Also, MMI alone increased TG-CAT activity but not HLA-DRα CAT activity (Table 8). In this experiment, like previous experiments, transient transfections were performed in FRTL-5 cells grown to 80% confluency in 6H medium, maintained 6 days in SH medium, and returned to 6H medium for 12 h before transfection as described. Twelve hours later, the medium was changed to fresh 5H medium, supplemented or not with 100 U/ml γ-IFN and/or 5 mM MMI. CAT activity was measured 48 h thereafter. Cell viability was approximately 85% in all experiments. Results are expressed relative to the control with no treatment, after activities were corrected both for luciferase activity and cell protein. These corrections in all cases resulted in less than 5% changes in activity. Results are the mean ±SD of 3 separate experiments.

Consistent and coincident with its effect on γ-IFN-induced exogenous class II gene expression in CAT assays (FIGS. 13 and 14), MMI decreased endogenous class II antigen expression on the cell surface as determined by flow cytometry (FIG. 12). In this experiment, FRTL-5 cells were grown to near confluency in TSH, maintained 8 days in 5H medium, then treated with 100 U/ml γ-IFN, 5 mM MMI, or both for the last 48 hours, as described in FIGS. 13 and 14. Cells were stained with a fluorescein isothiocyanate conjugated class II-specific monoclonal antibody to RT1.B (clone OX-6, Sera Labs, UK) for 60 min at 4° C., washed twice with Dulbecco's phosphate buffered saline, and subjected to laser flow cytometry.

Table 9 summarizes results of experiments evaluating the effect of MMI, MMI derivatives or tautomeric cyclic thiones on γ-IFN induced class II activity in FRTL-5 thyrocytes. The effectiveness of inhibition is similar to that of class I derivatives: compound 10>compound 11>compounds 7 and 8>compound 2>MMI.

Measuring CAT activity of the chimeric CAT constructs of the Class I or Class 11 promoter is, therefore, another way to assay the effect of MMI, MMI derivatives or tautomeric cyclic thiones on Class I or Class II activity. These assays can be used for evaluating agents able to mimic MMI in therapeutic actions related to treatment of autoimmune disease or transplantation therapy.

TABLE 9

EFFECT OF DIFFERENT CONCENTRATIONS OF ACTIVE COMPOUNDS ON THE EXOGENOUS PROMOTER ACTIVITY OF FRTL-5 CELLS TRANSFECTED WITH THE CLASS II CAT CHIMERA, P(−137) CAT AND TREATED WITH 100 U/ML γ-INTERFERON.
% INHIBITION OF IFN-INCREASED p(−137)CAT CLASS II PROMOTER ACTIVITY

|   | Compound | 10 μM | 100 μM | 0.5 mM | 5 mM |
|---|---|---|---|---|---|
| 1 | Methimazole | 0 | 0 | 44 ± 6 | 87 ± 9 |
| 2 | Metronidazole | 0 | 0 | 55 ± 10 | 80 ± 4 |
| 3 | 2-mercaptoimidazole | None | None | None | None |
| 4 | 2-mercaptobenzimidazole | 0 | 0 | 29 ± 12 | 73 ± 14 |
| 5 | 2-mercapto-5-nitrobenzimidazole | ND | ND | ND | 39 ± 13 |
| 6 | 2-mercapto-5-methylbenzimidazole | ND | ND | ND | 44 ± 8 |
| 7 | S-methylmethimazole | 0 | 20 ± 15 | 75 ± 6 | 84 ± 15 |
| 8 | N-methylmethimazole | 0 | 43 ± 9 | 79 ± 11 | 88 ± 10 |
| 9 | 5-methylmethimazole | 0 | 0 | 14 ± 12 | 44 ± 18 |
| 10 | 5-Phenylmethimazole | 45 ± 17 | 88 ± 15 | 95 ± 5 | ND |
| 11 | 1-methyl-2-thiomethyl-5(4)nitroimidazole | 22 ± 11 | 52 ± 10 | 95 ± 7 | ND |

Values from three experiments in duplicate, mean ± SD. ND is not done.
Bold values represent significant inhibition ($P < 0.05$ or better).
Experiment in each case was in 6H medium.

EXAMPLE 4

Creation of High Through-Put Assay for Use in Evaluating MMI Derivatives or Tautomeric Cyclic Thiones and Activity of Such Materials in These Assays The previous results describing the action of MMI derivatives or tautomeric cyclic thiones on class I RNA levels, class I and class II gel shifts, and transient transfections using class I and class II promoter constructs indicated that all assays yielded similar results for all compounds. Thus, the order of effectiveness, i.e. compounds 10>11>7 or 8>2>MMI, prevailed in all assays. This created the possibility that a single set of assays might be useful for high through-put screening of different derivatives. From a speed and quantitation point of view, the possibility existed that creating stable transfectants of class I and class II promoter constructs in FRTL-5 thyroid cells might be a useful approach. The following experiments indicate this to be true.

CONSTRUCTION OF MHC CLASS I and Class I PROMOTER-LUCIFERASE CHIMERIC PLASMIDS

The swine PD1 5'-flanking sequence-CAT chimeras (−1100, −203, and −127), as well as two mutants with the CRE site with −107 to −100 bp deleted (−203ΔCRE and −127ΔCRE) were used to create luciferase reporter gene constructs. The inserts were released by restriction enzyme digestion, purified from agarose gel using QIAEX (QIAGEN, Chatsworth, Calif.) and ligated in the NheI-HindIII site of the PGL-2 basic vector (PROMEGA, Madison, Wis.) using a DNA ligation kit from TAKARA biomedicals (TAKARA SHUZO Co). JM109 bacterial competent cells (PROMEGA, Madison, Wis.) were transformed with the ligation reaction and plated in agar plates for 12 h at 37° C. The colonies were picked and screened with minipreps using QIAprep spin plasmid kit (QIAGEN, Chatsworth, Calif.) and restriction enzyme digestion. The plasmids were then purified by CsCl gradient centrifugation.

Similarly, the HLA DRα promoter constructs, p(−176) CAT and p(−137)CAT, inserted into the pCAT-Basic vector were released by restriction enzyme digestion, purified from agarose gel using QIAEX (QIAGEN, Chatsworth, Calif.), and used as templates for the construction by PCR of inserts with a 5' flanking MluI restriction site. The PCR products were purified by phenol-chloroform extraction, digested with MluI and XbaI, purified from agarose gels using QIAEX (QIAGEN, Chatsworth, Calif.) and ligated in the MluI-NheI site of the PGL-2 basic vector (PROMEGA, Madison, Wis.) using the DNA ligation kit from TAKARA biomedicals (TAKARA SHUZO Co.). JM1I9 bacterial competent cells (PROMEGA, Madison, Wis.) were transformed with the ligation reaction and plated in agar plates for 12 h at 37° C. The colonies were picked and screened with minipreps using QIAprep spin plasmid kit (QIAGEN, Chatsworth, Calif.) and restriction enzyme digestion. The plasmids were then purified by CsCl gradient centrifugation.

STABLE TRANSFECTANTS OF FRTL-5 CELLS

The PD1-PGL-2 basic constructs and the Class II-PGL-2 basic constructs were stably transfected in the FRTL-5 cells using a Lipofectamine (GIBCO, Life Technologies, Inc.) method. Near confluent cells in 6H medium were cotransfected with 20 μg of plasmid DNA and 2 μg of a pcDNA3neo or a pPUR selection vector (CLONTECH, Palo Alto, Calif.). After 24–48 hours, 400 μg/ml of G418 (GIBCO, Life Technologies, Inc.) or 10 μM of puromycin (SIGMA) were added to the medium. After 3 weeks the antibiotic-resistant colonies were cloned by limiting dilution and screened to determine their interferon sensitivity. At least 5 cell lines of each construct were isolated, each of whose activity was increased by adding 100 U/ml γ interferon to the medium of the cells. The following data (Tables 10–13) were obtained with one clone of each of the class I or class II-luciferase chimera, but were representative of at least three other clones of each.

LUCIFERASE ASSAY

Luciferase activity was measured using the Luciferase assay system (PROMEGA, Madison, Wis.). Briefly, treated or untreated cells from a 100 mm culture dish were washed with PBS, scraped and collected in microfuge tubes. The pellet was dissolved in 100 μl 1× reporter lysis buffer and incubated at room temperature for 15 minutes. Cells were frozen in dry ice plus ethanol and thawed in water at room temperature. After vortexing for 10 sec, tubes were centrifuged at 12,000×g for 5 min. Twenty μl of the supernatant were mixed with 100 μl of Luciferase assay reagent and immediately placed in a luminometer. Light was measured for a period of 10 sec after a 2 sec delay.

EFFECT OF MMI DERIVATIVES AND TAUTOMERIC CYCLIC THOINES ON STABLE TRANSFECTANTS

Treatment of cells, maintained either in the presence of TSH or its absence, with 100 U/ml interferon, increased class I and class II promoter activity (Table 10). In this experiment FRTL-5 cells were grown to 80% confluency in 6H medium with TSH then treated with 100 U/ml γ-interferon, 5 mM MMI or both together. Luciferase activity was measured after 40 hours as described. Several points are notable. First, interferon increases both class I and class II promoter activity in the stable transfectants. Second, MMI inhibits both interferon-increased class I and interferon-increased class II promoter activity. Third, unlike transient transfection assays, the MMI does not significantly decrease basal class I activity. Finally, the interferon-induced class I activity requires the presence of the CRE; this is consistent with recent results indicating that interferon-induced CIITA is the mediator of the increase in class I as well as class II activity and requires the CRE for its activity (Saji et al., ibid (1997); Montani V., et al., ibid (1998a, 1998b); Balducci-Silano et al., Endocrinology 139: 2300–2313 (1998)).

The activity of different MMI derivatives and tautomeric cyclic thiones on interferon-increased class I activity in p(−203)class I luciferase chimeras is presented in Table 11. The same pattern as evident in transient transfection studies is seen: compound 10 activity>11>7 or 8>2>MMI. Thus, this assay is consistent with the data in the other studies measuring effects on RNA, gel shifts, and transient transfections of promoters. It has however several major advantages. The cells do not require changing to 5H conditions, therefore cell preparation time is reduced. No labor intensive transient transfections are needed. The assay is rapid and does not require a second prolonged incubation with radioactive materials. Finally, because this involves treatment of living cells with each compound, cell toxicity and viability are readily noted and quantitated, providing a better predictive effect for in vivo use than measurement of an enzyme activity.

The activity of different MMI derivatives and tautomeric cyclic thiones on basal class I activity in p(−203)class I luciferase chimeras is presented in Table 12. Of interest, despite the fact that MMI at 1 or 5 mM has no significant effect on the basal activity, it appears that more active derivatives are effective in this screening assay. Again the activities are measured rapidly and within 7 days of splitting cells, including the 40 hour treatment period.

The activity of different MMI derivatives and tautomeric cyclic thiones on interferon-increased class II activity in p(−137)class II luciferase chimera stably transfected into FRTL-5 cells is presented in Table 13. The same pattern as evident in transient transfection studies is seen: compound 10 activity>11>7 or 8>2>MMI. Thus, this assay is consistent with the data in the other studies measuring effects on class I RNA, class I and II gel shifts, and transient transfections of both class I and class II promoters.

TABLE 11

EFFECT OF DIFFERENT CONCENTRATIONS OF ACTIVE COMPOUNDS ON THE EXOGENOUS PROMOTER ACTIVITY OF FRTL-5 CELLS STABLY TRANSFECTED WITH THE CLASS I-LUCERIFASE CHIMERA, p(−203)LUC, AND TREATED WITH 100 U/ML γ-INTERFERON.
% INHIBITION OF IFN-INCREASED p(−203)LUC CLASS I PROMOTER ACTIVITY

| | Compound | 10 μM | 100 μM | 1.0 mM |
|---|---|---|---|---|
| 1 | Methimazole | 0 | 0 | 45 ± 10 |
| 2 | Metronidazole | 0 | 10 ± 6 | 57 ± 5 |
| 3 | 2-mercaptoimidazole | None | None | None |
| 4 | 2-mercaptobenzimidazole | 0 | 0 | 39 ± 6 |
| 5 | 2-mercapto-5-nitrobenzimidazole | 0 | 0 | 9 ± 7 |
| 6 | 2-mercapto-5-methylbenzimidazole | ND | ND | 19 ± 10 |
| 7 | S-methylmethimazole | 0 | 24 ± 6 | 62 ± 9 |
| 8 | N-methylmethimazole | 0 | 42 ± 14 | 77 ± 10 |
| 9 | 5-methylmethimazole | 0 | 0 | 15 ± 11 |
| 10 | 5-Phenylmethimazole | 45 ± 7 | 90 ± 17 | 90 ± 13 |
| 11 | 1-methyl-2-thiomethyl-5(4)nitroimidazole | 14 ± 8 | 73 ± 14 | 92 ± 15 |

Values from three experiments in duplicate, mean ± SD. ND is not done.
Bold values represent significant inhibition (P < 0.05 or better).
Experiment was in 6H medium.
Treatments with interferon and MMI derivatives or tautomeric cyclic thiones were for 40 hours.

TABLE 10

EFFECT OF γ-IFN AND MMI ON THE LUCIFERASE ACTIVITY OF HLA-DRα- AND SWINE CLASS I CHIMERAS STABLY TRANSFECTED INTO FRTL-5 CELLS.
LUCIFERASE ACTIVITY (Light Units or % of control)

| CHIMERA | CONTROL (Light Units) | +γ-IFN (% Control) | +γ-IFN + 5 mM MMI (% Control) | + 5 mM MMI (% Control) |
|---|---|---|---|---|
| p(−203) class I-LUC | 24,750 | 495 ± 30 | *158 ± 23* | 105 ± 38 |
| p(−203ΔCRE) class I-LUC | 8,290 | 139 ± 16 | 106 ± 6 | ND |
| p(−127) class I-LUC | 8,340 | 180 ± 19* | *110 ± 8*** | 135 ± 17 |
| p(−127ΔCRE) class I-LUC | 3,290 | 92 ± 10 | 101 ± 4 | ND |
| −167 HLA-DRα-LUC | 37,400 | 790 ± 45* | *175 ± 24*** | 99 ± 5 |
| −137 HLA-DRα-LUC | 31,650 | 695 ± 42* | *150 ± 30*** | 103 ± 6 |
| Vector-LUC Control | 2190 | 102 ± 6 | 105 ± 5 | 100 ± 6 |

Values from three experiments (mean ± SD). ND is not done.
*Bold values indicate a significant increase over control (P < 0.01);
**Bold and *italicized* values represent a significant decrease relative to the interferon-increased activity (P < 0.01).

TABLE 12

EFFECT OF DIFFERENT CONCENTRATIONS OF ACTIVE
COMPOUNDS ON THE BASAL PROMOTER ACTIVITY OF
FRTL-5 CELLS STABLY TRANSFECTED WITH THE CLASS I-
LUCERIFASE CHIMERA, p(−203)LUC.
% INHIBITION OF BASAL p(−203)LUC CLASS I PROMOTER
ACTIVITY

|    | Compound | 25 μM | 100 μM | 1.0 mM |
|----|----------|-------|--------|--------|
| 1  | Methimazole | 0 | 0 | 0 |
| 2  | Metronidazole | 0 | 0 | 42 ± 6 |
| 3  | 2-mercaptoimidazole | 0 | 0 | 0 |
| 4  | 2-mercaptobenzimidazole | 0 | 0 | 50 ± 5 |
| 5  | 2-mercapto-5-nitrobenzimidazole | 0 | 0 | 0 |
| 6  | 2-mercapto-5-methylbenzimidazole | 0 | 0 | 0 |
| 7  | S-methylmethimazole | 0 | 10 ± 6 | 44 ± 4 |
| 8  | N-methylmethimazole | 9 ± 6 | 44 ± 10 | 51 ± 7 |
| 9  | 5-methylmethimazole | 0 | 0 | 10 ± 10 |
| 10 | 5-Phenylmethimazole | 41 ± 5 | 51 ± 3 | 52 ± 8 |
| 11 | 1-methyl-2-thiomethyl-5(4)nitroimidazole | 9 ± 6 | 54 ± 9 | 48 ± 5 |

Values from three experiments in duplicate, mean ± SD. ND is not done.
Bold values represent significant inhibition (P < 0.05 or better).
Experiment in each case was in 6H medium.
Treatments with MMI, MMI derivatives or tautomeric cyclic thiones was for 40 hours.

TABLE 13

EFFECT OF DIFFERENT CONCENTRATIONS OF ACTIVE
COMPOUNDS ON THE EXOGENOUS PROMOTER ACTIVITY OF
FRTL-5 CELLS STABLY TRANSFECTED WITH THE CLASS II
LUCERIFASE CHIMERA, p(−137)LUC AND TREATED WITH 100
U/ML γ-INTERFERON.
% INHIBITION OF IFN-INCREASED p(−137)LUC CLASS II
PROMOTER ACTIVITY

|    | Compound | 10 μM | 100 μM | 1 mM |
|----|----------|-------|--------|------|
| 1  | Methimazole | 0 | 0 | 37 ± 10 |
| 2  | Metronidazole | 0 | 7 ± 6 | 65 ± 9 |
| 7  | S-methylmethimazole | 0 | 30 ± 7 | 68 ± 10 |
| 8  | N-methylmethimazole | 0 | 43 ± 5 | 84 ± 9 |
| 10 | 5-Phenylmethimazole | 43 ± 20 | 80 ± 7 | 92 ± 10 |
| 11 | 1-methyl-2-thiomethyl-5(4)nitroimidazole | 16 ± 15 | 44 ± 11 | 94 ± 8 |

Values from two experiments in duplicate, mean ± SD.
Bold values represent significant inhibition (P < 0.05 or better).
Experiment was in 6H medium.
Treatments were for 40 hours.

THE GENERIC HIGH THROUGH-PUT ASSAY FOR USE IN EVALUATING MMI AND TAUTOMERIC CYCLIC THIONE DERIVATIVES AND ACTIVITY OF DERIVIATIVES IN THESE ASSAYS

The previous results describing the action of MMI derivatives and tautomeric cyclic thiones on FRTL-5 thyroid cells stably transfected with MHC class I and class II promoter constructs indicated that the assays yielded similar results as for all other assays. Thus, the order or effectiveness, i.e., compounds 10>11>7 or 8>2>MMI, prevailed. These data established, moreover, a preferable procedure for high through-put screening of different derivatives. The procedure is as follows.

1. FRTL-5 cells stably transfected with MHC class I or class II promoter constructs, preferably p(−203)MHC-class I-LUC or p(−137)MHC class II-LUC, respectively, are grown in complete 6H medium plus 5% calf serum and 400 μg/ml G418 (GIBCO, Life Technologies, Inc.) or 10 μM of puromycin (SIGMA), as appropriate, and in either 6, 12, 24 or 96 well plates, according to the numbers of assays required.

2. When cells are 60–70% confluent, the cells are treated with 100 U/ml γ-interferon with or without MMI derivatives, tautomeric cyclic thiones, or other compounds at 5 mM or lower concentrations together with fresh medium. Preferably a range of concentrations is tested from 5 mM to 5 nM, in duplicate.

3. After 36 to 48, preferably 40, hours, cells in 6, 12, or 24 well plates are washed with 1 ml PBS, scraped, collected in microfuge tubes, and centrifuged to pellet the cells.

4. The pellet is dissolved in 20, 50 or 100 μl 1× reporter lysis buffer respectively, by repetitive micropipetting or vortexing, and incubated at room temperature for 15 minutes.

5. Cells are frozen in dry ice plus ethanol and thawed in water at room temperature. After vortexing for 10 sec, tubes are centrifuged at 12,000×g for 5 min.

6. Cells in 96 well plates are directly solubilized by the addition of 100 μl 1× reporter lysis buffer and repetitive pipetting, and incubated at room temperature for 15 min.

7. Five to 100 μl of the supernatant, depending on the plate used, are mixed with 100 to 300 μl Luciferase assay reagent and immediately placed in a luminometer.

8. Light is measured for a period of 10 seconds after a 2 second time delay.

Usually there is no significant difference in protein concentration between wells; however, the luciferase raw data may be normalized by measuring protein concentrations in the supernatant solution. To increase assay sensitivity or to adjust time schedules in laboratories, the cells may be shifted to 5H medium (no TSH) for 2 to 7 days after reaching 60% confluency, then returned to 6H medium 12 hours before treatment is started.

Since interferon increases both class I and class II promoter activity in the stable transfectants and the inhibition of interferon-induced activity is most representative of the action of the compounds in patients with autoimmune disease, this procedure is optimal. However, for class I transfectants, tests without the presence of interferon can be made to assess effects on basal promoter activity. To insure that the assays are specific for interferon action, tests may be performed with p(−203ΔCRE) MHC-class I-LUC transfected cells, which do not respond to interferon.

This assay is consistent with data in other studies measuring effects on RNA, gel shifts, antigen expression, and transient transfections of promoters. It has however several major advantages. The cells do not require changing to 5H conditions, therefore cell prep time is reduced. No labor intensive transient transfections are needed. The assay is rapid and does not require a second prolonged incubation with radioactive materials.

EXAMPLE 5 of the Effect of MMI Derivatives and Tautomeric Cyclic Thiones on MRNA Levels of MHC Class I and MHC Class II.

The ability of the MMI derivatives and tautomeric cyclic thiones to decrease the exogenous MHC class I and MHC class II promoter activity in transiently or stably transfected FRTL-5 cells is paralleled by the ability of the derivatives to similarly decrease MHC class I and class II RNA levels in the same cells. Thus, the promoter activity measurements reflect phenomena within the cell, despite the use of materials from other species such as human or swine promoters or probes and the different assay technologies measuring changes in exogenous vs endogenous gene expression. The data are also consistent with gel shift changes and MHC surface expression (FIG. 12) measuring the protein products regulating gene expression.

Cells and Treatment

The FRTL-5 rat thyroid cells were the same fresh subclone ($F_1$) used previously in the gel shift and transfection studies and had all properties detailed therein. With TSH, their doubling time was 36±6 hours; in its absence, they did not proliferate. After 6 days in 5H medium with no TSH, $1×10^{-10}$ M TSH elevated cAMP levels, iodide uptake, and thymidine incorporation into DNA>10 fold. Cells were diploid, between the 5th and 25th passage and were grown in Coon's modified F12 medium supplemented with 5% calf serum, 1 mmol/L nonessential amino acids (GIBCO, Grand Island, N.Y.) and a mixture of 6 hormones (6H) as described: TSH ($1×10^{-10}$ M), insulin (10 µg/ml), hydrocortisone (0.4 ng/ml), human transferrin (5 µg/ml), somatostatin (10 ng/ml) and glycyl-L-histidyl-L-lysine acetate (10 ng/ml) (Ambesi-Impiombato FS, U.S. Pat. No. 4,608,341 (1986); Kohn, L. D., et al., U.S. Pat. No. 4,609,622 (1986)). Passage was every 7–10 days; fresh media was added every 2 or 3 days. Cells were shifted to medium with no TSH (5H) for 4–6 days before use. Experiments were initiated by adding $1×10^{-10}$M TSH, 100 U/ml γ-interferon, the noted concentrations of the MMI derivatives or tautomeric cyclic thiones, or combinations of these in fresh medium. Fresh medium alone served as a control. RNA was isolated 40 hours later.

RNA Isolation and Northern Analysis

Total cellular RNA was isolated, Northern analyses performed, and filters sequentially hybridized with the following CDNA probes ($0.5–1.0×10^6$ cpm/mL) as described (Isozaki O, et al., Mol Endocrinol 3:1681–1692 (1989); Saji, M., et al., Proc. Natl. Acad. Sci. U.S.A., 89: 1944–1948 (1992); Saji, M., et al., J. Clin. Endocrinol. Metab., 75: 871–878 (1992)). Three of the probes were those previously described: the 1.0 kb HpaII fragment of the swine MHC class I pH7 clone which spans the entire cDNA insert (Saji, M., et al., ibid (1992)); a rat thyroglobulin cDNA which used as a positive control (Santisteban P, et al., J Biol Chem 262:4048–4052 (1987); Isozaki 0, et al., ibid (1989)); and β-actin which was the negative control. The MHC class II DNA probe was a PCR amplified 546 bp product, from between 74 and 619 bp of the class II sequence, which was derived from interferon-treated rat FRTL-5 cell RNA using a sense primer having the nucleotide sequence, 5'-AGCAAGCCAGTCACAGAAGG-3', and an antisense primer with the sequence, 5'-GATTCGACTTGGAAGATGCC-3', two regions which are highly conserved in the class II nucleotide and protein sequence. After amplification using Pfu DNA polymerase, the product was purified on Agarose gels and then random prime radiolabeled using [$^{32}$P]dCTP and Klenow enzyme.

All experiments were repeated at least 3-times with different batches of cells to evaluate biological variability. Values are the mean ±SD of these experiments unless otherwise noted. Significance between experimental values was determined using the student t-test or by two-way analysis of variance. Values were significant if P was less than 0.05 when data from all experiments were considered.

Results

The MMI derivatives and tautomeric cyclic thiones tested decreased both basal class I and interferon-induced class I and class II RNA levels. The effect of the MMI derivatives and tautomeric cyclic thiones on basal class I RNA levels in cells maintained without TSH is presented in Table 14. The effect on γ-interferon-induced class I RNA levels in cells maintained with TSH is presented in Table 15 and on γ-interferon-induced class II RNA levels in cells maintained with TSH in Table 16. In all cases, RNA levels are quantitated by laser densitometry of autoradiograms or by BAS phosphoimaging relative to β-actin. The class I or class II ratio to β-actin levels in control cells determines the 100% level; the % inhibition reflects an effect of the MMI derivative or tautomeric cyclic thiones to decrease this ratio.

In general, the effect of the derivatives was similar in potency in all RNA assays: compound 10>11>7 or 8>2>MMI. More importantly, this order matched the effects of the derivatives, with respect to potency, both on class I and class II gene expression measured in transfection studies testing effects on promoter activity.

Studies with thyroglobulin RNA emphasize the specificity of the derivatives and provide an unexpected result. MMI increases TG RNA levels nearly 2-fold (Table 17) rather than decreasing RNA levels as is the case for class I and class II (Tables 14–16). Unexpectedly, this is not the case for most MMI derivatives and tautomeric cyclic thiones where no comparable increase is evident, particularly in the case of the most effective compounds (10, 11, 7 and 8) in decreasing class I and class II RNA levels. This suggests that these derivatives/thiones may be effective in the treatment of autoimmune diseases with less adverse effects on thyroid function than methimazole

TABLE 14

EFFECT OF DIFFERENT CONCENTRATIONS OF ACTIVE COMPOUNDS ON BASAL CLASS I RNA LEVELS IN FRTL-5 THYROID CELLS
% INHIBITION OF CLASS I RNA EXPRESSION

| | Compound | 100 µM | 1 mM | 5 mM |
|---|---|---|---|---|
| 1 | Methimazole | None | 25 ± 10 | 42 ± 8 |
| 2 | Metronidazole | None | 49 ± 6 | 63 ± 14 |
| 3 | 2-mercaptoimidazole | ND | None | None |
| 4 | 2-mercaptobenzimidazole | None | 34 ± 13 | ND |
| 5 | 2-mercapto-5-nitrobenzimidazole | None | 32 ± 11 | ND |
| 6 | 2-mercapto-5-methylbenzimidazole | None | 23 ± 15 | ND |
| 7 | S-methylmethimazole | 10 ± 8 | 46 ± 9 | ND |
| 8 | N-methylmethimazole | 14 ± 12 | 60 ± 6 | ND |
| 9 | 5-methylmethimazole | None | 15 ± 14 | 30 ± 5 |
| 10 | 5-Phenylmethimazole | 60 ± 8 | 85 ± 16 | ND |
| 11 | 1-methyl-2-thiomethyl-5(4)nitroimidazole | 25 ± 15 | 75 ± 11 | ND (Toxic) |

Values from three separate experiments (Mean ± SD).
Bold values are significant decreases from basal levels.
The experiment in each case used two 100 mM plates of L5 cells maintained in 5H medium for 5 days after reaching near confluency - then treatment for 40 hours.
None is no effect; ND is not done.

TABLE 15

EFFECT OF DIFFERENT CONCENTRATIONS OF ACTIVE COMPOUNDS ON CLASS I RNA LEVELS IN FRTL-5 CELLS MAINTAINED IN TSH AND TREATED WITH 100 U/ML γ-INTERFERON.
% INHIBITION OF CLASS I RNA EXPRESSION

| | Compound | 100 µM | 1 mM | 5 mM |
|---|---|---|---|---|
| 1 | Methimazole | None | 29 ± 7 | 52 ± 15 |
| 2 | Metronidazole | None | 42 ± 5 | 68 ± 13 |
| 3 | 2-mercaptoimidazole | ND | None | None |
| 4 | 2-mercaptobenzimidazole | None | 37 ± 10 | ND |

TABLE 15-continued

EFFECT OF DIFFERENT CONCENTRATIONS OF ACTIVE COMPOUNDS ON CLASS I RNA LEVELS IN FRTL-5 CELLS MAINTAINED IN TSH AND TREATED WITH 100 U/ML γ-INTERFERON.
% INHIBITION OF CLASS I RNA EXPRESSION

| | Compound | 100 μM | 1 mM | 5 mM |
|---|---|---|---|---|
| 5 | 2-mercapto-5-nitrobenzimidazole | None | 19 ± 7 | ND |
| 6 | 2-mercapto-5-methylbenzimidazole | None | 22 ± 16 | 23 ± 11 |
| 7 | S-methylmethimazole | 14 ± 11 | 40 ± 15 | 69 ± 6 |
| 8 | N-methylmethimazole | 9 ± 7 | 49 ± 13 | 73 ± 12 |
| 9 | 5-methylmethimazole | None | 9 ± 5 | 24 ± 6 |
| 10 | 5-Phenylmethimazole | 42 ± 14 | 60 ± 12 | ND |
| 11 | 1-methyl-2-thiomethyl-5(4)nitroimidazole | 19 ± 12 | 59 ± 5 | ND (Toxic) |

Values from three experiments in duplicate, mean ± SD.
ND is not done; None is no effect measurable.
Bold values are significant decreases from basal levels.
Experiment in each case was in 6H medium.
Treatments with interferon and the methimazole derivatives or tautomeric cyclic thiones were for 40 hours.

TABLE 16

EFFECT OF DIFFERENT CONCENTRATIONS OF ACTIVE COMPOUNDS ON CLASS II RNA LEVELS IN FRTL-5 CELLS TREATED WITH 100 U/ML γ-INTERFERON.
% INHIBITION OF CLASS II RNA EXPRESSION

| | Compound | 100 μM | 1 mM |
|---|---|---|---|
| 1 | Methimazole | None | 29 ± 9 |
| 2 | Metronidazole | 11 ± 10 | 45 ± 13 |
| 7 | S-methylmethimazole | 22 ± 17 | 62 ± 14 |
| 8 | N-methylmethimazole | 32 ± 5 | 59 ± 12 |
| 10 | 5-Phenylmethimazole | 75 ± 15 | 87 ± 4 |
| 11 | 1-methyl-2-thiomethyl-5(4)nitroimidazole | 40 ± 11 | 85 ± 7 |

Values from two experiments in duplicate, mean ± SD.
Bold values represent significant inhibition (P < 0.05 or better).
Experiment was in 6H medium.
Treatment with interferon and the MMI derivatives or tautomeric cyclic thiones was for 40 hours.

TABLE 17

EFFECT OF ACTIVE COMPOUNDS ON THYROGLOBULIN RNA LEVELS IN FRTL-5 THYROID CELLS.
% INCREASE IN TG RNA EXPRESSION

| | Compound | 1 mM |
|---|---|---|
| 1 | Methimazole | 207 ± 10 |
| 2 | Metronidazole | *(15 ± 13)* |
| 7 | S-methylmethimazole | 122 ± 14 |
| 8 | N-methylmethimazole | 129 ± 7 |
| 10 | 5-Phenylmethimazole | *7 ± 13* |
| 11 | 1-methyl-2-thiomethyl-5(4)nitroimidazole | 118 ± 6 |

Values from two experiments in duplicate, mean ± SD.
Bold values represent a significant increase (P < 0.05 or better).
*Bold and italicized* values represent a measurable decrease or no increase (P < 0.05 or better).
Experiment was in 6H medium.
Treatment with interferon and the MMI derivatives or tautomeric cyclic thiones was for 40 hours.

Values from two experiments in duplicate, mean ±SD.

Bold values represent a significant increase (P<0.05 or better).

Bold and italicized values represent a measurable decrease or no increase (P<0.05 or better).

Experiment was in 6H medium.

Treatment with interferon and the MMI derivatives or tautomeric cyclic thiones was for 40 hours.

As pointed out in FIG. 12, the ability of MMI to decrease protein/DNA complexes and promoter activity is associated with the ability of MMI to decrease antigen expression as measured by flow cytometry. The MMI derivatives and tautomeric cyclic thiones also decreased γ-IFN-induced MHC class I and class II antigen expression as measured by flow cytometry.

In this experiment $10^6$ cells were incubated with MHC class II or MHC class I-specific antibodies as described (Montani, V., et al., ibid (1998b); Saji, M., et al., ibid (1992a); Balducci-Silano, P. L., et al., Endocrinology 139:2309–2313 (1998)). After 30 min on ice, cells were washed with phosphate buffered saline at pH 7.4 and incubated for 30 min with fluorescein-isothiocyanate (FITC)-conjugated antibodies then analyzed by flow cytometry on a FACScan Cytometer using CellQuest software (Becton Dickinson).

The concentration needed to achieve suppression of the interferon induced class I or class II surface expression was determined by testing different concentrations of the compounds (Table 18). Like all other assays, the order of effectiveness was compound 10>11>7 or 8>2>MMI>3.

TABLE 18

EFFECT OF DIFFERENT CONCENTRATIONS OF ACTIVE COMPOUNDS ON CLASS I OR CLASS II ANTIGEN EXPRESSION IN FRTL-5 CELLS MAINTAINED IN TSH AND TREATED WITH 100 U/ml γ-INTERFERON
Concentration to inhibit IFN-increased antigen expression

| | Compound | Class I | Class II |
|---|---|---|---|
| 1 | Methimazole | 5 mM | 5 mM |
| 2 | Metronidazole | 0.5 ± 1.4 mM | 1.5 ± 1.0 mM |
| 3 | 2-mercaptoimidazole | No Inhibition | No Inhibition |
| 7 | S-methylmethimazole | 424 ± 31 μM | 405 ± 15 μM |
| 8 | N-methylmethimazole | 356 ± 70 μM | 439 ± 93 μM |
| 10 | 5-Phenylmethimazole | 40 ± 10 μM | 54 ± 11 μM |
| 11 | 1-methyl-2-thiomethyl-5(4)nitroimidazole | 110 ± 14 μM | 109 ± 5 μM |

Values from three experiments in duplicate, mean ± SD.
Bold values represent significant inhibition (P < 0.05 or better).
Experiment in each case was in 6H medium.
Treatments with interferon and the methimazole derivatives or tautomeric cyclic thiones were for 40 hours.

EXAMPLE 6

Ability of MMI, MMI derivatives (2-mercaptoimidazole) or tautomeric cyclic thiones (Compound 10) to prevent proteinuria in (NZBxNZW)$F_1$ Mice or Diabetes in NOD mice The objective of these experiments was to determine the effect of MMI and the tautomeric cyclic thiones (compound 10) on the development of lupus in NZB mice or diabetes in NOD mice by comparison to a methimazole derivative, 2-mercaptoimidazole. Compound 10 was the most effective agent determined in the multiplicity of in vitro assays to suppress class I and class II gene expression; in contrast, 2-mercaptoimidazole was less effective than MMI and had negligible ability to suppress class I and class II gene expression. These were assays to validate the identification procedures with an in vivo correlate.

Female (NZB x NZW)$F_1$ mice spontaneously develop an autoimmune disease resembling human systemic lupus erythematosus (SLE) with age (Mozes et al., Clinical Immunology 18:106–113 (1998)). Similarly, female NOD mice develop a disease resembling type 1 diabetes with age (Makino et al., Exp. Anim. 29:1–13 (1980); Wicker, L. S., et al., Diabetes 35:855–860 (1986)). In the former case, proteinuria is a measure of the onset of disease; in the latter case, glucosuria is a measure of the onset of disease.

Methods

Female (NZB x NZW)$F_1$ mice were obtained from Jackson Labs. Animals were followed with AMES 2855 Uristix (Miles) to semiquantitatively measure proteinuria. Proteinuria was taken as a measure of development of SLE and MMI suppression of proteinuria as suppression of renal complexes in kidney (Mozes et al., J. Clin Immunology 18:106–113 (1998)). At 7–8 mos. mice develop proteinuria reflecting renal disease. Treatment was from 2 mos to 6 mos of age. Treatment was oral. Each group had 8 animals to start.

Female NOD mice were also obtained from Jackson Labs, along with control mice from which the strain was developed (Makino et al., Exp. Anim. 29:1–13 (1980); Wicker, L. S., et al., Diabetes 35:855–860 (1986)). Animals showing urine Tes-Tape positivity greater than 1 + were considered positive and to have diabetes (Wicker, L. S., et al., ibid (1986)). At 8–16 weeks, 1040% of NOD mice develop glucosuria and diabetes according to the literature (Wicker, L. S., et al., ibid (1986)).

Results

Figure 15:
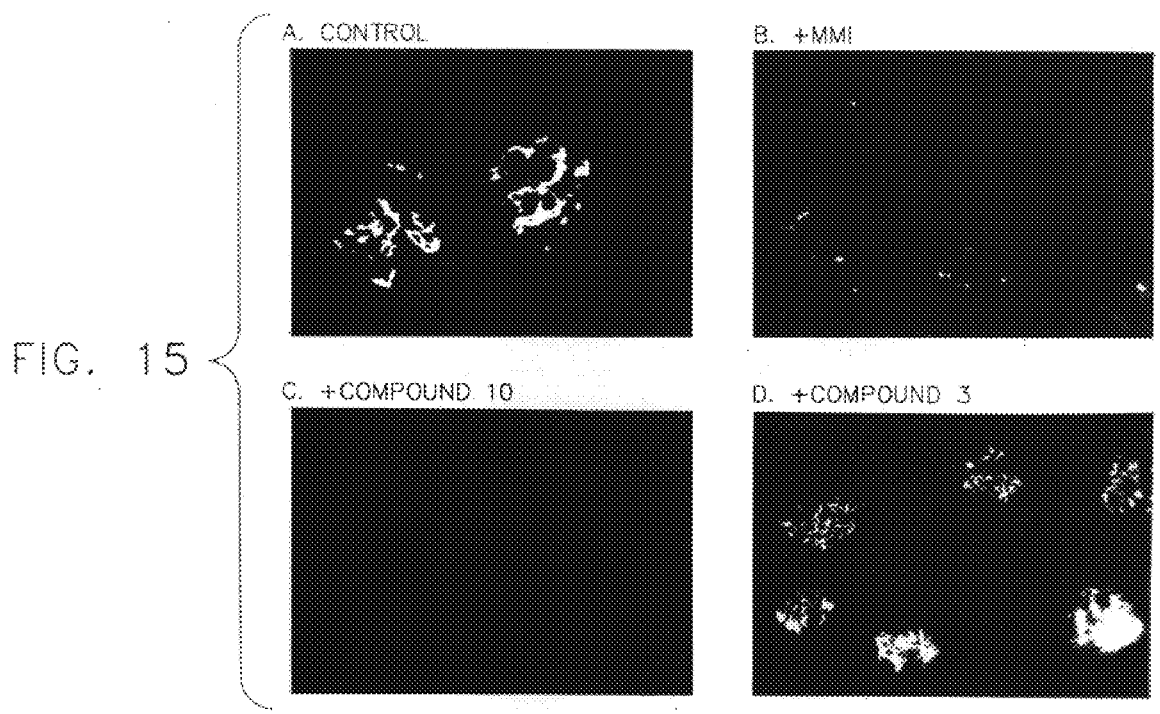

In an experiment with Female (NZB x NZW)$F_1$ mice (Table 19) all surviving control animals and all 2-mercaptoimidazole-treated animals developed significant proteinuria at 7.5 mos. In contrast, both MMI and compound 10 (5-phenylmethimazole), at a fifth the MMI concentration, significantly prevented proteinuria. Animals were sacrificed from each group and kidneys evaluated for immune complexes; data revealed that control animals had significant numbers of immune complexes in their kidneys, whereas this was not true for MMI or compound 10 treated animals (FIG. 15). In this experiment, immunohistology was performed in a blind fashion on 5 µm thick frozen kidney sections which were fixed and stained with FITC-conjugated goat antibodies to immunoglobulin G (γ chain specific) as described (Mozes, et al., Science 261:91–93 (1993); Mozes, E., et al., ibid (1998)). Compound 10, a tautomeric cyclic thione, and MMI are effective in preventing SLE in this experimental model.

Death of some animals in this experiment occurred for technical reasons, i.e. flooding of cages, handling, etc., in the last 2 mos. However, losses in the control group were similar to experimental groups. MMI, 2-mercaptoimidazole, and Compound 10 treatments were administered during the period between 2 and 6.25 months of age.

Table 20 presents results of the ability of Female NOD mice (5 animals were in each group) to develop glucosuria and diabetes when treated with MMI and compound 10 (5-phenylmethimazole) at a fifth the MMI concentration, by comparison to no treatment or treatment with 2-mercaptoimidazole. Mice were from Jackson Labs in this experiment. Animals showing urine Tes-Tape positivity greater than 1+ were considered positive and to have diabetes.

In this experiment all surviving control animals and all 2-mercaptoimidazole-treated animals developed diabetes by 12 weeks. In contrast, both MMI and 5-phenylmethimazole, at a fifth the MMI concentration, prevented glucosuria. Compound 10 and MMI are therefore effective in preventing diabetes in the NOD mouse example of diabetes. Death of animals for technical reasons, i.e. flooding of cages, handling, etc., was similar in control and experimental groups and did not effect results.

The results in these two experiments support the conclusion that the in vitro assays can detect effective drugs to treat autoimmune disease in vivo based on their ability to suppress class I and class II gene expression in vitro in rat FRTL-5 cells. Moreover, the ability of compound 10 to do this at one-fifth the MMI concentration and to be nontoxic appears to validate the hypothesis that use of the assay protocol in FRTL-5 thyroid cells in culture is reasonably predictive of in vivo efficacy.

TABLE 19

ABILITY OF MMI, MMI DERIVATIVES (2-MERCAPTO-IMIDAZOLE), AND TAUTOMERIC CYCLIC THIONES (COMPOUND 10) TO PREVENT PROTEINURIA IN (NZB X NZW)$F_1$ MICE
Animals With Proteinuria

| | 6 mos (mg/dl proteinuria) | | | 7.5 mos (mg/dl proteinuria) | | |
|---|---|---|---|---|---|---|
| Treatment | Neg Trace | 30–500 | >500 | Neg-Trace | 30–500 | >500 |
| None | of 8 | 5 of 8 | 2 of 8 | 0 of 6 | 2 of 6 | 4 of 6 |
| 0.05% MMI | 8 of 8 | 0 of 8 | 0 of 8 | 3 of 5 | 2 of 5 | 0 of 5 |
| 0.01% 5-Phenylmethimazole | 8 of 8 | 0 of 8 | 0 of 8 | 5 of 6* | 1 of 6 | 0 of 6 |
| 0.05% 2-mercaptoimidazole | 3 of 7 | 4 of 7 | 0 of 7 | 0 of 6 | 3 of 6 | 3 of 6 |

*statistically significant, $p < 0.05$.

TABLE 20

ABILITY OF MMI, MMI DERIVATIVES (2-MERCAPTO-IMIDAZOLE) AND TAUTOMERIC CYCLIC THIONES (COMPOUND 10) TO PREVENT GLUCOSURIA IN NOD MICE
Animals with Glucosuria

| Treatment | 4 weeks | 8 weeks | 12 weeks | 14 weeks |
|---|---|---|---|---|
| None | 0 of 5 | 2 of 5 | 4 of 4 | 2 of 2 |
| 0.05% MMI | 0 of 5 | 0 of 5 | 1 of 3* | 0 of 3** |
| 0.01% 5-Phenylmethimazole | 0 of 5 | 0 of 5 | 0 of 4* | 0 of 4** |
| 0.05% 2-mercaptoimidazole | 0 of 5 | 2 of 5 | 3 of 3 | 3 of 3 |

*statistically significant, $p < 0.05$;
**statistically significant, $p < 0.01$

EXAMPLE 7

Effect of Methimazole and Tautomeric Cylic Thione Derivatives on Interferon Induced Decreases in Y Box Protein Levels One factor known to suppress MHC class I and class II gene expression is a Y box binding protein (Saji, M., et al., ibid (1997); Ting, J. P-Y., et al., J. Exp. Med. 179:1605–1611 (1994)). The human Y box protein, YB-1, was cloned based on its ability to bind to the Y box of the MHC class II gene, an inverted CCAAT box (Didier, D. K., et al. Proc. Natl. Acad. Sci. USA 85:7322–7326 (1988)). Transfection of YB-1 was shown to suppress HLA-DRα gene expression in human glioblastoma cells and FRTL-5 thyrocytes (Ting, J. P-Y., et al., ibid (1994); MacDonald, G. H., et al., J. Biol. Chem. 270:3527–3533 (1995); Montani, V., et al., ibid (1998a)). The Y box protein in FRTL-5 cells was cloned based on its ability to suppress thyrotropin receptor (TSHR) gene expression (Shimura, H., et al., J. Biol. Chem. 268:24125–24137 (1993); Ohmori, M., et al., Mol. Endocrinol. 10:76–89 (1996)) and therefore termed TSHR suppressor element binding protein-i (TSEP-1). TSEP-1 is a component of the thyroid autoregulatory system wherein TSH/cAMP decreases TSHR and MHC class I gene expression as FTRL-5 thyroid cells progress through the functional and growth phases of the cell cycle after TSH challenge (Shimura, H., et al. ibid (1993); Ohmori, M., et al., ibid (1996); Kohn, L. D., et al., ibid (1995)). TSH/cAMP increase Y box gene expression, the Y box is a suppressor of TSHR and class I gene expression, and, as a result, TSHR and class I gene expression is decreased.

Figure 16:
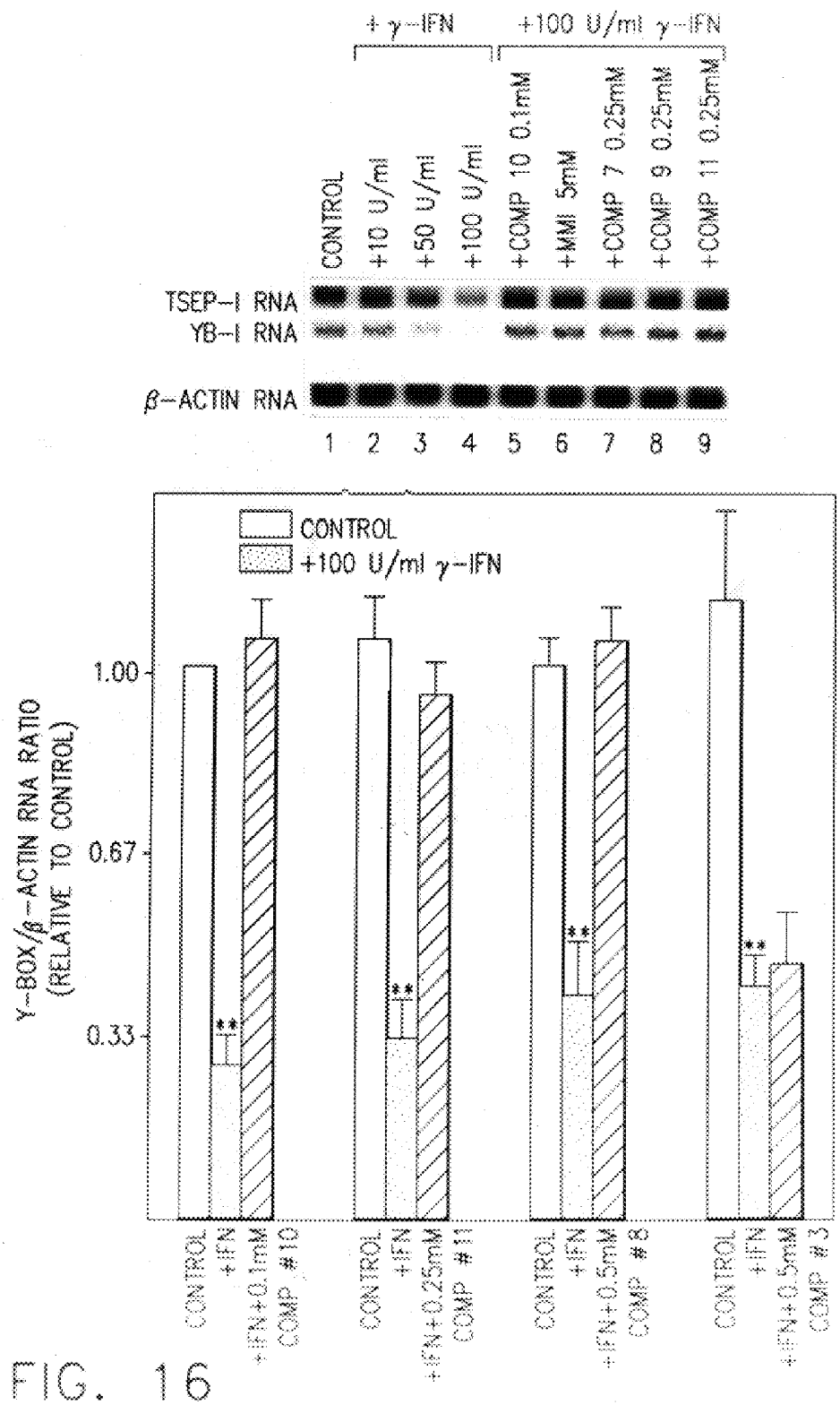

Whereas γ-IFN decreases Y box protein RNA levels in FTRL-5 cells, MMI can reverse this action (FIG. 16). In this experiment, FTRL-5 cells were maintained in complete 6H medium plus 5 % calf serum and treated with 100 Units/ml γ-IFN, an active selected from 5 mM methimazole, 0.1 mM compound 10, 0.25 mM compound 11, 0.5 mM or 0.25 mM compounds 7, 8 and 9, or 0.5 mM compound 3, or both IFN and the different actives for 40 hours before total cellular RNA was isolated and northern analysis performed as described (Isozaki, O., et al., ibid (1989); Saji, M. et al., Endocrinology 130:520–533 (1992); Ohmori, M., et al., ibid (1996)). The rat TSEP-1 probe was the clone 31 insert, residues 5 to 1395 of the rat TSEP-1 nucleotide sequence reported (Ohmori, M., et al., ibid (1996)); rat β-actin was kindly provided by Dr. B. Paterson (NCI, Bethesda, Md.). Radiolabeling of all probes, hybridization (0.5–1.0×10$^6$cpm/ml), and washing were as described (Isozaki, O., et al., ibid (1989); Saji, M., et al., ibid (1992); Ohmori, M., et al., ibid (1996)).

The effect of MMI derivatives and tautomeric cyclic thiones on γ-IFN-decreased TSEP-1 levels is presented in Table 21. The ability of the compounds to reverse the γ-IFN-induced decrease in TSEP-1 RNA levels is once again 10>11>7 or 8>2>MMI>3. This mimics data in all other assays.

Figure 17:
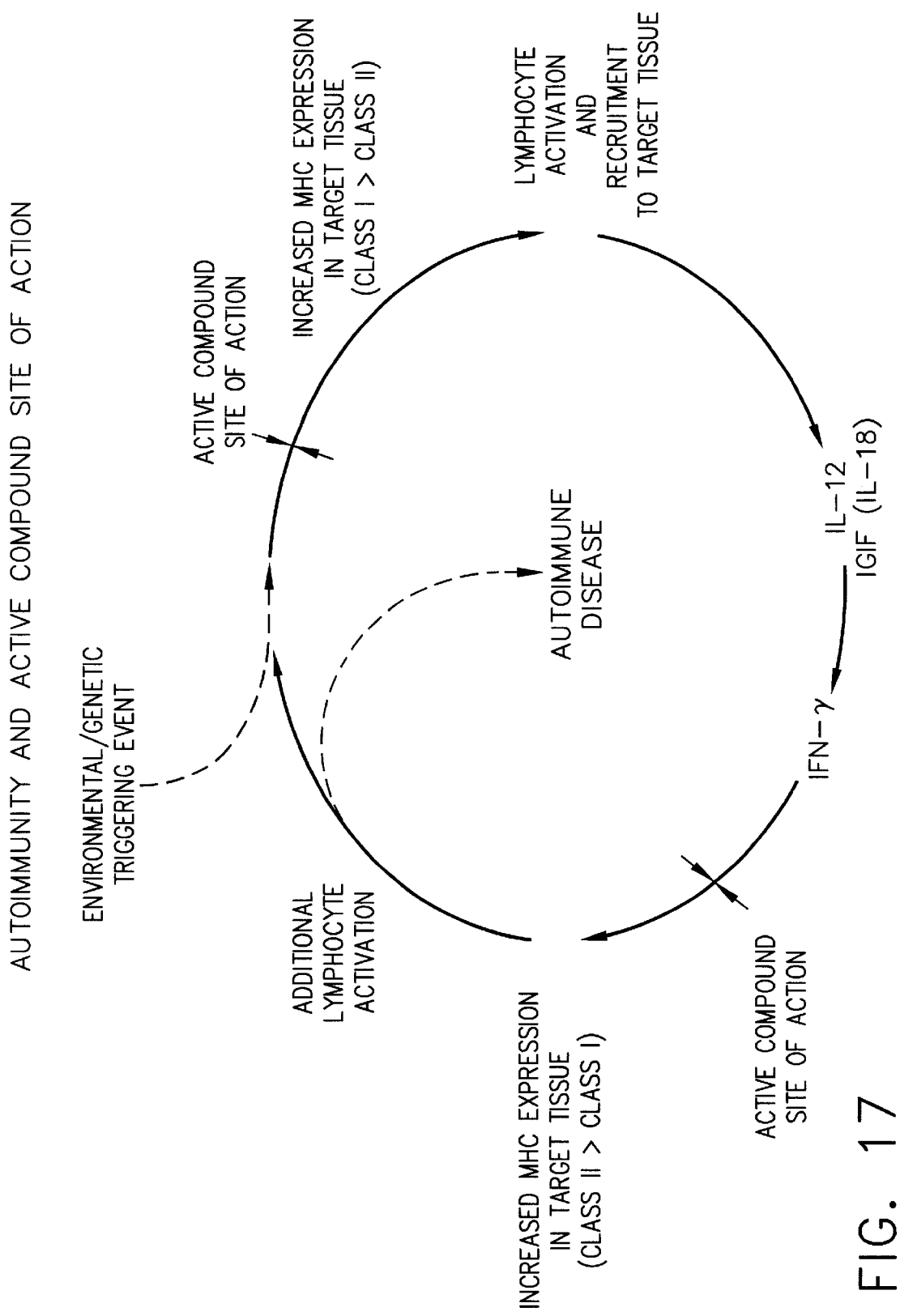

I and class II gene expression. In short, it is reasonable to presume that one means by which γ-IFN increases MHC expression is to decrease Y box suppression of both genes. The data further show that MMI, MMI derivatives and tautomeric cyclic thiones reverse the γ-IFN induced decrease in Y box RNA levels coincident with their action to decrease γ-IFN-induced increases in MHC gene expression estimated by gel shifts, RNA levels, or promoter activity. In sum, we suggest that γ-IFN simultaneously reduces class II suppressive action by decreasing TSEP-1 RNA levels and increases class II expression by increasing CIITA RNA levels. The net result is "aberrant" expression of MHC class II and abnormal class I expression. Methimazole reverses this by reversing the effect of γ-IFN on TSEP-1 (Y box) RNA levels and eliminating the γ-IFN-induced complexes with the HLA-DRα 5'-flanking region (Montani, V., ibid (1998a)). The derivatives shown herein to be more active in suppressing IFN-increased class I and class II gene expression have greater abilities than MMI to reverse the effect of IFN on Y box gene expression. One effect of these agents is thus to prevent or reverse the action of interferon to alter MHC gene expression and exacerbate the autoimmune response (FIG. 17). The agents are also likely to decrease the initial or primary insult on the target tissue which initiates the autoimmune process (FIG. 17) as evidenced by decreases in basal class I gene expression.

Of interest, the MMI, MMI derivatives, and tautomeric cyclic thiones have a minimal effect on basal Y box RNA levels. This reinforces the possibility that the action of the compounds is selective in its effect on γ-IFN-induced changes in Y box RNA levels and will not harm normal physiologic processes controlled by Y box.

TABLE 21

EFFECT OF γ-IFN AND MMI DERIVATIVES OR
TAUTOMERIC CYCLIC THIONES ON Y BOX PROTEIN (TSEP-1) RNA
LEVELS IN FRTL-5 THYROID CELLS
% INHIBITION OF IFN-DECREASED Y BOX PROTEIN RNA EXPRESSION

|   | Compound | +γIFN % Control | 100 μM CMPD ALONE/+γIFN | 1 mM CMPD ALONE/+γIFN | 5 mM CMPD ALONE/+γIFN |
|---|---|---|---|---|---|
|   | NONE (Control) | 45 ± 6% | — | — | — |
| 1 | Methimazole | — | 105 ± 8%/42 ± 7% | 104 ± 12%/87 ± 7% | 115 ± 9%/149 ± 12% |
| 2 | Metronidazole | — | 104 ± 4%/43 ± 6% | 106 ± 11%/126 ± 9% | 112 ± 4%/163 ± 15% |
| 3 | 2-mercaptoimidazole | — | 102 ± 7%/42 ± 11% | 94 ± 6%/42 ± 5% | 100 ± 8%/47 ± 4% |
| 7 | S-methylmethimazole | — | 111 ± 16%/83 ± 10% | 108 ± 4% 133 ± 15% | NOT DONE |
| 8 | N-methylmethimazole | — | 119 ± 13%/77 ± 6% | 115 ± 5%/148 ± 12% | NOT DONE |
| 10 | 5-Phenylmethimazole | — | 124 ± 4%/183 ± 12% | 122 ± 8%/178 ± 10% | NOT DONE |
| 11 | 1-methyl-2-thiomethyl-5(4)nitroimidazole | — | 115 ± 6%/108 ± 12% | 112 ± 10%/148 ± 10% | NOT DONE |

Values from three experiments in duplicate, mean ± SD. Treatments with interferon and the methimazole derivatives or tautomeric cyclic thiones were for 40 hours.

YB-1 is the prototype Y box binding protein. It was cloned using the radiolabeled Y box element of the class II promoter to screen a λgt11 expression DNA library (Didier, D. K., et al., ibid (1988)). Direct evidence of the ability of YB-1 to suppress γ-IFN-induced class II gene expression was provided in glioblastoma and FRTL-5 cells (Ting, J. P-Y., et al., ibid (1998a)). Separate studies also showed it suppressed MHC class I gene expression (Saji, M., et al., ibid (1997)). These data show that γ-IFN decreases Y-box RNA levels. Were Y box protein to also decrease, it is reasonable to presume that decreased Y-box suppression of class I and class II would result, since Y box suppresses class

EXAMPLE 8

Preparation of Pharmaceutical Compositions of the Present Invention Composition Administration Means of administering active compounds of the invention include, but are not limited to, oral, sublingual, intravenous, intramuscular, intraperitoneal, percutaneous, intranasal, intrathecal, subcutaneous, or enteral. Local administration to the afflicted site may be accomplished through means known in the art, including, but not limited to, topical application, injection, infusion and implantation of a porous device in which the active compound(s) or compositions of the invention are contained. Accordingly, the active compounds of the invention will generally be administered as a pharmaceutical composition comprising one or more active compounds of the invention in combination with a pharmaceutically acceptable excipient and other formulational aids.

Formulational Aids

Such compositions may be aqueous solutions, emulsions, creams, ointments, suspensions, gels, liposomal suspensions, and the like. Suitable excipients include water, saline, Ringer's solution, dextrose solution, and solutions of ethanol, glucose, sucrose, dextran, mannose, mannitol, sorbitol, polyethylene glycol (PEG), phosphate, acetate, gelatin, collagen, Carbopol®, vegetable oils, and the like. One may additionally include suitable preservatives, stabilizers, antioxidants, antimicrobials, and buffering agents, for example, BHA, BHT, citric acid, ascorbic acid, tetracycline, and the like. Cream or ointment bases useful in formulation include lanolin, Silvadene® (Marion), Aquaphor® (Duke Laboratories), and the like. Alternatively, one may incorporate or encapsulate the active compounds of the invention in a suitable polymer matrix or membrane, thus providing a sustained-release device suitable for implantation near the site to be treated locally. Other devices include indwelling catheters and devices such as the Alzet® minipump. Opthalmic preparations may be formulated using commercially available vehicles such as Sorbi-care® (Allergan), Neodecdron® (Merck, Sharp & Dohme), Lacrilube®, and the like. Further, one may provide the active compounds of the invention in bulking agents, for example human serum albumin, sucrose, mannitol, and the like. A thorough discussion of pharmaceutically acceptable excipients is available in Remington's Pharmaceutical Sciences I (Mack Pub. Co.), incorporated herein by reference.

Oral/Parenteral Administration

The active compounds of the invention can be administered both orally and parenterally in accordance with conventional procedures for the treatment of autoimmune disease and performance of organ and/or tissue transplantation. The amount of active compound required to treat any particular autoimmune and/or transplant disorder will, of course, vary depending upon the nature and severity of the disorder, the age and condition of the subject, and other factors readily determined by one of ordinary skill in the art. Active compounds are administered in dosage units, preferably divided dosage units, containing the active compound with a suitable physiologically acceptable carrier or excipient, many of which are well known to those in the art and are described above. The dosage units can be in the form of a liquid preparation, e.g., solutions, suspensions, dispersions, or emulsions, or they may be in solid form such as pills, tablets, capsules or the like. Compositions in unit dosage form, i.e., pharmaceutical compositions which are available in a pre-measured form suitable for single dose administration without requiring that the individual dosage be measured out by the user, for example, pills, tablets, capsules, or ampules are particularly preferred methods of administration of the active compounds of the current invention.

Specific/Preferred Indications

For the treatment of autoimmune and transplantation disorders pharmaceutical compositions in dosage unit form comprise an amount of composition which provides from about 0.05 to about 60 milligrams, preferably from about 0.05 to about 20 milligrams, of active compound per day. To produce dosage units for peroral administration, the active compound of the invention or a salt thereof is combined, e.g., with solid powdered carriers such as lactose, sucrose, mannitol; starches such as potato starch, corn starch or amylopectin, as well as laminaria powder and citrus pulp powder; cellulose derivatives of gelatin, also lubricants such as magnesium or calcium sterate of polyethylene glycols (carbowaxes) of suitable molecular weights may be added, to form compressed tablets or core tablets for sugar coating. The latter are coated, for example, with concentrated sugar solutions which, e.g., can contain gum arabic, talcum and/or titinium dixoide, or they are coated with a lacquer dissolved in easily volatile organic solvents or mixture of organic solvents. Dyestuffs can be added to these coatings, for example, to distinguish between different contents of active substance. Capsules useful herein include, for example, soft gelatin capsules (pearl-shaped closed capsules), geltabs, other capsules which consist, for example, of a mixture of gelatin and glycerin and contain, e.g., mixtures of the active substances or a suitable salt thereof with solid, powdered carriers such as, e.g., lactose, sucrose, sorbital, mannitol; starches such as potato starch corn starch or amylopectin, cellulose derivatives or gelatin, as well as magnesium sterate or steric acid. Suppositories are employed as dosage units for rectal application. These consist of a combination of the active substance or a suitable salt thereof with a neutral fatty base, or also gelatin rectal capsules can be employed which consist of a combination of the active substance or a suitable salt thereof with polyethylene glycols (carbowaxes) of suitable molecular weight.

Ampoules for parenteral, particularly intramuscular administration preferably contain an active compound or a water soluble salt thereof and suitable stabilizing agents, and, if necessary, buffer substances in aqueous solution. Anti-oxidizing agents such as sodium bisulfite, sodium sulfite, ascorbic acid or Rongalit (formaldehyde-sodium bisulfite compound), and the like are suitable as stabilizing agents either alone or combined, in total concentrations between 0.01 and about 0.05 percent of the composition. Because of its ability to form chelates, ascorbic acid has an additional stabilizing effect; in this function it can also be replaced by other chelate-formers. The best suitability of the active ingredient is attained, e.g., by mixtures in suitable ratio of sodium sulfite, sodium bisulfite and/or ascorbic acid, or by the addition of other buffer substances such as citric acid and/or salts thereof. In addition, the ampoules can contain a slight amount of a preservative.

Useful pharmaceutical formulations for administration of the active compounds of this invention may be illustrated below. They are made using conventional techniques.

| CAPSULES | |
|---|---|
| Active ingredient | 0.05 to 20 mg |
| Lactose | 20–100 mg |
| Corn Starch U.S.P. | 20–100 mg |
| Aerosolized silica gel | 2–4 mg |
| Magnesium stearate | 1–2 mg |

| TABLETS | |
|---|---|
| Active ingredient | 0.05 to 20 mg |
| Microcrystalline cellulose | 50 mg |
| Corn Starch U.S.P. | 80 mg |
| Lactose U.S.P. | 50 mg |
| Magnesium stearate U.S.P. | 1–2 mg |
| This tablet can be sugar coated according to conventional art practices. Colors may be added to the coating. | |

-continued

CHEWABLE TABLETS

| | |
|---|---|
| Active ingredient | 0.05 to 20 mg |
| Mannitol, N.F. | 100 mg |
| Flavor | 1 mg |
| Magnesium stearate U.S.P. | 2 mg |

SUPPOSITORIES

| | |
|---|---|
| Active ingredient | 0.05 to 20 mg |
| Suppository base | 1900 mg |

LIQUID

| | |
|---|---|
| Active ingredient | 2.0 percent |
| Polyethylene glycol 300, N.F. | 10.0 percent |
| Glycerin | 5.0 percent |
| Sodium bisulfite | 0.02 percent |
| Sorbitol solution 70%, U.S.P. | 50 percent |
| Methylparaben, U.S.P. | 0.1 percent |
| Propylparaben, U.S.P. | 0.2 percent |
| Distilled water, U.S.P. (q.s.) | 100.0 cc |

INJECTABLE

| | |
|---|---|
| Active ingredient | 0.05 to 60 mg |
| Polyethylene glycol 600 | 1.0 cc |
| Sodium bisulfite, U.S.P. | 0.4 mg |
| Water for injection, U.S.P. (q.s.) | 2.0 cc |

EXAMPLE 9

Treatment of Humans Suffering SLE, an Autoimmune Disease

For treating humans suffering from SLE, active compound(s) of the present invention are administered, preferably orally, but administration may also be parenterally, at a dose of up to 100 mg per day initially. Initial dosing can be followed by a step-wise reduction program, to 50 mg for 20 days, 40 mg for up to 20 days, 35 mg for up to 30 to 60 days, decreasing progressively to 5 mg–30 mg per day. A maintenance dose of 5 mg–10 mg per day for up to 1 year or longer may also be used. Dosages may be decreased by 50 to 100 fold, at least, for preferred active compounds.

Patients can be monitored for alleviation of clinical signs and symptoms of active disease. Specifically monitored parameters can include, autoantibodies, particularly DNA antibodies; PBL cell surface markers, leukopenia; proteinuria; hyperimmunoglobulinemia; and levels of immune complexes in the kidney by punch biopsy.

In addition, TSH or $T_3/T_4$ levels may be monitored to access the therapeutic levels of active compounds of the invention required for control of disease in the SLE patient. When TSH levels increase significantly above the normal range, indicative of the effective action of the active compound, dosage can be decreased to the next dose level. When thyroid hormone levels decrease significantly from the normal range, this also can be used as an indication to lower dosage. If patients exhibit a decrease in thyroid hormones or an increase in TSH, they can be treated with thyroid hormone ($T_3$ or $T_4$) plus active compounds to maintain a euthyroid state. The TSH level is a better index. The same parameters may be assessed in children.

EXAMPLE 10

Treatment of Humans Suffering From or at Increased Risk of Developing IDDM, an Autoimmune Disease Humans discovered to be suffering from juvenile diabetes, Type I diabetes, or determined by those skilled in the art to possess an increased risk of developing IDDM may be treated by administration of active compound(s) of the present invention, preferably orally (although they may also be administered parenterally), at a dose of up to 100 mg per day initially. Initial dosing can be followed by a step-wise reduction program, to 50 mg for 20 days, 40 mg for up to 20 days, 35 mg for up to 30 to 60 days, decreasing progressively to 5 mg–30 mg per day. A maintenance dose of 5 mg–10 mg per day for up to 1 year or longer can also be used. Dosages may however be lowered by 50 to 100 fold, at least, for preferred active compounds.

Patients can be monitored for alleviation of clinical signs and symptoms of active disease. Specifically monitored parameters can include glucosuria, glucosemia, autoantibodies, particularly antibodies known to those skilled in the art to possess positive correlation to disease progression and/or known to those skilled in the art to possess predictive value with regard to an individual's predisposition, and hence increased risk, for IDDM disease; PBL cell surface markers; leukopenia; and glucosuria.

What is claimed is:

1. A pharmaceutical composition comprising a safe and effective amount of a compound selected from

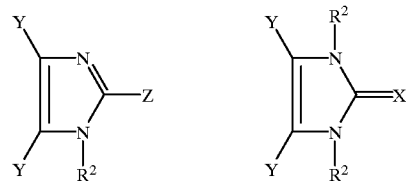

wherein Y is selected from the group consisting of H, $C_1$–$C_4$ alkyl, $C_1$–$C_4$ substituted alkyl, —$NO_2$, and the phenyl moiety

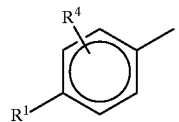

and wherein no more than one Y group in said active compound may be the phenyl moiety; $R^1$ is selected from the group consisting of H, —OH, $C_1$–$C_4$ alkyl, and $C_1$–$C_4$ substituted alkyl; $R^2$ is selected from the group consisting of H, $C_1$–$C_4$ alkyl and $C_1$–$C_4$ substituted alkyl; $R^3$ is selected from the group consisting of H, $C_1$–$C_4$ alkyl, $C_1$–$C_4$ substituted alkyl, and —$CH_2Ph$; $R^4$ is selected from the group consisting of H, $C_1$–$C_4$ alkyl, and $C_1$–$C_4$ substituted alkyl; X is selected from S and O; and Z is selected from —$SR^3$, —$OR^3$ and $C_1$–$C_4$ alkyl; and wherein at least two of the $R^2$ and $R^3$ groups in said compound are $C_1$–$C_4$ alkyl when Y is not a phenyl moiety, and at least one Y is —$NO_2$ when Z is alkyl; and a pharmaceutically-acceptable carrier.

2. A pharmaceutical composition according to claim 1 wherein Z is selected from —$SR^3$ and $OR^3$.

3. A pharmaceutical composition according to claim 2 wherein Z is —$SR^3$ and X is S.

4. A pharmaceutical composition according to claim 3 wherein Y is H.

5. A pharmaceutical composition according to claim 4 wherein $R^3$ is $C_1$–$C_4$ alkyl.

6. A pharmaceutical composition according to claim 5 wherein $R^3$ is methyl.

7. A pharmaceutical composition according to claim 6 wherein at least one of the $R^2$ groups is methyl.

8. A pharmaceutical composition according to claim 4 wherein both $R^2$ groups are methyl.

9. A pharmaceutical composition according to claim 6 wherein the active compound has the formula

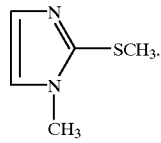

10. A pharmaceutical composition according to claim 1 wherein the active compound has the formula

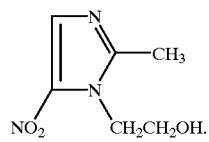

11. A pharmaceutical composition according to claim 4 wherein the active compound has the formula

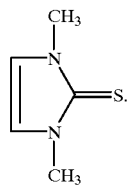

12. A pharmaceutical composition according to claim 1 wherein the active compound has the formula

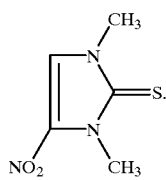

13. A pharmaceutical composition according to claim 1 wherein the active compound has the formula

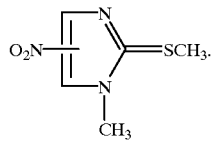

14. A pharmaceutical composition according to claim 3 wherein one of the Y groups is the phenyl moiety.

15. A pharmaceutical composition according to claim 14 wherein $R^1$ and $R^4$ are H.

16. A pharmaceutical composition according to claim 15 wherein $R^3$ is methyl and at least one of the $R^2$ groups is methyl.

17. A pharmaceutical composition according to claim 16 wherein $R^3$ is H.

18. A pharmaceutical composition according to claim 17 wherein both $R^2$ groups are methyl.

19. A pharmaceutical composition according to claim 15 wherein the active compound is selected from the group consisting of

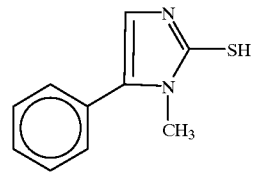

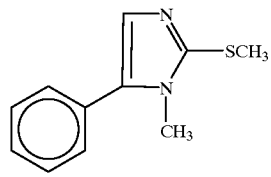

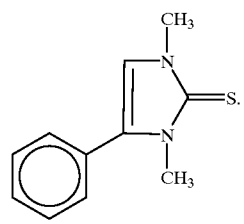

20. A pharmaceutical composition according to claim 1 in unit dosage form.

21. A pharmaceutical composition according to claim 1 which comprises from about 0.01% to about 25% of the active compound and from about 75% to about 99.99% of the pharmaceutically-acceptable carrier.

22. A pharmaceutical compound comprising a safe and effective amount of a compound selected from

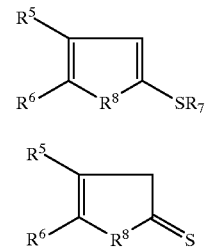

wherein $R^5$ and $R^6$ are selected from the following moiety pairs $CH_3$, $CH_3$; Ph, H and H, Ph; $R^7$ is selected from H and $CH_3$; and $R^8$ is selected from O, S, NH and $NCH_3$; and a pharmaceutically-acceptable carrier.

23. A method of treating autoimmune diseases in a patient in need of such treatment by administering to that patient a safe and effective amount of the pharmaceutical composition according to claim 1.

24. A method of treatment according to claim 23 wherein the pharmaceutical composition is administered intraperitoneally, intravenously, intramuscularly, orally, or topically.

25. A method of treatment according to claim 24 wherein the pharmaceutical composition is administered orally.

26. A method of treatment according to claim 25 wherein the pharmaceutical composition is in unit dosage form.

27. A method of treatment according to claim 24 wherein pharmaceutical composition is administered in an amount such that the active compound is dosed at from about 0.05 to about 50 milligrams per day.

28. A method of treating autoimmune diseases in a patient in need of such treatment by administering to said patient a safe and effective amount of the pharmaceutical composition according to claim 9.

29. A method of treating autoimmune diseases in a patient in need of such treatment by administering to said patient a safe and effective amount of the pharmaceutical composition according to claim 10.

30. A method of treating autoimmune diseases in a patient in need of such treatment by administering to said patient a safe and effective amount of the pharmaceutical composition according to claim 11.

31. A method of treating autoimmune diseases in a patient in need of such treatment by administering to said patient a safe and effective amount of the pharmaceutical composition according to claim 12.

32. A method of treating autoimmune diseases in a patient in need of such treatment by administering to said patient a safe and effective amount of the pharmaceutical composition according to claim 13.

33. A method of treating autoimmune diseases in a patient in need of such treatment by administering to said patient a safe and effective amount of the pharmaceutical composition according to claim 19.

34. A method of treating SLE in a patient in need of such treatment by administering to said patient a safe and effective amount of the pharmaceutical composition according to claim 1.

35. A method of treating diabetes in a patient in need of such treatment by administering to said patient a safe and effective amount of the pharmaceutical composition according to claim 1.

36. The compound having the formula

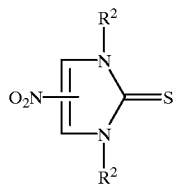

wherein $R^2$ is selected from the group consisting of H, $C_1$–$C_4$ alkyl and $C_1$–$C_4$ substituted alkyl.

37. The compound of claim 36 wherein $R^2$ is selected from the group consisting of $C_1$–$C_4$ alkyl and $C_1$–$C_4$ substituted alkyl.

38. The compound of claim 37 wherein $R^2$ is methyl.

39. A pharmaceutical composition comprising a safe and effective amount of a compound selected from

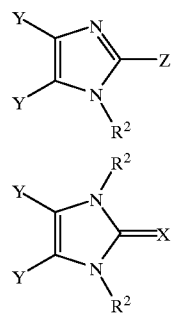

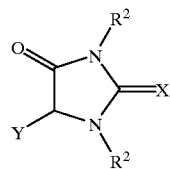

wherein Y is selected form the group consisting of H, $C_1$–$C_4$ alkyl, $C_1$–$C_4$ substituted alkyl, —$NO_2$, and the phenyl moiety

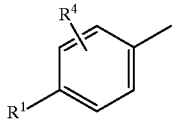

and wherein no more than one Y group is said active compound may be the phenyl moiety; $R^1$ is selected from the group consisting H, —OH, halogens, $C_1$–$C_4$ alkyl, $C_1$–$C_4$ substituted alkyl, $C_1$–$C_4$ ester and $C_1$–$C_4$ substituted ester; $R^2$ is selected from the group consisting of H, $C_1$–$C_4$ alkyl and $C_1$–$C_4$ substituted alkyl; $R^3$ is selected from the group consisting of H, $C_1$–$C_4$ alkyl, $C_1$–$C_4$ substituted alkyl, and —$CH_2Ph$; $R^4$ is selected from the group consisting of H, $C_1$–$C_4$ alkyl and $C_1$–$C_4$ substituted alkyl; X is selected from S and O; Z is selected from —$SR^3$, —$OR^3$, —$S(O)R^3$, —$SR^3$, and $C_1$–$C_4$ alkyl; and wherein at least two of the $R^2$ and $R^3$ groups in said compound are $C_1$–$C_4$ alkyl when Y is not a phenyl moiety, and at least one Y is —$NO_2$, when Z is alkyl: and a pharmaceutically-acceptable carrier.

40. A pharmaceutical composition according to claim 39 wherein the active compound is selected from the group consisting of

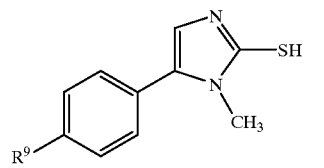

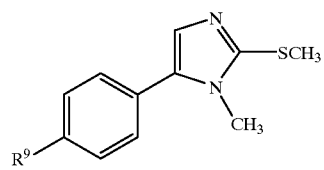

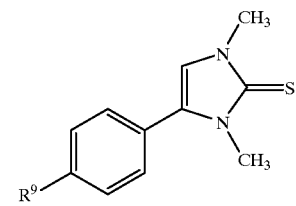

wherein $R^9$ is selected from the group consisting of —OH, —M and —$OOCCH_2M$; wherein M is selected from F, Cl, Br and I.

41. A pharmaceutical composition according to claim 39 wherein the active compound is selected from the group consisting of

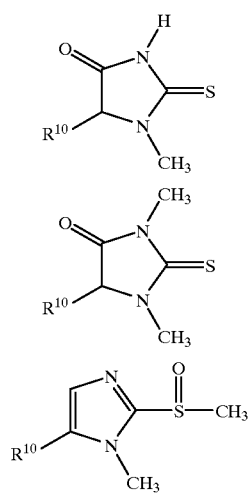

wherein $R^{10}$ is selected from the group consisting of H, —$NO_2$, Ph, 4-HOPh and 4-MPh, wherein M is selected from F, Cl, Br and I.

42. A method of treating autoimmune diseases in a patient in need of such treatment by administering to that patient a safe and effective amount of the pharmaceutical composition accord to claim 39.

43. A method of treating autoimmune disease in a patient in need of such treatment by administering to that patient a safe and effective amount of the pharmaceutical composition according to claim 40.

44. A method of treating autoimmune diseases in a patient in need of such treatment by administering to that patient a safe and effective amount of the pharmaceutical composition according to claim 41.

* * * * *

UNITED STATES PATENT AND TRADEMARK OFFICE
CERTIFICATE OF CORRECTION

PATENT NO.      : 6,365,616 B1                                              Page 1 of 1
DATED           : April 2, 2002
INVENTOR(S)     : Leonard D. Kohn, Robert W. Curley and John M. Rice It is certified that error appears in the above-identified patent and that said Letters Patent is hereby corrected as shown below:

<u>Title page,</u>
Item [56], OTHER PUBLICATIONS "Montain" should read -- Montani -- (both occurrences)

Signed and Sealed this

Fourth Day of June, 2002

Attest:

Attesting Officer

JAMES E. ROGAN
*Director of the United States Patent and Trademark Office*